United States Patent
Ge et al.

(10) Patent No.: US 9,816,091 B2
(45) Date of Patent: *Nov. 14, 2017

(54) CHEMICAL MODIFICATION OF SHORT SMALL HAIRPIN RNAS FOR INHIBITION OF GENE EXPRESSION

(71) Applicant: SomaGenics, Inc., Santa Cruz, CA (US)

(72) Inventors: Qing Ge, Beijing (CN); Brian H. Johnston, Scotts Valley, CA (US); Mark A. Behlke, Coralville, IA (US); Heini Ilves, Santa Cruz, CA (US); Anne Dallas, Santa Cruz, CA (US)

(73) Assignee: SOMAGENICS, INC., Santa Cruz, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/506,349

(22) Filed: Oct. 3, 2014

(65) Prior Publication Data

US 2015/0152414 A1 Jun. 4, 2015

Related U.S. Application Data

(63) Continuation of application No. 13/384,201, filed as application No. PCT/US2010/041782 on Jul. 13, 2010, now Pat. No. 8,871,730.

(60) Provisional application No. 61/225,136, filed on Jul. 13, 2009.

(51) Int. Cl.

| A01N 43/04 | (2006.01) |
|---|---|
| C12N 15/00 | (2006.01) |
| A61K 31/7125 | (2006.01) |
| C12N 15/11 | (2006.01) |
| C12N 15/113 | (2010.01) |
| A61K 31/7088 | (2006.01) |
| A61K 47/48 | (2006.01) |

(52) U.S. Cl.
CPC ........ *C12N 15/113* (2013.01); *A61K 31/7088* (2013.01); *A61K 31/7125* (2013.01); *A61K 47/48123* (2013.01); *C12N 15/111* (2013.01); *C12N 2310/14* (2013.01); *C12N 2310/141* (2013.01); *C12N 2310/315* (2013.01); *C12N 2310/318* (2013.01); *C12N 2310/321* (2013.01); *C12N 2310/344* (2013.01); *C12N 2310/346* (2013.01); *C12N 2310/3515* (2013.01); *C12N 2310/531* (2013.01); *C12N 2320/30* (2013.01); *C12N 2320/53* (2013.01)

(58) Field of Classification Search
CPC combination set(s) only.
See application file for complete search history.

(56) References Cited

U.S. PATENT DOCUMENTS

| 6,001,990 | A | 12/1999 | Wands et al. |
|---|---|---|---|
| 6,174,868 | B1 | 1/2001 | Anderson et al. |
| 7,902,351 | B2 | 3/2011 | Kaspar et al. |
| 8,283,460 | B2 | 10/2012 | Ge et al. |
| 8,426,380 | B2 | 4/2013 | Kaspar et al. |
| 8,779,115 | B2 | 7/2014 | Ge et al. |
| 8,871,730 | B2 | 10/2014 | Ge et al. |
| 2002/0156261 | A1 | 10/2002 | Malvy et al. |
| 2003/0143732 | A1* | 7/2003 | Fosnaugh ............ C12N 15/113 435/325 |
| 2003/0175772 | A1 | 9/2003 | Wang |
| 2003/0228597 | A1 | 12/2003 | Cowsert et al. |
| 2004/0053875 | A1 | 3/2004 | Kreutzer et al. |
| 2004/0053876 | A1 | 3/2004 | Turner et al. |
| 2004/0058886 | A1* | 3/2004 | Scaringe ............... C12N 15/111 514/44 A |
| 2004/0137471 | A1 | 7/2004 | Vickers et al. |
| 2004/0138163 | A1 | 7/2004 | McSwiggen et al. |
| 2004/0209831 | A1 | 10/2004 | McSwiggen et al. |
| 2004/0259247 | A1 | 12/2004 | Tuschl et al. |
| 2005/0130919 | A1 | 6/2005 | Xu et al. |
| 2005/0164210 | A1 | 7/2005 | Mittal et al. |
| 2005/0186586 | A1 | 8/2005 | Zamore et al. |
| 2005/0223427 | A1 | 10/2005 | Leake et al. |
| 2006/0132787 | A1 | 6/2006 | Mestha et al. |

(Continued)

FOREIGN PATENT DOCUMENTS

| JP | 2004-305140 | 11/2004 |
|---|---|---|
| JP | 2007529994 A | 11/2007 |

(Continued)

OTHER PUBLICATIONS

Rogers, Kara. "RNA interference (RNAi)". Encyclopedia Britannica (On-Line), Encyclopedia Britannica, Inc. (pub.), https://www.britannica.com/science/RNA-interference. Accessed Feb. 13, 2017.*

Allerson et al. Fully 2'-modified oligonucleotide duplexes with improved in vitro potency and stability compared to unmodified small interfering RNA. J Med Chem. 2005; 48:901-904.

Amarzguioui et al. Tolerance for mutations and chemical modifications in a siRNA. Nucleic Acids Res. 2003; 31:589-595.

AU2006291568 Examination Report dated May 2, 2012.

Bang et al. Synthesis of hairpin siRNA using 18beta-glycyrrhetinic acid derivative as a loop motif. Tetrahedron Letters. 2009; 50(21): 2545-2547.

Behlke, M. Chemical modification of siRNAs for in vivo use. Oligonucleotides. Dec. 2008;18(4):305-319.

(Continued)

*Primary Examiner* — Jennifer McDonald
(74) *Attorney, Agent, or Firm* — Wilson Sonsini Goodrich & Rosati

(57) ABSTRACT

Aspects of the present invention include the production and use of chemically modified RNAi agents (e.g., shRNAs) in gene silencing applications. The chemically modified RNAi agents disclosed herein have reduced immunostimulatory activity, increased serum stability, or both, as compared to a corresponding RNAi agent not having the chemical modification. Compositions containing chemically modified RNAi agents according to aspects of the present invention (including pharmaceutical compositions) and kits containing the same are also provided.

17 Claims, 15 Drawing Sheets

(56) References Cited

U.S. PATENT DOCUMENTS

| | | | |
|---|---|---|---|
| 2006/0134787 | A1 | 6/2006 | Zamore et al. |
| 2006/0142228 | A1 | 6/2006 | Ford et al. |
| 2006/0223777 | A1 | 10/2006 | Vermeulen et al. |
| 2006/0293272 | A1 | 12/2006 | McSwiggen et al. |
| 2007/0004665 | A1 | 1/2007 | McSwiggen et al. |
| 2007/0048759 | A1 | 3/2007 | Luo et al. |
| 2007/0111228 | A1 | 5/2007 | Jayasena et al. |
| 2007/0149470 | A1 | 6/2007 | Kasper et al. |
| 2007/0173476 | A1 | 7/2007 | Leake et al. |
| 2007/0213293 | A1* | 9/2007 | McSwiggen ....... C12N 15/1131 514/44 A |
| 2007/0231807 | A1* | 10/2007 | Mo ....................... C12N 15/111 435/6.11 |
| 2007/0259827 | A1 | 11/2007 | Aronin et al. |
| 2008/0085869 | A1 | 4/2008 | Yamada et al. |
| 2008/0234217 | A1 | 9/2008 | Davis et al. |
| 2009/0004739 | A1 | 1/2009 | Demura et al. |
| 2009/0005332 | A1 | 1/2009 | Hauser et al. |
| 2009/0035784 | A1 | 2/2009 | Ioannou et al. |
| 2009/0170794 | A1 | 7/2009 | Kaspar et al. |
| 2009/0182136 | A1 | 7/2009 | Wengel et al. |
| 2010/0112686 | A1 | 5/2010 | Ge et al. |
| 2011/0269816 | A1 | 11/2011 | Kaspar et al. |
| 2012/0165397 | A1 | 6/2012 | Ge et al. |
| 2012/0220033 | A1 | 8/2012 | Kaspar et al. |
| 2012/0329857 | A1 | 12/2012 | Ge et al. |

FOREIGN PATENT DOCUMENTS

| | | |
|---|---|---|
| WO | WO 03/010180 | 2/2003 |
| WO | WO 03/070750 | 8/2003 |
| WO | WO 03/070918 | 8/2003 |
| WO | WO 2004/015075 | 2/2004 |
| WO | WO 2004/029281 | 4/2004 |
| WO | WO 2004/061081 | 7/2004 |
| WO | WO 2005/028646 | 3/2005 |
| WO | WO-2005019453 A2 | 3/2005 |
| WO | WO-2005028650 A2 | 3/2005 |
| WO | WO 2005/079533 | 9/2005 |
| WO | WO 2006/031901 | 3/2006 |
| WO | WO 2006/078414 | 7/2006 |
| WO | WO 2007/032794 | 3/2007 |
| WO | WO 2009/029688 | 3/2009 |
| WO | WO 2009/078685 | 6/2009 |
| WO | WO 2010/045384 | 4/2010 |

OTHER PUBLICATIONS

Birmingham et al., "3 UTR Seed Matches, but Not Overall Identity are Associated with RNAi Off-Targets"; Nature Methods, 3(3): 199-204 (2006); Addendum: Nature Methods, 3(6): 487 (2006).

Blight et al., "Efficient Initiation of HCV RNA Replication in Cell Culture"; Science, 290:1972-1974 (2000).

Braasch et al. RNA interference in mammalian cells by chemically-modified RNA. Biochemistry. 2003; 42:7967-7975.

Bridge et al., "Induction of an Interferon Response by RNAi Vectors in Mammalian Cells"; Nature Genetics, 34(3): 263-264 (2003).

Brown et al., "Secondary Structure of the 5' Nontranslated Regions of Hepatitis C Virus and Pestivirus Genomic RNAs"; Nucleic Acids Research, 20(19): 5041-5045 (1992).

Bukh at al., "Sequence Analysis of the 5' Noncoding Regioon of Hepatitis C Virus"; Proc. Nat. Acad. Sci. USA 89:4942-4946 (1992).

Cekaite, et al. Gene expression analysis in blood cells in response to unmodified and 2'-modified siRNAs reveals TLR-dependent and independent effects. J Mol Biol. 2007; 365:90-108.

Chiu, et al. siRNA function in RNAi: a chemical modification analysis. Rna. 2003; 9:1034-1048.

Choo et al., "Genetic Organization and Diversity of the Hepatitis C Virus"; Proc. Natl. Acad. Sci. USA, 88:2451-2455 (1991).

Choung et al. Chemical modification of siRNAs to improve serum stability without loss of efficacy. Biochem Biophys Res Commun. Apr. 14, 2006;342(3):919-927.

CN2006800418459 Office Action dated May 3, 2011 (w/English translation).

CN2006800418459 Office Action dated May 31, 2010 (w/English translation).

CN200980149189.8 Office Action dated Mar. 5, 2013 (w/English Translation).

CN200980149189.8 Office Action dated May 28, 2012 (English Translation only).

CN200980149189.8 Office Action dated Sep. 22, 2013 (w/English Translation).

CN201210277345.2 Office Action dated Jul. 4, 2012 (w/English Translation).

Collingwood et al., "Chemical Modification Patterns Compatible with High Potency Dicer-Substrate Small Interfering RNAs" Oligonucleotides (2008) 18(2):187-200.

Cong et al. Self-stabilized CpG DNAs optimally activate human B cells and plasmacytoid dendritic cells. Biochem Biophys Res Commun. Oct. 31, 2003;310(4):1133-1139.

Czauderna, et al. Structural variations and stabilising modifications of synthetic siRNAs in mammalian cells. Nucleic Acids Res. 2003; 31:2705-2716.

EP05809901.1 search report and opinion dated Nov. 2, 2010.

EP10800405.2 Extended European search report and search opinion dated Sep. 9, 2013.

EP09821213.7 Extended European Search Report dated Mar. 12, 2013.

Fish et al., "Short-Term Cytotoxic Effects and Long-Term Instability of RNAi Delivered Using Lentiviral Vectors"; BMC Molecular biology, 5:9 (2004).

Ge et al. Effects of chemical modification on the potency, serum stability, and immunostimulatory properties of short shRNAs. RNA. Jan. 2010;16(1):118-130.

Ge et al. Minimal-length short hairpin RNAs: the relationship of structure and RNAi activity. RNA. Jan. 2010;16(1):106-117.

Grimm et al., "Fatality in Mice Due to Oversaturation of Cellular MicroRNA/Short Hairpin RNA Pathways"; Nature, 441: 537-541 (2006).

Han et al., "Characterization of the Terminal Regions of the Hepatitis C Viral RNA: Identification of Conserved Sequences in the 5' Untranslated Region and Poly(A) Tails at the 3' End"; Proc. Natl. Acad. Sci. USA, 88: 1711-1715 (1991).

Hannon et al., "Unlocking the Potential of the Human Genome with RNA Interference"; Nature, 451: 371-378 (2004).

Harborth et al. Sequence, chemical, and structural variation of small interfering RNAs and short hairpin RNAs and the effect on mammalian gene silencing. Antisense Nucleic Acid Drug Dev. Apr. 2003;13(2):83-105.

Herrera-Carrillo, et al., "Probing the shRNA characteristics that hinder Dicer recognition and consequently allow Ago-mediated processing and AgoshRNA activity." RNA (2014) vol. 20, pp. 1-9.

Hugle et al., "Current Therapy and New Molecular Approaches to Antiviral Treatment and Prevention of Hepatitis C"; Rev. Med. Virol. 12: 361-371 (2003).

Ilves et al., "Inhibition of Hepatitis C IRES-Mediated Gene Expression by Small Hairpin RNAs in Human Hepatocytes and Mice"; Annals of the New York Academy of Sciences, vol. 1082, Oct. 2006 (Oct. 2006), pp. 52-55.

Jackson, et al. Position-specific chemical modification of siRNAs reduces "off-target" transcript silencing. RNA. 2006; 12:1197-1205.

Jubin et al., "Hepatitis C Virus Internal Ribosome Entry Site (IRES) Stem Loop IIId Contains a Phylogenetically Conserved GGG Triplet Essential for Translation of IRES Folding"; Journal of Virology, 74(22): 10430-10437 (2000).

Judge, et al. Design of noninflammatory synthetic siRNA mediating potent gene silencing in vivo. Mol Ther. 2006; 13:494-505.

Kalota et al. (2007) "Design of antisense oligonucleotides and short interfering RNA duplexes (siRNA) targeted to BCL6 rnRNA: Towards rational drug development for specific lymphoma subsets" Blood Cells, Molecules and Diseases 38: 199-203.

Kapadia et al., "Interference of Hepatitis C Virus RNA Replication by Short Interfering RNAs"; Proc. Natl. Acad. Sci. USA 100(4): 2014-2018 (2003).

(56) References Cited

OTHER PUBLICATIONS

Kawasaki et al., "Short Hairpin Type of dsRNAs that are Controlled by tRNAval Promoter Significantly Induce RNAi-mediated Gene Slicing in the Cytoplasm of Human Cells"; Nucleic Acids Research; 31(2): 700-707 (2003).
Kim et al., Interferon Induction by siRNAs and ssRNAs Synthesized by Phage Polymerase:; Nature Biotechnology, 22 (3): 321-325 (2004).
Kronke et al., "Alternative Approaches for Efficient Inhibition of Hepatitis C Virus RNA Replication by Small Interfering RNAs"; Journal of Virology; 78(7) 3436-3446 (2004).
Lagos-Quintana et al., "Identification of Novel Genes Coding for Small Expressed RNAs"; Science, 294: 853-858 (2001).
Lamontagne et al. Molecular requirements for duplex recognition and cleavage by eukaryotic RNase III: discovery of an RNA-dependent DNA cleavage activity of yeast Rntlp. J Mol Biol. Apr. 23, 2004;338(2):401-418.
Latham et al., "in RNA Interference Technology from Basic Science to Drug Development" Copyright (2005); Cambridge University Press, Chapter 10, pp. 153-154.
Layzer et al., "In Vivo Activity of Nuclease-Resistant siRNAs"; RNA, 10:776-771 (2004).
Li et al. Defining the optimal parameters for hairpin-based knockdown constructs. RNA. Oct. 2007;13(10):1765-1774.
Lieberman et al., "Interfering with Disease: Opportunities and Roadblocks to Harnessing RNA Interference"; Trends in Molecular Medicine; 9(9): 397-403 (2003).
Lin et al., "Assymetry of Intronic Pre-miRNA Structures in Functional RISC Assembly." Gene, Elsevier, Amsterdam, NL, 356: 32-38 (2005).
Ma et al., "Designing Ago2-specific siRNA/shRNA to avoid Competition with Endogenous miRNAs" Molecular Therapy-Nucleic Acids (2014) vol. 3 p. e176.
Marques et al., "A Structural Basis for Discriminating Between Self and Nonself Double-Stranded RNAs in Mammalian Cells"; Nature Biotechnology, 24(5): 559-565 (2006).
McCaffrey et al. (2003) "A potent and specific morpholino antisense inhibitor of hepatitis C translation in mice" Hepatology 38(2): 503-508.
McCaffrey et al., "Determinants of Hepatitis C Translational Initiation In Vitro, in Cultured Cells and Mice"; Molecular Therapy, 5(6): 676-684 (2002).
McCaffrey et al., "RNA Interference in Adult Mice"; Nature, 418:38-39 (2002).
McHutchison et al., "Future Therapy of Hepatitis C"; Hepatology, 36(5-S1): S245-S252 (2002).
McManus et al., "Gene silencing using micro-RNA designed hairpins" RNA (2002) 8:842-850.
Mercer et al., "Hepatitis C Virus Replication in Mice with Chimeric Human Livers"; Nature Medicine, 7(8): 927-933 (2001).
Nawrot, et al. Chemical and structural diversity of siRNA molecules. Curr Top Med Chem. 2006; 6:913-925.
Nishina, et al. Efficient In Vivo Delivery of siRNA to the Liver by Conjugation of alpha-Tocopherol. Mol Ther. 2008; vol. 16 No. 4, 734-740.
Ohta, Jun, RNAi Ni Kansuru Kisokenkyu to Sono Ouyou (Basic research on and application of RNA interference) Gan to Kagaku Ryouhou (Japanese Journal of Cancer and Chemotherapy) Jun. 2004, vol. 31, No. 6, pp. 827-831. (Partial translation attached).
Okamato et al., "Nucleotide Sequence of the Genomic RNA of Hepatitis C Virus Isolated from a Human Carrier: Comparison with Reported Isolates for Conserved and Divergent Regions"; J. Gen. Virol. 72(PT.11) 2697-2704 (1991) Abstract.
Paddison et al., "Short hairpin RNAs (shRNAs) induce sequence-specific silencing in mammalian cells" (2002) Genes & Dev. 16:948-958.
PCT/US2005/032768 International search report and written opinion dated Jul. 10, 2006.
PCT/US2005/032768 International report on patentability dated Mar. 13, 2007.
PCT/US2009/060712 International search report and written opinion dated Apr. 5, 2010.
PCT/US2009/060712 International report on patentability dated Apr. 19, 2011.
PCT/US2010/041782 International Preliminary Report on Patentability dated Jan. 26, 2012.
PCT/US2010/041782 International search report and written opinion dated Mar. 17, 2011.
PCT/US2006/021253 International Search Report dated Jun. 28, 2007 (3 pgs).
PCT/US2006/021253 International report on patentability dated Mar. 18, 2008.
Pietschmann et al., "Tissue Culture an Animal Modes for Hepatitis C Virus"; Clinics in Liver Disease, 7:23-43 (2003).
Qin et al., "Inhibiting HIV-1 Infection in Human T Cells by Lentiviral-Mediated Delivery of Small Interfering RNA Against CCR5"; Proc. Natl. Acad. Sci. USA 100(1): 183-188 (2003).
Radhakrishnan et al., "RNA Interferences as a New Strategy Against Viral Hepatitis"; Virology, 323: 173-181 (2004).
Randall et al., "Interfering with Hepatitis C Virus RNA Replication"; Virus Research, 102: 19-25 (2004).
Randall et al., "Clearance of Replicating Hepatitis C Virus Replicon RNAs in Cell Culture by Small Interfering RNAs"; Prof Natl. Acad. Sci. USA, 100(1): 235-240 (2003).
Rice, "Fresh Assault on Hepatitis C"; Nature, 426: 129-131 (2003).
Robbins et al. siRNA and innate immunity. Oligonucleotides. Jun. 2009;19(2):89-102.
Robbins et al., "Stable Expression of shRNAs in Human CD34+ Progenitor Cells can Avoid Induction of Interferon Responses to siRNAs In Vitro"; Nature Biotechnology, 24(5): 566-571 (2006).
Robbins, et al. 2'-O-methyl-modified RNAs act as TLR7 antagonists. Mol Ther. 2007; 15:1663-1669.
Sano et al. "Effect of Asymmetric Terminal Structures of Short RNA Duplexes on the RNA Interference Activity and Strand Selection." Nucleic Acids Research,36 (18): 5812-5821 (2008).
Sen et al., "Inhibition of Hepatitis C Virus Protein Expression by RNA Interferences"; Virus Research, 96: 27-35 (2003).
Seo et al., "Letter to the Editor: Small Interfering RNA-Mediated Inhibition of Hepatitis C Virus Replication in the Human Hepatoma Cell Line Huh-7"; Journal of Virology, 77(1): 810-812 (2003).
Seyhan et al., "Complete, Gene-Specific siRNA Libraries: Production and Expression in Mammalian Cells"; RNA, 11(5): 837-846 (2005).
Simmonds et al.. "Identification of genotypes of hepatitis C virus by sequence comparisons in the core, El and NS-5 regions" (1994) J. Gen._ Virol. 75:1053-1061.
Siolas et al., "Synthetic shRNAs as potent RNAi triggers" Nature Biotechnology (2005) 23(2): 227-231.
Sookoian, "New Therapies on the Horizon for Hepatitis C"; Annals of Hepatology, 2(4): 164-170 (2003).
Soutschek et al. Therapeutic silencing of an endogenous gene by systemic administration of modified siRNAs. Nature. 2004; 432:173-178.
U.S. Appl. No. 11/662,506 Office Action dated Jun. 2, 2010.
U.S. Appl. No. 11/662,506 Office Action dated Mar. 24, 2011.
U.S. Appl. No. 11/662,506 Office Action dated Oct. 26, 2009.
U.S. Appl. No. 12/597,323 Office Action dated Feb. 17, 2012.
U.S. Appl. No. 12/597,323 Office Action dated Sep. 6, 2011.
U.S. Appl. No. 13/039,100 Office Action dated Jun. 8, 2012.
U.S. Appl. No. 13/039,100 Office Action dated Oct. 15, 2012.
U.S. Appl. No. 13/384,201 Office Action dated Sep. 16, 2013.
U.S. Appl. No. 13/384,201 Office Action dated Dec. 12, 2013.
U.S. Appl. No. 13/384,201 Final Office Action dated Apr. 7, 2014.
U.S. Appl. No. 13/384,201 Notice of Allowance dated Jun. 20, 2014.
U.S. Appl. No. 13/591,433 Office Action dated Feb. 6, 2014.
U.S. Appl. No. 13/591,433 Office Action dated Oct. 8, 2013.
Vickers et al., "Efficient Reduction of Target RNAs by Small Interfering RNA and RNase H-dependent Antisense Agents" (2003), J. Biol. Chem 278: 7108-7118.
Vlassov et al., "shRNAs targeting hepatitis C: effects of sequence and structural features, and comparison with siRNA" Oligonucleotides (2007) 17:223-236.

(56) References Cited

OTHER PUBLICATIONS

Wang et al., "Small Hairpin RNAs Efficiently Inhibit Hepatitis C IRES-Mediated Gene Expression in Human Tissue Culture Cells and a Mouse Model"; Molecular Therapy, 12(3): 562-568 (2005).

Wilson et al., "RNA Interference Blocks Gene Expression and RNA Synthesis from Hepatitis C Replicons Propagated in Human Liver Cells"; Proc. Natl. Acad. Sci. USA, 100(5): 2783-2788 (2003).

Yokota et al., "Inhibition of Intracellular Hepatitis C Virus Replication by Synthetic and Vector-Derived Small Interfering RNAs"; EMBO Reports, 4(6): 602-608 (2003).

Yokota, Takanori. Gene therapy of virus disease with RNAi, Igaku No Ayumi (Journal of Clinical and Experimental Medicine), Feb. 21, 2004, vol. 208, No. 8, pp. 669-673. (Partial translation attached).

Yu et al, "RNA interference by expression of short-interfering RNAs and hairpin RNAs in mammalian cells" Proc. Natl. Acad. Sci. USA, 99(9):6047-6052 (Apr. 30, 2002).

Yu et al., "Simultaneous Inhibition of GSK3alpha and GSK3beta Using Hairpin siRNA Expression Vectors" Molecular Therapy, 7(2):228-236 (Feb. 2003).

Zhang , et al. RNA Interference with chemically modified siRNA. Curr Top Med Chem. 2006; 6:893-900.

Zhang et al., "Antisense Oligonucleotide Inhibition of Hepatitis C Virus (HCV) Gene Expression in Livers of Mice Infected with an HCV-Vaccinia Virus Recombinant"; Antimicrobial Agents and Chemotherapy, 43(2): 347-353 (1999).

Zhang et al., "Down-Regulation of Viral Replication by Adenoviral-Mediated Expression of siRNA Against Cellular Cofactors for Hepatitis C Virus"; Virology, 320: 135-143 (2004).

JP Application No. 211-532222 Office Action dated Feb. 18, 2015 (with English translation).

Chinese Application No. 200980149189.8 Office Action dated Sep. 11, 2015.

European Application No. 10800405.2-1401 Office Action dated Jan. 22, 2016.

Japanese Application No. 2015-122459 Office Action dated Apr. 4, 2016.

* cited by examiner

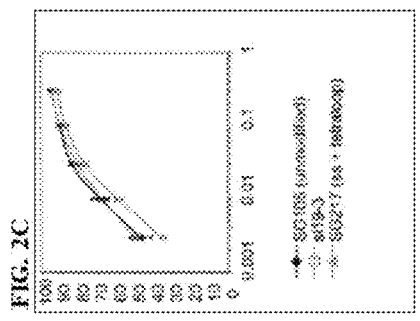
FIG. 2A
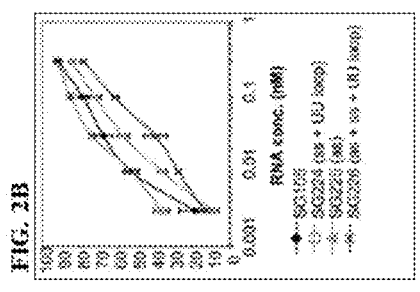
FIG. 2B
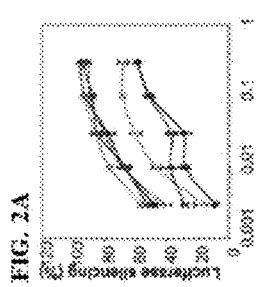
FIG. 2C
FIG. 2D
FIG. 2E

FIG. 5A
FIG. 5B
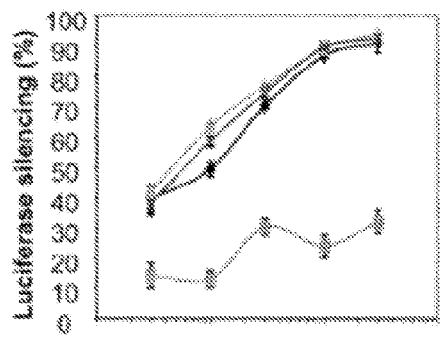
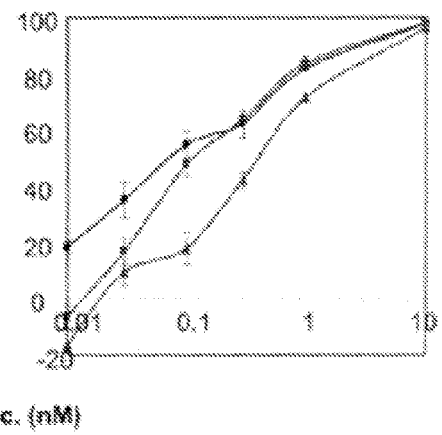
FIG. 5C
FIG. 5D
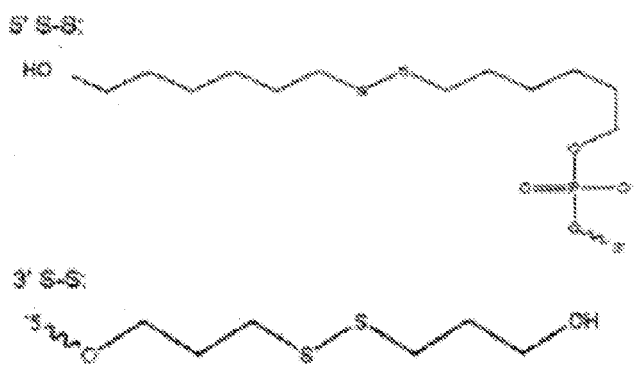
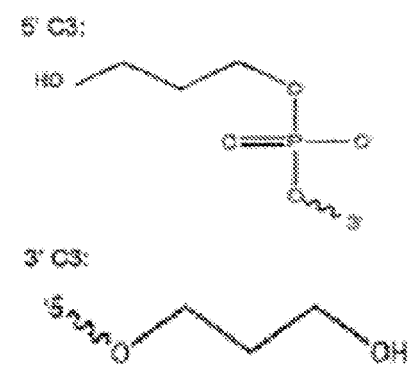

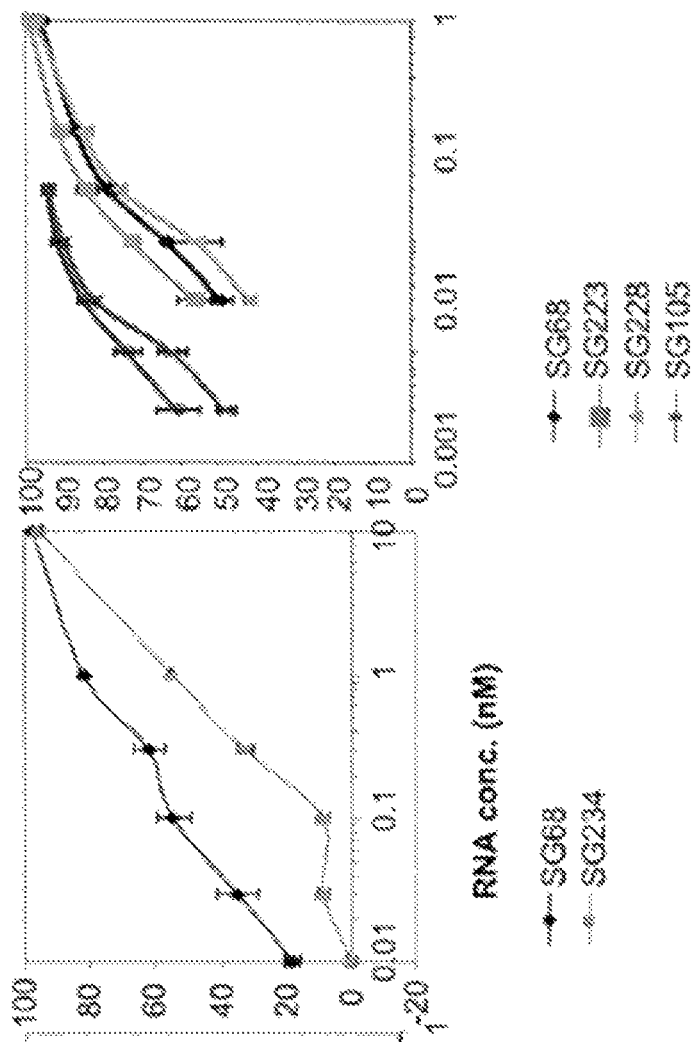
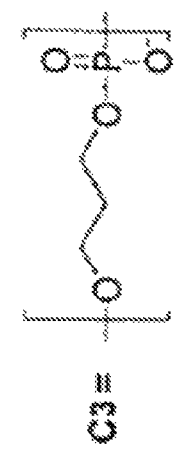
FIG. 6A, FIG. 6B, FIG. 6C

FIG. 15

```
                        SEQUENCE LISTING

<160> NUMBER OF SEQ ID NOS: 73

<210> SEQ ID NO 1
<211> LENGTH: 40
<212> TYPE: RNA
<213> ORGANISM: Artificial Sequence
<220> FEATURE:
<223> OTHER INFORMATION: Synthetic polynucleotide

<400> SEQUENCE: 1
ugagguuuag gauucgugcu ugcacgaauc cuaaaccuca                              40

<210> SEQ ID NO 2
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (7)..(40)

<400> SEQUENCE: 2
tgaggtuuag gauucgugcu ugcacgaauc cuaaaccuca                              40

<210> SEQ ID NO 3
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(34)

<400> SEQUENCE: 3
ugagguuuag gauucgugcu ugcacgaauc cuaaacctca                              40

<210> SEQ ID NO 4
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (7)..(34)

<400> SEQUENCE: 4
tgaggtuuag gauucgugcu ugcacgaauc cuaaacctca                              40

<210> SEQ ID NO 5
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (20)..(21)
<223> OTHER INFORMATION: um
```

```
<400> SEQUENCE: 5
ugagguuuag gauucgugcu ugcacgaauc cuaaaccuca                              40

<210> SEQ ID NO 6
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_difference
<222> LOCATION: (1)..(39)
<223> OTHER INFORMATION: 2'-O-methyl modified base at 1, 3, 5, 7, 9, 11,
      13, 15, 17, 23, 25, 27, 29, 31, 33, 35,37, 39
<220> FEATURE:
<221> NAME/KEY: misc_RNA
<222> LOCATION: (22)..(40)

<400> SEQUENCE: 6
ugagguuuag gauucgugct tgcacgaauc cuaaaccuca                              40

<210> SEQ ID NO 7
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_RNA
<222> LOCATION: (22)..(40)
<220> FEATURE:
<221> NAME/KEY: misc_difference
<222> LOCATION: (23)..(39)
<223> OTHER INFORMATION: 2'-O-methyl modified base at 23, 25, 27, 29,
      31, 33, 35, 37, 39

<400> SEQUENCE: 7
ugagguuuag gauucgugct tgcacgaauc cuaaaccuca                              40

<210> SEQ ID NO 8
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_difference
<222> LOCATION: (1)..(38)
<223> OTHER INFORMATION: 2'-O-methyl modified base at 1, 6, 8, 14, 17,
      29, 32, 38
<220> FEATURE:
<221> NAME/KEY: misc_RNA
<222> LOCATION: (22)..(40)

<400> SEQUENCE: 8
ugagguuuag gauucgugct tgcacgaauc cuaaaccuca                              40

<210> SEQ ID NO 9
<211> LENGTH: 40
<212> TYPE: DNA
<213> ORGANISM: Artificial Sequence
<220> FEATURE:
```

```
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_difference
<222> LOCATION: (1)..(39)
<223> OTHER INFORMATION: 2'-O-methyl modified base at 1, 3, 5, 7, 9,
      11, 13, 15, 17, 23, 25, 27, 29, 31, 33, 35,37, 39
<220> FEATURE:
<221> NAME/KEY: misc_RNA
<222> LOCATION: (22)..(40)

<400> SEQUENCE: 9
ugagguuuag gauucgugct tgcacgaauc cuaaaccuca                            40

<210> SEQ ID NO 10
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (19)..(39)
<223> OTHER INFORMATION: 2'-O-methyl modified base at 19, 21, 23, 25,
      27, 29, 31, 33, 35, 37, 39

<400> SEQUENCE: 10
ugagguuuag gauucgugcu ugcacgaauc cuaaaccuca                            40

<210> SEQ ID NO 11
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (20)..(39)
<223> OTHER INFORMATION: 2'-O-methyl modified base at 20, 21, 23, 25,
      27, 29, 33, 35, 37, 39

<400> SEQUENCE: 11
ugagguuuag gauucgugcu ugcacgaauc cuaaaccuca                            40

<210> SEQ ID NO 12
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (2)..(2)
<223> OTHER INFORMATION: gm

<400> SEQUENCE: 12
ugagguuuag gauucgugcu ugcacgaauc cuaaaccuca                            40

<210> SEQ ID NO 13
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (2)..(39)
<223> OTHER INFORMATION: 2'-O-methyl modified base at 2, 20, 21, 23, 25,
      27, 29, 31, 33, 35, 37, 39
```

-continued

<400> SEQUENCE: 13
ugagguuuag gauucgugcu ugcacgaauc cuaaaccuca                                   40

<210> SEQ ID NO 14
<211> LENGTH: 36
<212> TYPE: RNA
<213> ORGANISM: Artificial Sequence
<220> FEATURE:
<223> OTHER INFORMATION: Synthetic polynucleotide

<400> SEQUENCE: 14
ugagguuuag gauucgugca cgaauccuaa accuca                                      36

<210> SEQ ID NO 15
<211> LENGTH: 36
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (21)..(35)
<223> OTHER INFORMATION: 2'-O-methyl modified base at 21, 23, 25, 27,
      29, 31, 33, 35

<400> SEQUENCE: 15
ugagguuuag gauucgugca cgaauccuaa accuca                                      36

<210> SEQ ID NO 16
<211> LENGTH: 36
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (17)..(35)
<223> OTHER INFORMATION: 2'-O-methyl modified base at 17, 19, 21, 23,
      25, 27, 29, 31, 33, 35

<400> SEQUENCE: 16
ugagguuuag gauucgugca cgaauccuaa accuca                                      36

<210> SEQ ID NO 17
<211> LENGTH: 42
<212> TYPE: RNA
<213> ORGANISM: Artificial Sequence
<220> FEATURE:
<223> OTHER INFORMATION: Synthetic polynucleotide

<400> SEQUENCE: 17
auucgugcuc auggugcacu ugugcaccau gagcacgaau uu                                42

<210> SEQ ID NO 18
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (19)..(39)
<223> OTHER INFORMATION: 2'-O-methyl modified base at 19, 21, 23, 25,
      27, 29, 31, 33, 35, 37, 39

<400> SEQUENCE: 18
auucgugcuc auggugcacu ugugcaccau gagcacgaau                                  40

```
<210> SEQ ID NO 19
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(40)
<220> FEATURE:
<221> NAME/KEY: misc_difference
<222> LOCATION: (20)..(39)
<223> OTHER INFORMATION: 2'-O-methyl modified base at 20, 21, 23, 25,
      27, 29, 33, 35, 37, 39

<400> SEQUENCE: 19
auucgugcuc auggugcacu ugugcaccau gagcacgaau tt                           42

<210> SEQ ID NO 20
<211> LENGTH: 42
<212> TYPE: RNA
<213> ORGANISM: Artificial Sequence
<220> FEATURE:
<223> OTHER INFORMATION: Synthetic polynucleotide

<400> SEQUENCE: 20
uuuuucuuug agguuuaggu uccuaaaccu caaagaaaaa uu                           42

<210> SEQ ID NO 21
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (19)..(39)
<223> OTHER INFORMATION: 2'-O-methyl modified base at 19, 21, 23, 25,
      27, 29, 31, 33, 35, 37, 39

<400> SEQUENCE: 21
uuuuucuuug agguuuaggu uccuaaaccu caaagaaaaa                              40

<210> SEQ ID NO 22
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(40)
<220> FEATURE:
<221> NAME/KEY: misc_difference
<222> LOCATION: (23)..(39)
<223> OTHER INFORMATION: 2'-O-methyl modified base at 23, 39

<400> SEQUENCE: 22
auucgugcuc auggugcacu ugugcaccau gagcacgaau tt                           42

<210> SEQ ID NO 23
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(40)
```

```
<220> FEATURE:
<221> NAME/KEY: misc_difference
<222> LOCATION: (23)..(39)
<223> OTHER INFORMATION: 2'-O-methyl modified base at 23, 35, 37, 39

<400> SEQUENCE: 23
auucgugcuc auggugcacu ugugcaccau gagcacgaau tt                              42

<210> SEQ ID NO 24
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(40)
<220> FEATURE:
<221> NAME/KEY: misc_difference
<222> LOCATION: (23)..(39)
<223> OTHER INFORMATION: 2'-O-methyl modified base at 23, 25, 35, 37, 39

<400> SEQUENCE: 24
auucgugcuc auggugcacu ugugcaccau gagcacgaau tt                              42

<210> SEQ ID NO 25
<211> LENGTH: 45
<212> TYPE: RNA
<213> ORGANISM: Artificial Sequence
<220> FEATURE:
<223> OTHER INFORMATION: Synthetic polynucleotide

<400> SEQUENCE: 25
gcacgaaucc uaaaccucac aauaugaggu uuaggauucg ugcuu                           45

<210> SEQ ID NO 26
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (26)..(26)
<223> OTHER INFORMATION: gm

<400> SEQUENCE: 26
gcacgaaucc uaaaccucac aauaugaggu uuaggauucg ugcuu                           45

<210> SEQ ID NO 27
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (2)..(26)
<223> OTHER INFORMATION: 2'-O-methyl modified base at 2, 4, 6, 8, 10,
     12, 14, 16, 18, 26

<400> SEQUENCE: 27
gcacgaaucc uaaaccucac aauaugaggu uuaggauucg ugcuu                           45

<210> SEQ ID NO 28
<211> LENGTH: 45
<212> TYPE: RNA
<213> ORGANISM: Artificial Sequence
<220> FEATURE:
```

```
<223> OTHER INFORMATION: Synthetic polynucleotide
<220> FEATURE:
<221> NAME/KEY: misc_difference
<222> LOCATION: (2)..(18)
<223> OTHER INFORMATION: 2'-O-methyl modified base at 2, 4, 6, 8, 10,
      12, 14, 16, 18

<400> SEQUENCE: 28
gcacgaaucc uaaaccucac aauaugaggu uuaggauucg ugcuu                    45

<210> SEQ ID NO 29
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (1)..(39)
<223> OTHER INFORMATION: 3'-phosphorothioate bond at 1, 2, 38, 39

<400> SEQUENCE: 29
ugagguuuag gauucgugcu ugcacgaauc cuaaaccuca                          40

<210> SEQ ID NO 30
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_difference
<222> LOCATION: (1)..(39)
<223> OTHER INFORMATION: 3'-phosphorothioate bond at 1, 2, 38, 39
<220> FEATURE:
<221> NAME/KEY: misc_RNA
<222> LOCATION: (22)..(40)
<220> FEATURE:
<221> NAME/KEY: misc_difference
<222> LOCATION: (23)..(39)
<223> OTHER INFORMATION: 2'-O-methyl modified base at 23, 25, 27, 29,
      31, 33, 35, 37, 39

<400> SEQUENCE: 30
ugagguuuag gauucgugct tgcacgaauc cuaaaccuca                          40

<210> SEQ ID NO 31
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (1)..(1)
<223> OTHER INFORMATION: 5'-thiol linker modified terminal

<400> SEQUENCE: 31
ugagguuuag gauucgugcu ugcacgaauc cuaaaccuca                          40

<210> SEQ ID NO 32
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
```

-continued

<222> LOCATION: (40)..(40)
<223> OTHER INFORMATION: 3' thiol linker modified terminal

<400> SEQUENCE: 32
ugagguuuag gauucgugcu ugcacgaauc cuaaaccuca                            40

<210> SEQ ID NO 33
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (1)..(1)
<223> OTHER INFORMATION: 5'-C3 modified terminal

<400> SEQUENCE: 33
gcacgaaucc uaaaccucac aauaugaggu uuaggauucg ugcuu                      45

<210> SEQ ID NO 34
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (40)..(40)
<223> OTHER INFORMATION: 3'-C3 modified terminal

<400> SEQUENCE: 34
gcacgaaucc uaaaccucac aauaugaggu uuaggauucg ugcuu                      45

<210> SEQ ID NO 35
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_RNA
<222> LOCATION: (22)..(40)

<400> SEQUENCE: 35
ugagguuuag gauucgugct tgcacgaauc cuaaaccuca                            40

<210> SEQ ID NO 36
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(18)
<220> FEATURE:
<221> NAME/KEY: misc_difference
<222> LOCATION: (18)..(22)
<223> OTHER INFORMATION: 3'-phosphorothioate bond
<220> FEATURE:
<221> NAME/KEY: misc_RNA
<222> LOCATION: (23)..(40)

<400> SEQUENCE: 36
ugagguuuag gauucgugct tgcacgaauc cuaaaccuca                            40

```
<210> SEQ ID NO 37
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: n = C3 linker

<400> SEQUENCE: 37
ugagguuuag gauucgugcn ngcacgaauc cuaaaccuca                              40

<210> SEQ ID NO 38
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(23)
<223> OTHER INFORMATION: n = C3 linker

<400> SEQUENCE: 38
gcacgaaucc uaaaccucac annaugaggu uaggauucg ugcuu                         45

<210> SEQ ID NO 39
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (19)..(24)
<223> OTHER INFORMATION: 3'-phosphorothioate bond

<400> SEQUENCE: 39
gcacgaaucc uaaaccucac aauaugaggu uaggauucg ugcuu                         45

<210> SEQ ID NO 40
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(19)
<220> FEATURE:
<221> NAME/KEY: misc_difference
<222> LOCATION: (19)..(24)
<223> OTHER INFORMATION: 3'-phosphorothioate bond
<220> FEATURE:
<221> NAME/KEY: misc_RNA
<222> LOCATION: (25)..(45)

<400> SEQUENCE: 40
gcacgaaucc uaaaccucac aataugaggu uaggauucg ugcuu                         45

<210> SEQ ID NO 41
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
```

<222> LOCATION: (40)..(40)
<223> OTHER INFORMATION: 3'-thiol linker modified terminal

<400> SEQUENCE: 41
ugagguuuag gauucgugcu ugcacgaauc cuaaaccuca           40

<210> SEQ ID NO 42
<211> LENGTH: 40
<212> TYPE: RNA
<213> ORGANISM: Artificial Sequence
<220> FEATURE:
<223> OTHER INFORMATION: Synthetic polynucleotide

<400> SEQUENCE: 42
ugagguuuag gauucgugcu ugcacgaauc cuaaaccuca           40

<210> SEQ ID NO 43
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (26)..(28)
<223> OTHER INFORMATION: 3'-phosphorothioate bond

<400> SEQUENCE: 43
ugagguuuag gauucgugcu ugcacgaauc cuaaaccuca           40

<210> SEQ ID NO 44
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (29)..(31)
<223> OTHER INFORMATION: 3'-phosphorothioate bond

<400> SEQUENCE: 44
ugagguuuag gauucgugcu ugcacgaauc cuaaaccuca           40

<210> SEQ ID NO 45
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (32)..(34)
<223> OTHER INFORMATION: 3'-phosphorothioate bond

<400> SEQUENCE: 45
ugagguuuag gauucgugcu ugcacgaauc cuaaaccuca           40

<210> SEQ ID NO 46
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (30)..(30)
<223> OTHER INFORMATION: 3'-phosphorothioate bond
<220> FEATURE:

```
<221> NAME/KEY: modified_base
<222> LOCATION: (30)..(30)
<223> OTHER INFORMATION: cm

<400> SEQUENCE: 46
ugagguuuag gauucgugcu ugcacgaauc cuaaaccuca                           40

<210> SEQ ID NO 47
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (17)..(39)
<223> OTHER INFORMATION: 2'-O-methyl modified base at 17, 23, 25, 27,
      29, 33, 35, 37, 39

<400> SEQUENCE: 47
ugagguuuag gauucgugcu ugcacgaauc cuaaaccuca                           40

<210> SEQ ID NO 48
<211> LENGTH: 40
<212> TYPE: RNA
<213> ORGANISM: Artificial Sequence
<220> FEATURE:
<223> OTHER INFORMATION: Synthetic polynucleotide

<400> SEQUENCE: 48
ugagguuuag gauucgugcu ugcacgaaca agaaaccuca                           40

<210> SEQ ID NO 49
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_RNA
<222> LOCATION: (1)..(21)

<400> SEQUENCE: 49
ugagguuuag gauucgugcu ugcacgaatc ctaaacctca                           40

<210> SEQ ID NO 50
<211> LENGTH: 45
<212> TYPE: RNA
<213> ORGANISM: Artificial Sequence
<220> FEATURE:
<223> OTHER INFORMATION: Synthetic polynucleotide

<400> SEQUENCE: 50
gcacgaacaa gaaaccucac aauaugaggu uuaggauucg ugcuu                     45

<210> SEQ ID NO 51
<211> LENGTH: 45
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (9)..(9)
<223> OTHER INFORMATION: cm
<220> FEATURE:
<221> NAME/KEY: misc_difference
<222> LOCATION: (9)..(9)
<223> OTHER INFORMATION: 3'-phosphorothioate bond
```

-continued

<400> SEQUENCE: 51
gcacgaaucc uaaaccucac aauaugaggu uuaggauucg ugcuu         45

<210> SEQ ID NO 52
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 52
ugagguuuag gauucgugcu u                                   21

<210> SEQ ID NO 53
<211> LENGTH: 21
<212> TYPE: RNA
<213> ORGANISM: Artificial Sequence
<220> FEATURE:
<223> OTHER INFORMATION: Synthetic polynucleotide

<400> SEQUENCE: 53
gcacgaaucc uaaaccucau u                                   21

<210> SEQ ID NO 54
<211> LENGTH: 20
<212> TYPE: DNA
<213> ORGANISM: Artificial Sequence
<220> FEATURE:
<223> OTHER INFORMATION: Synthetic primer

<400> SEQUENCE: 54
tcccaagcct tcaacgactg                                     20

<210> SEQ ID NO 55
<211> LENGTH: 22
<212> TYPE: DNA
<213> ORGANISM: Artificial Sequence
<220> FEATURE:
<223> OTHER INFORMATION: Synthetic primer

<400> SEQUENCE: 55
tggtgaagga gagctatcca ca                                  22

<210> SEQ ID NO 56
<211> LENGTH: 23
<212> TYPE: DNA
<213> ORGANISM: Artificial Sequence
<220> FEATURE:
<223> OTHER INFORMATION: Synthetic primer

<400> SEQUENCE: 56
ttacctggat ggaaaccagc tac                                 23

<210> SEQ ID NO 57
<211> LENGTH: 24
<212> TYPE: DNA
<213> ORGANISM: Artificial Sequence
<220> FEATURE:
<223> OTHER INFORMATION: Synthetic primer

<400> SEQUENCE: 57
tcaaggctga gaagctgtaa gcta                                24

<210> SEQ ID NO 58

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 58
gagagccgag acaaaaacgt tc                                              22

<210> SEQ ID NO 59
<211> LENGTH: 19
<212> TYPE: DNA
<213> ORGANISM: Artificial Sequence
<220> FEATURE:
<223> OTHER INFORMATION: Synthetic primer

<400> SEQUENCE: 59
tgtcgatgat ggccaatcc                                                  19

<210> SEQ ID NO 60
<211> LENGTH: 18
<212> TYPE: DNA
<213> ORGANISM: Artificial Sequence
<220> FEATURE:
<223> OTHER INFORMATION: Synthetic primer

<400> SEQUENCE: 60
cagtatattc aggctgag                                                   18

<210> SEQ ID NO 61
<211> LENGTH: 17
<212> TYPE: DNA
<213> ORGANISM: Artificial Sequence
<220> FEATURE:
<223> OTHER INFORMATION: Synthetic primer

<400> SEQUENCE: 61
ggccagtttt ccttgtc                                                    17

<210> SEQ ID NO 62
<211> LENGTH: 25
<212> TYPE: DNA
<213> ORGANISM: Artificial Sequence
<220> FEATURE:
<223> OTHER INFORMATION: Synthetic primer

<400> SEQUENCE: 62
tctgactacc tgtcctctgg ttctt                                           25

<210> SEQ ID NO 63
<211> LENGTH: 22
<212> TYPE: DNA
<213> ORGANISM: Artificial Sequence
<220> FEATURE:
<223> OTHER INFORMATION: Synthetic primer

<400> SEQUENCE: 63
gcgagtgtgc tggtcactaa ag                                              22

<210> SEQ ID NO 64
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
```

```
<222> LOCATION: (15)..(39)
<223> OTHER INFORMATION: 2'-O-methyl modified base at 15, 17, 23, 25,
      27, 29, 33, 35, 37, 39

<400> SEQUENCE: 64
ugagguuuag gauucgugcu ugcacgaauc cuaaaccuca                    40

<210> SEQ ID NO 65
<211> LENGTH: 25
<212> TYPE: RNA
<213> ORGANISM: Artificial Sequence
<220> FEATURE:
<223> OTHER INFORMATION: Synthetic polynucleotide

<400> SEQUENCE: 65
gagcacgaau ccuaaaccuc aaaga                                    25

<210> SEQ ID NO 66
<211> LENGTH: 40
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (23)..(39)
<223> OTHER INFORMATION: 2'-O-methyl modified base at 23, 25, 27, 29,
      33, 35, 37, 39

<400> SEQUENCE: 66
cgugcuuagg auuggaguu uacuccaaau ccuaagcacg                     40

<210> SEQ ID NO 67
<211> LENGTH: 30
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (23)..(29)
<223> OTHER INFORMATION: 2'-O-methyl modified base at 23, 25, 27, 29

<400> SEQUENCE: 67
ugagguuuag gauucgugcu ugcacgaauc                               30

<210> SEQ ID NO 68
<211> LENGTH: 30
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_difference
<222> LOCATION: (13)..(29)
<223> OTHER INFORMATION: 2'-O-methyl modified base at 13, 15, 17, 19,
      23, 25, 27, 29

<400> SEQUENCE: 68
gauucgugcu ugcacgaauc cuaaaccuca                               30

<210> SEQ ID NO 69
<211> LENGTH: 42
<212> TYPE: RNA
<213> ORGANISM: Artificial Sequence
<220> FEATURE:
<223> OTHER INFORMATION: Synthetic polynucleotide

<400> SEQUENCE: 69
```

```
gcacgaaucc uaaaccucau uugagguuua ggauucgugc uu                    42

<210> SEQ ID NO 70
<211> LENGTH: 38
<212> TYPE: RNA
<213> ORGANISM: Artificial Sequence
<220> FEATURE:
<223> OTHER INFORMATION: Synthetic polynucleotide

<400> SEQUENCE: 70
gcacgaaucc uaaaccuuga gguuuaggau ucgugcuu                         38

<210> SEQ ID NO 71
<211> LENGTH: 26
<212> TYPE: DNA
<213> ORGANISM: Artificial Sequence
<220> FEATURE:
<223> OTHER INFORMATION: Synthetic primer

<400> SEQUENCE: 71
cgcgcccaac accggcataa agaatt                                      26

<210> SEQ ID NO 72
<211> LENGTH: 25
<212> TYPE: DNA
<213> ORGANISM: Artificial Sequence
<220> FEATURE:
<223> OTHER INFORMATION: Synthetic primer

<400> SEQUENCE: 72
gcttctgcca accgaacgga cattt                                       25

<210> SEQ ID NO 73
<211> LENGTH: 23
<212> TYPE: DNA
<213> ORGANISM: Artificial Sequence
<220> FEATURE:
<223> OTHER INFORMATION: Synthetic primer

<400> SEQUENCE: 73
cgactggagc acgaggacac tga                                         23
```

CHEMICAL MODIFICATION OF SHORT SMALL HAIRPIN RNAS FOR INHIBITION OF GENE EXPRESSION

CROSS REFERENCE

This application is the continuation of U.S. application Ser. No. 13/384,201, filed on Mar. 8, 2012, which is the National Phase entry of International Application No. PCT/US2010/041782, filed Jul. 13, 2010, which claims the benefit of priority of U.S. Provisional Application No. 61/225,136, filed on Jul. 13, 2009, the contents of each are incorporated by reference herein in their entireties.

STATEMENT REGARDING FEDERALLY SPONSORED RESEARCH

This invention was made in part during work supported by NIH grant R44AI056611 (BHJ) and 1R43AI074256 (BHJ) from the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 10, 2014, is named 40220-706.831-SeqListing.txt and is 19 Kilobytes in size.

FIELD OF THE INVENTION

The invention relates to chemical modification of RNAi agents (e.g., shRNAs) that find use in inhibiting gene expression, e.g., inhibition of viral gene expression.

BACKGROUND OF THE INVENTION

RNA interference (RNAi) is an evolutionarily conserved mechanism whereby microRNAs and other double-stranded RNA molecules effect sequence-specific gene regulation. RNAi has been heavily used as a tool to manipulate gene expression in vitro as well as in vivo. Its potential as a therapeutic approach is also widely studied (Elbashir et al. 2001; Xia et al. 2002; Dorsett and Tuschl 2004; Xia et al. 2004; Harper et al. 2005; Amarzguioui et al. 2006; Behlke 2006; Bernards et al. 2006; Chang et al. 2006; Fewell and Schmitt 2006; Vlassov et al. 2006). Multiple RNA structures can be used to perform RNAi, including siRNAs, Dicer-substrate RNAs, long dsRNAs, small hairpin RNAs (shRNAs) either in synthetic or expressed form. Among synthetic RNAi triggers, we and others have found a special class of shRNA, short shRNAs (sshRNA) that have identical, or in some cases, slightly better efficacy than siRNAs that target the same sequences (Li et al. 2007; Vlassov et al. 2007; and U.S. Provisional Patent Application Ser. No. 61/105,606, filed Oct. 15, 2008, all of which are incorporated herein by reference in their entirety). As described therein, sshRNAs have a stem length of 19 bp or less (where the stem is formed from sense and antisense sequences for the target RNA of interest), a connection of 0 to 9 nt between the antisense and the sense sequence, and optionally a 1 to 2-base 3'-overhang. The connection (also called a loop) is sometimes preferred at the 3' end of the antisense sequence (L sshRNAs) as opposed to being at the 3' end of the sense sequence (R sshRNAs) for better RNAi activity (McManus et al. 2002; Harborth et al. 2003).

To promote in vivo applications of synthetic sshRNAs, several factors should be considered, including 1) the nuclease stability of RNA duplexes in biological fluids such as serum; 2) the delivery and cellular uptake of the RNA duplex with sufficient cell specificity and efficiency; 3) minimal undesired innate immune responses; 4) minimal off-target effects. For instance, various results have demonstrated the ability of synthetic siRNAs and shRNAs to activate mammalian immune responses (Kariko et al. 2004; Kim et al. 2004; Hornung et al. 2005; Judge et al. 2005; Sioud 2005; Marques et al. 2006; Schlee et al. 2006; Judge and MacLachlan 2008; Robbins et al. 2008, incorporated herein by reference in their entirety). Toll-like receptors (TLR3, TLR7, and TLR8), protein kinase R (PKR), the cytosolic RNA helicase retinoic acid-inducible gene (RIG-I) and melanoma differentiation-associated gene 5 (MDA-5) are involved in the synthetic RNAi molecule-mediated recognition and activation of the innate immune response (Judge and MacLachlan 2008) (incorporated herein by reference in its entirety). Several features of RNA, including length, sequence, and structure could account for the recognition by these receptors (Hornung et al. 2005; Judge et al. 2005; Forsbach et al. 2008), (incorporated herein by reference in their entirety). Although some level of inflammatory cytokine expression may be beneficial to antiviral or even anti-tumor therapeutics (Poeck et al. 2008) (incorporated herein by reference in its entirety), the toxicities associated with excessive cytokine release and associated inflammatory syndromes are an undesirable side-effect.

Small synthetic RNAs (such as siRNA and shRNA) that exploit the naturally existing RNA interference mechanism normally used by endogenous microRNAs are potent agents for controlling gene expression in human cells. To translate this potency into therapeutics, it is necessary to optimize the efficacy of the RNA-based drugs. Besides selecting effective RNA sequences, the optimization includes chemical modifications to improve their in vivo nuclease stability, cellular delivery, biodistribution, pharmacokinetics, potency, and specificity while reducing off-target effects and immune response. Various chemical modifications, most of which were originally developed for ribozymes and RNA aptamers, have been proposed in issued and pending patent applications for siRNAs (e.g. in U.S. Pat. No. 7,595,387; WO2004090105; US20060247428; US20070167384; US20070167393; US20090209626) as well as for synthetic (vs. unmodified vector-expressed) shRNAs (WO03070750; WO2004015075; US20040209831; US20060223777; US20070004665; U.S. Pat. No. 7,595,387). The modified siRNA and shRNA molecules include various modifications of sugar, internucleotide phospodiester bonds, purine and pyrimidine residues, as well as non-nucleotide links, bridges, loops and conjugates (Manoharan 2004; Corey 2007; Behlke, 2008; Watts et al. 2008; Shukla et al. 2010).

The future success of RNA-based drugs relies on the identification of appropriate chemical modifications placed at appropriate positions in these RNAs. Because of a lack of a clear mechanistic understanding of the effect of different modifications on messenger RNA (mRNA) silencing mediated by the RNA-induced silencing complex (RISC) (Skulka et al. 2010), there are not general rules for optimization of RNA-drugs. The effect of particular modifications strongly depends on the sequence and size of RNA drugs. For example, double-stranded RNA molecules acting through different pathways (e.g. acting either as Dicer or non-Dicer substrates) require different modification strategies (see, e.g., Pavco et al. WO2009102427A2). Similarly, short shRNAs (sshRNAs) cannot be processed by Dicer in contrast to ordinary shRNAs, and, therefore, must be processed by a Dicer-independent mechanism (Cifuentes et al. 2010). The difference between the mechanisms of nuclease-assisted processing of ordinary shRNAs and the sshRNAs requires different modification patterns, which do not interfere with the latter mechanism. Because of this difference in mechanism, the specific patterns for modifications of sshRNAs are not predictable based on the prior art.

SUMMARY OF THE INVENTION

The present invention is directed to methods and compositions pertaining to chemical modification of shRNA for use in gene silencing, e.g., for therapeutic applications. Accordingly, the present invention provides compositions, methods, and kits for increasing the efficiency, specificity, and stability of RNA interference using modified shRNAs.

Aspects of the invention include small hairpin RNAs (shRNAs) comprising a chemical modification that results in reduced immunostimulatory activity, increased serum stability, or both, as compared to a corresponding RNA molecule not having the chemical modification.

In certain embodiments, shRNAs of the invention include an antisense sequence of about 16 to about 19 nucleotides; a sense sequence having from about 11 to about 19 nucleotides; and a loop region connecting the antisense and sense sequences. The sense sequence is substantially complementary to the antisense sequence, forming a stem structure in the shRNA when annealed intramolecularly. The shRNA includes at least one of the following chemical modifications: 2'-H, 2'-O-methyl, or 2'-OH modification of one or more nucleotides; one or more phosphorothioate modifications of the backbone; and/or a non-nucleotide moiety in the loop region. As noted, the chemical modification(s) confer reduced immunostimulatory activity, increased serum stability, or both, as compared to a corresponding shRNA not having the chemical modification.

In certain embodiments, the pyrimidine nucleotides in the sense region or the loop region comprise 2'-O-methylpyrimidine nucleotides and/or 2'-deoxy-pyrimidine nucleotides.

In certain embodiments, some or all of the purine nucleotides in the sense region or the loop region can comprise 2'-O-methylpurine nucleotides and/or 2'-deoxy-purine nucleotides.

In certain embodiments, the chemical modification is present in positions 15-19 of the antisense sequence.

In certain embodiments, the chemical modification is present in nucleotides proximal to the 3' and/or 5' ends of the shRNA.

An shRNA according to aspects of the invention may include: 2'-O-Methy groups at every other nucleotide in the sense sequence (the passenger strand) except nucleotides 9, 10 and 11; and 2'-deoxy or 2'-O-Me at every nucleotide of the loop region. The shRNA may further comprises a 2'-O-Methyl group at one or more of nucleotides 15, 17, and 19 of the antisense sequence (the guide strand). In certain embodiments, the shRNA further comprises an overhang region ranging from 1 to 10 nucleotides on the first region or the second region.

Embodiments of the invention also include L shRNAs with a blunt end and a loop region having either a dTdT loop, a rUrU loop, or a non-nucleotide loop having a length equivalent to 2 nucleotides.

Embodiments of the invention also include R shRNA with an overhang region at the 3' end of 2 nucleotides in length that has a chemical modification selected from a 2'-deoxy-nucleotide, a 2'-O-methylated nucleotide or a phosphorothioate linkage. The loop region of such R shRNAs may be selected from a 2 nucleotide dTdT loop, a 2 nucleotide rUrU loop, or a non-nucleotide loop having a length equivalent to 2 nucleotides.

Modified shRNAs may include sense and antisense sequences that are 18 or 19 nucleotides in length and are 100% complementary.

In certain embodiments, the shRNA is a short shRNA (sshRNA) ranging in length from 28 to 44 nucleotides.

In certain embodiments, the chemically modified shRNA retains at least 50% RNAi activity in a gene expression inhibition assay as compared to the corresponding RNA molecule not having the chemical modification.

In certain embodiments, wherein the shRNA has reduced immunostimulatory activity, wherein the reduced immunostimulatory activity is selected from the group consisting of: reduced induction of type I interferon (IFN), reduced induction of interferon (IFN) beta, reduced induction of interleukin-6 (IL-6), reduced induction of tumor necrosis factor alpha (TNF-alpha), reduced induction of Toll like receptors (TLRs), reduced induction of proinflammatory cytokines, reduced induction of innate immune responsive genes, reduced induction of protein kinase R (PKR), reduced induction of retinoic acid-inducible gene (RIG-I), and any combination thereof. In certain embodiments, the TLR is selected from TLR3, TLR7, and TLR8.

shRNAs as described herein may include from 2% to 65% of chemically modified nucleotides. The shRNA may include from 1 to 10 phosphorothioate internucleotide linkages at the 5' end, 3' end, and/or loop region.

In certain embodiments, an shRNA may include a conjugate moiety attached to the 5' end, 3' end, or loop region, wherein the conjugate moiety is optionally attached via a linker. The conjugate moiety may be selected from the group consisting of: a steroid, cholesterol, cholestanol, stigmasterol, cholanic acid, ergosterol, a vitamin, a peptide, a protein, galactose and derivatives thereof, and combinations thereof. For example, the conjugate moiety may be cholesterol attached via a C5 linker molecule. In certain embodiments, the conjugate moiety is vitamin E.

The shRNA may further include a detectable label attached to the loop region or terminus. In certain embodiments, the detectable label is a dye molecule, e.g., a fluorescent dye. In certain embodiments, the shRNA comprises a conjugate moiety and a detectable label.

The shRNA may be designed to be specific for a viral gene sequence, e.g., a hepatitis C viral gene sequence, or the internal ribosome entry site (IRES) sequence of hepatitis C virus.

In certain embodiments, the shRNA is selected from any one of SEQ ID NOs: 11, 37, 7, 1, 43, 29, 15, 30, 5, 32, 3, 45, 16, 36, 10, 35, 44, 4, 20, 2, 39, 17, 6, 12, 19, 24, 18, 9, 25, 23, 26, 13, 27, 38, 22, 41, 51, 46, 14, 33.

In certain embodiments, the modified RNA molecule has increased serum stability, e.g., having more than 50% of RNA molecules remain intact for 6 hours upon incubation with 10% human serum at 37° C.

Aspects of the present invention include compositions comprising: a chemically modified shRNA having reduced immunostimulatory activity, increased serum stability, or both, as compared to a corresponding RNA molecule not having the chemical modification (as described above); and a pharmaceutically acceptable carrier or excipient.

Aspects of the present invention include methods of inhibiting the expression of a target gene in a cell comprising contacting the cell with an shRNA specific for the gene, wherein the shRNA comprises a chemical modification, wherein the chemically modified shRNA has reduced immunostimulatory activity, increased serum stability, or both, as compared to a corresponding RNA molecule not having the chemical modification.

In certain embodiments, the cell can be in a mammal (in vivo), e.g., a human or a non-human primate. In certain embodiments, the contacting is in vitro.

Aspects of the present invention include methods for treating a subject for an infectious disease, an inflammatory disease, or a cancer, the method comprising administering to the subject a modified sshRNA according to the invention or a pharmaceutical composition according to the invention to a patient in need thereof.

In certain embodiments, the method is drawn to inhibiting expression or activity of a hepatitis C virus, the method comprising contacting a cell that expresses a hepatitis C virus with an RNA molecule described herein, wherein the first RNA sequence is at least partially complementary to a hepatitis C viral sequence.

In certain embodiments, the chemically modified shRNA retains at least 50% RNAi activity as compared to the corresponding RNA molecule not having the chemical modification.

In certain embodiments, the method is for treating an infectious disease, an inflammatory disease, or a cancer in a subject.

Aspects of the present invention include methods of producing an shRNA having reduced immunostimulatory activity, increased serum stability, or both, the method comprising: fabricating the shRNA such that a nucleotide is chemically modified, wherein the fabricated shRNA has reduced immunostimulatory activity, increased serum stability, or both, as compared to a corresponding RNA molecule not having the chemical modification.

Aspects of the present invention include methods of modifying an shRNA molecule having immunostimulatory properties, the method comprising: modifying the shRNA by substituting at least two nucleotides in the sense sequence with modified nucleotides, thereby generating a modified shRNA that is less immunostimulatory than the unmodified shRNA sequence, wherein the modified shRNA is capable of reducing or silencing the expression of its cognate target sequence.

In certain embodiments, the chemically modified shRNA retains at least 50% RNAi activity in a gene expression inhibition assay as compared to the corresponding RNA molecule not having the chemical modification.

Aspects of the present invention include methods of identifying and modifying an shRNA having immunostimulatory properties, the method comprising: (1) contacting an unmodified shRNA sequence with a mammalian responder cell under conditions suitable for the responder cell to produce a detectable immune response; (2) identifying the unmodified shRNA sequence as an immunostimulatory shRNA by the presence of a detectable immune response in the responder cell; and (3) modifying the immunostimulatory shRNA by substituting at least two nucleotides with modified nucleotides, thereby generating a modified shRNA sequence that is less immunostimulatory than the unmodified RNA sequence.

Aspects of the present invention include kits for inhibiting expression of a target gene in a cell, the kit comprising an shRNA specific for the target gene, wherein the shRNA includes a chemical modification that results in reduced immunostimulatory activity, increased serum stability, or both, as compared to a corresponding RNA molecule not having the chemical modification.

In certain embodiments, the kit comprises a reduced serum tissue culture medium.

Other aspects of the present invention will be apparent from the description below and the appended claims.

The following figures are presented for the purpose of illustration only, and are not intended to be limiting.

BRIEF DESCRIPTION OF THE DRAWINGS

FIG. 2 (panels A to E) depicts the dose response of L sshRNAs with 2'-O-methyl modification at various positions (see Example 2). The target sequence of these L sshRNAs was the same as that of si19-3 described in FIG. 1. The experiments were done as described in FIG. 1. FIGS. 2A-2C compare the potency of L sshRNA with and without 2'-OMe modification at the sense, antisense, both strands, or/and loop. The results suggest that the efficacy of L sshRNA was significantly reduced when more than one 2'-O-methyl ribosyl was substituted in the antisense sequence whereas 2'-OMe modification in the sense sequence (as many as 9 2'-O-methyl ribosyl substitutions at alternating positions) or the dinucleotide UU loop did not affect the activity. FIG. 2D depicts the potency of the modified derivatives of a special L sshRNA that contain a direct connection of a 19-nt antisense sequence and a 17-nt sense sequence. Again, two 2'-OMe ribosyl substitutions in the 3' end of the antisense sequence (forming the connection loop with the sense sequence) slightly affect the efficacy of the hairpin whereas the 2'-OMe modification in the sense sequence only did not exhibit negative effect on RNAi activity. FIG. 2E depicts the activity of sshRNAs with 2'-O-Me modification at positions 15 and 17 of the guide strand. The dose response of sshRNAs with guide strand 2'-O-Me modification at position 17 (SG242), and at both positions 15 and 17 (SG243) were compared with an sshRNA lacking guide strand modifications (SG224). All sshRNAs contained the same passenger strand and loop modifications. SG221(c) was included as a non-specific control. Modification at positions 15 and 17 reduced silencing slightly but these molecules were still potent inhibitors of luciferase expression.

FIG. 3 compare the dose response of L and R sshRNAs with 2'-O-methyl modification at various positions (see Example 2).

FIG. 5 depicts the potency of sshRNAs with and without end conjugations (see Example 5). FIG. 5A, L sshRNAs; FIG. 5B, R sshRNAs. The results indicate that 5'-end but not 3'-end conjugation significantly decrease the potency of L sshRNAs. However, R sshRNAs' activity is significantly decreased when the conjugation is placed at the 3'-end. FIG. 5C shows the structures of the 5'S—S and 3'S—S conjugates employed in FIG. 5A. FIG. 5D shows the structures of the 5' C3 and 3' C3 conjugates employed in FIG. 5B.

FIG. 6 compares the potency of sshRNAs with and without modifications in the hairpin loop (see Example 6). FIG. 6A-B shows the dose response of L (A) and R (B) sshRNAs with and without phosphorothioate bonds and deoxynucleotides in the entire loop. FIG. 6C shows the dose response of L and R sshRNAs with nonnucleotidic linkers in the loop. Since nonnucleotidic linkers or phosphorothioate bonds between deoxynucleotides block the cleavage by RNase such as Dicer, the low efficacy found in R sshRNA SG234 but not in SG228 indicates that cleavage at certain position in the loop is required for the efficient loading of R sshRNA to Ago2-containing RISC. However, no activity loss was found in L sshRNAs when the loop was highly resistant to cleavage.

FIG. 15 depicts the in vivo efficacy of modified shRNAs (see Example 16). An expression plasmid with the HCV-f-Luc fusion gene driven by a liver-specific promoter was introduced into mice by hydrodynamic injection, which efficiently targets expression to the liver. Seven days later, the formulated shRNA SG224 was administered by a low-pressure injection into the tail vein (Day 0). On subsequent days, mice were imaged for luciferase expression by in vivo bioluminescence. The left-hand four groups (5 mice each) received increasing amounts of active HCV-shRNA (left to right: 0.1, 0.5, 2.5, and 5.0 mg/kg. The next two groups received a similarly modified scrambled control shRNA (0.1 and 5 mg/kg). The last two groups received a saline injection or no treatment, respectively. Bars within each group correspond to (1 to r) day 0 (just prior to injection of shRNAs), day 1, day 2, day 3, day 4, day 8, day 14, and day 21. Error bars represent standard error of the mean.

DETAILED DESCRIPTION OF THE INVENTION

Figure 1:
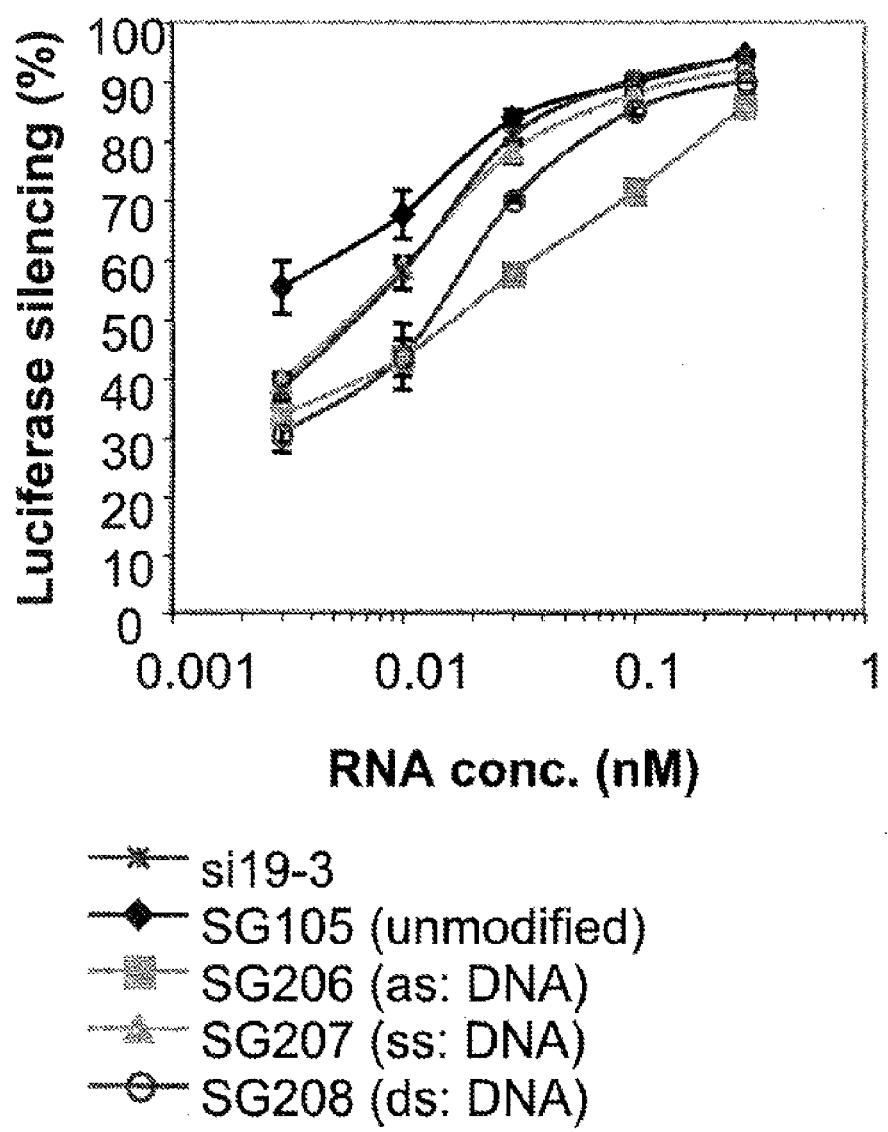
FIG. 1 compares the dose response of L sshRNAs having deoxynucleotides in the opening ends of the antisense, sense, or both strands (see Example 1). Results demonstrated that DNA substitution in the antisense sequence reduced the target knockdown activity of sshRNAs whereas DNA in the sense sequence did not affect the activity.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed. In addition, the materials, methods, and examples are illustrative only and not intended to be limiting.

Embodiments of the present disclosure are directed to compositions and methods for performing RNA-induced gene silencing (also called RNAi). As detailed herein, specific modifications to an sshRNA (an RNAi agent) leads to improved function in reducing gene expression in a target cell (e.g., in vitro or in vivo, e.g., in a subject). In certain embodiments, the modified sshRNA agent has improved stability, e.g., in serum, and/or reduced immunostimulatory activity. Accordingly, the present disclosure provides compositions, methods, and kits for increasing the functionality and specificity of sshRNAs. Aspects of the present invention include compositions and methods for improving the functionality and specificity of sshRNAs for inhibiting viral gene expression and/or treating a viral infection in a mammal, such as a human. In some embodiments, the sshRNA constructs described herein inhibit gene expression of a virus by inducing cleavage of viral polynucleotide sequences within or near the target sequence that is recognized by the antisense sequence of the sshRNA.

The phrase "small hairpin RNA" and the term "shRNA", as used herein, refer to a unimolecular RNA-containing polynucleotide that is capable of performing RNAi and that includes a sense sequence, a loop, and an antisense sequence. The sense and antisense sequences are sometimes referred to herein as the first region and second region. As described herein, the sense and antisense sequences can be in different orientations with respect to one another in an shRNA of the invention (an L or R shRNA). Thus, if the first region of an shRNA is the sense sequence then the second region is the antisense region, and vice versa. Preferably, the sense and antisense sequences are substantially complementary to each other (about 80% complementary). The antisense sequence can be about 16 to about 22 nucleotides in length, e.g., about 16 to 19 nucleotides, and more preferably 18 to 19 nucleotides in length. The sense sequence can be about 11 to about 22 nucleotides in length, and more preferably 17 to 19 nucleotides in length. An shRNA (and other RNAi agents) are "specific" for a target gene when the antisense sequence (of about 16 to 22 nucleotides is substantially complementary to the target gene (or target RNA, e.g., target mRNA). By substantially complementary is meant that the antisense sequence is at least 80% complementary to the target gene (or gene product). Thus, in some embodiments, the antisense sequence that is complementary to the target gene can contain mismatches to the target. The sequence can be varied to target one or more genetic variants or phenotypes of a target, e.g., a viral target, by altering the targeting sequence to be complementary to the sequence of the genetic variant or phenotype. In some embodiments, a sequence can target multiple viral strains, e.g., of HCV, although the sequence can differ from the target of a strain by at least one nucleotide (e.g., one, two, or three nucleotides) of a targeting sequence. An shRNA may have a loop as long as, for example, 0 to about 24 nucleotides in length, preferably 0 to about 10 nucleotides in length, 0 to 6 nucleotides in length, e.g., 2 nucleotides in length. The sequence of the loop can include nucleotide residues unrelated to the target. In one particularly preferred embodiment, the loop is 5'-UU-3'. In some embodiments it may include non-nucleotide moieties. In yet other embodiments, the loop does not include any non-nucleotides moieties. Optionally, the shRNA can have an overhang region of 2 bases on 3' end of the molecule. The shRNA can also comprise RNAs with stem-loop structures that contain mismatches and/or bulges. The sense sequence that is homologous to the target can differ at about 0 to about 5 sites by having mismatches, insertions, or deletions of from about 1 to about 5 nucleotides, as is the case, for example, with naturally occurring microRNAs. RNAs that comprise any of the above structures can include structures where the loops comprise nucleotides, non-nucleotides, or combinations of nucleotides and non-nucleotides.

In some embodiments, an shRNA described herein is a "short shRNA", or "sshRNA", which term comprises shRNAs having stem lengths of 19 or fewer nucleotides, loops of any size, and optionally a 3' extension.

Additionally, the term "L shRNA" refers to an shRNA comprising a sense sequence that is connected through a loop to the 3' end of the antisense.

Additionally, the term "R shRNA" refers to an shRNA molecule comprising an antisense sequence that is connected through a loop to the 3' end of the sense sequence.

In some embodiments, an shRNA described herein optionally includes at least one conjugate moiety.

The shRNAs described herein can be useful in implementing gene silencing. Also, they may be preferred over duplexes having lengths that are similar or equivalent to the length of the stem of the hairpin in some instances, due to the fact that the shRNAs described herein can be more efficient in RNA interference and less likely to induce cellular stress and/or toxicity.

Additionally, the phrase "small hairpin RNA" and the term "shRNA" include nucleic acids that also contain moieties other than ribonucleotide moieties, including, but not limited to, modified nucleotides, modified internucleotide linkages, non-nucleotides, deoxynucleotides and analogs of the nucleotides mentioned thereof.

The term "siRNA", as used herein, refers to an RNA molecule comprising a double stranded region and a 3' overhang of nonhomologous residues at each end. The double stranded region is typically about 18 to about 30 nucleotides in length, and the overhang may be of any length of nonhomologous residues, but a 2 nucleotide overhang is preferred.

The phrase "antisense sequence", as used herein, refers to a polynucleotide or region of a polynucleotide that is substantially complementary (e.g., 80% or more) or 100% complementary to a target nucleic acid of interest. An antisense sequence can be composed of a polynucleotide region that is RNA, DNA or chimeric RNA/DNA. Any nucleotide within an antisense sequence can be modified by including substituents coupled thereto, such as in a 2' modification. The antisense sequence can also be modified with a diverse group of small molecules and/or conjugates. For example, an antisense sequence may be complementary, in whole or in part, to a molecule of messenger RNA, an RNA sequence that is not mRNA (e.g., tRNA, rRNA, hnRNA, negative and positive stranded viral RNA and its complementary RNA) or a sequence of DNA that is either coding or non-coding.

The phrase "sense sequence", as used herein, refers to a polynucleotide or region that has the same nucleotide sequence, in whole or in part, as a target nucleic acid such as a messenger RNA or a sequence of DNA. When a sequence is provided, by convention, unless otherwise indicated, it is the sense sequence (or region), and the presence of the complementary antisense sequence (or region) is implicit.

The term "complementary", as used herein, refers to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G), or in any other manner that allows for the formation of stable duplexes.

"Perfect complementarity" or "100% complementarity", as used herein, refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other. For example, for two 19-mers, if 17 base pairs on each strand or each region can hydrogen bond with each other, the polynucleotide strands exhibit 89.5% complementarity. Substantial complementarity refers to polynucleotide strands or regions exhibiting about 80% or greater complementarity.

The term "deoxynucleotide", as used herein, refers to a nucleotide or polynucleotide lacking an OH group at the 2' or 3' position of a sugar moiety with appropriate bonding and/or 2', 3' terminal dideoxy, instead having a hydrogen bonded to the 2' and/or 3' carbon.

The terms "deoxyribonucleotide" and "DNA", as used herein, refer to a nucleotide or polynucleotide comprising at least one ribosyl moiety that has an H at its 2' position of a ribosyl moiety instead of an OH.

The term "mismatch", as used herein, includes situations in which Watson-Crick base pairing does not take place between a nucleotide of a antisense sequence and a nucleotide of a sense sequence, where the nucleotides are flanked by a duplex comprising base pairs in the 5' direction of the mismatch beginning directly after (in the 5' direction) the mismatched position and in the 3' direction of the mismatch beginning directly after (in the 3' direction) the mismatched position. Examples of mismatches include, without limitation, an A across from a G, a C across from an A, a U across from a C, an A across from an A, a G across from a G, a C across from a C, and so on. Mismatches also include an abasic residue across from a nucleotide or modified nucleotide, an acyclic residue across from a nucleotide or modified nucleotide, a gap, or an unpaired loop. In its broadest sense, a mismatch includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position. Preferred mismatches include a G across from an A, and an A across from a C. A particularly preferred mismatch comprises an A across from an A, G across from a G, C across from a C, and U across from a U.

The phrase "RISC" and "RNA induced silencing complex" are used interchangeably herein, and represent a complex of proteins that mediate RNAi (see, e.g., Hutvagner, G. FEBS Letters, 2005 579(26):5850-7) (incorporated herein by reference in its entirety).

The phrase "RNA interference" and the term "RNAi" are used interchangeably herein, and refer to the process by which a single, double, or T-shaped molecule (e.g., an siRNA, an shRNA, an miRNA, a piRNA) exerts an effect on a biological process by interacting with one or more components of the RNAi pathway including, but not limited to, Drosha, Dicer, Argonaute family proteins, etc. The process includes, but is not limited to, gene silencing by degrading mRNA; attenuating translation, interactions with tRNA, rRNA, hnRNA, cDNA and genomic DNA; and inhibiting as well as methylating DNA with ancillary proteins. In addition, molecules that modulate RNAi (e.g., siRNA, piRNA, or miRNA inhibitors) are included in the list of molecules that enhance the RNAi pathway (see, e.g., Tomari, Y. et al. Genes Dev. 2005, 19(5):517-29) (incorporated herein by reference in their entirety).

The phrase "silencing", as used herein, means an RNAi-mediated reduction in gene expression that can be measured by any number of methods including reporter methods such as for example luciferase reporter assay, PCR-based methods, Northern blot analysis, Branched DNA, western blot analysis, and other art recognized techniques.

The term "alkyl", as used herein, refers to a hydrocarbyl moiety that can be saturated or unsaturated, and substituted or unsubstituted. It may comprise moieties that are linear, branched, cyclic and/or heterocyclic, and contain functional groups such as ethers, ketones, aldehydes, carboxylates, etc. Unless otherwise specified, alkyl groups are not cyclic, heterocyclic, or comprise functional groups.

Exemplary alkyl groups include, but are not limited to, substituted and unsubstituted groups of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicoyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, and 2-ethylhexyl. The term alkyl also encompasses alkenyl groups, such as vinyl, allyl, aralkyl and alkynyl groups. Unless otherwise specified, alkyl groups are not substituted.

Substitutions within an alkyl group, when specified as present, can include any atom or group that can be tolerated in the alkyl moiety, including but not limited to halogens, sulfurs, thiols, thioethers, thioesters, amines (primary, secondary, or tertiary), amides, ethers, esters, alcohols and oxygen. The alkyl groups can by way of example also comprise modifications such as azo groups, keto groups, aldehyde groups, carboxyl groups, nitro, nitroso or nitrile groups, heterocycles such as imidazole, hydrazine or hydroxylamino groups, isocyanate or cyanate groups, and sulfur containing groups such as sulfoxide, sulfone, sulfide, and disulfide. Unless otherwise specified, alkyl groups do not comprise halogens, sulfurs, thiols, thioethers, thioesters, amines, amides, ethers, esters, alcohols, oxygen, or the modifications listed above.

Further, alkyl groups may also contain hetero substitutions, which are substitutions of carbon atoms, by for example, nitrogen, oxygen or sulfur. Heterocyclic substitutions refer to alkyl rings having one or more heteroatoms. Examples of heterocyclic moieties include but are not limited to morpholino, imidazole, and pyrrolidino. Unless otherwise specified, alkyl groups do not contain hetero substitutions or alkyl rings with one or more heteroatoms (i.e., heterocyclic substitutions).

The preferred alkyl group for a 2' modification is a methyl group with an O-linkage to the 2' carbon of a ribosyl moiety, i.e., a 2' O-alkyl that comprises a 2'-O-methyl group.

The phrase "2'-O-alkyl modified nucleotide", as used herein, refers to a nucleotide unit having a sugar moiety, for example a deoxyribosyl moiety that is modified at the 2' position such that an oxygen atom is attached both to the carbon atom located at the 2' position of the sugar and to an alkyl group. In various embodiments, the alkyl moiety consists essentially of carbons and hydrogens. A particularly preferred embodiment is one wherein the alkyl moiety is methyl.

As used herein, the term "2' carbon modification" refers to a nucleotide unit having a sugar moiety, for example a moiety that is modified at the 2' position of the sugar subunit. A "2'-O-alkyl modified nucleotide" is modified at this position such that an oxygen atom is attached both to the carbon atom located at the 2' position of the sugar and to an alkyl group, e.g., 2'-O-methyl, 2'-O-ethyl, 2'-O-propyl, 2'-O-isopropyl, 2'-O-butyl, 2'-O-isobutyl, 2'-O-ethyl-O-methyl(-OCH$_2$CH$_2$OCH$_3$), and 2'-O-ethyl-OH (—OCH$_2$CH$_2$OH). A "2' carbon sense sequence modification", as used herein, refers to a modification at the 2' carbon position of a nucleotide on the sense sequence. A "2' carbon antisense sequence modification", as used herein, refers to a modification at the 2' carbon position of a nucleotide on the antisense sequence.

The term "nucleotide", as used herein, refers to a ribonucleotide or a deoxyribonucleotide or modified from thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Preferably, a "nucleotide" comprises a cytosine, uracil, thymine, adenine, or guanine moiety.

Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH$_2$, NHR, NR$_2$, or CN, wherein R is an alkyl moiety as defined herein. Nucleotide analogs also include nucleotides with bases such as inosine, queuosine, xanthine, sugars such as 2'-methyl ribose, non-natural phophodiester linkages such as methylphosphonates, phophorothioates and peptides.

Modified bases refer to nucleotide bases such as, for example, adenine, guanine, cytosine, thymine, and uracil, xanthine, inosine, and queuosine that have been modified by the replacement or addition of one or more atoms or groups. Some examples of types of modifications include nucleotides that are modified with respect to the base moieties, include but are not limited to, alkylated, halogenated, thiolated, aminated, amidated, or acetylated bases, in various combinations. More specific modified bases include, for example, 5-propynyluridine, 5-propynylcytidine, 6-methyladenine, 6-methylguanine, N,N,-dimethyladenine, 2-propyladenine, 2-propylguanine, 2'-aminoadenine, 1-methylinosine, 3-methyluridine, 5-methylcytidine, 5-methyluridine and other nucleotides having a modification at the 5 position, 5-(2-amino)propyluridine, 5-halocytidine, 5-halouridine, 4-acetylcytidine, 1-methyladenosine, 2-methyladenosien, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4-thioribose, and other sugars, heterocycles, or carbocycles. The term nucleotide analog also includes what are known in the art as universal bases. By way of example, universal bases include but are not limited to 3-nitropyrrole, 5-nitroindole, or nebularine.

Further, the term nucleotide analog also includes those species that have a detectable label, such as, for example, a radioactive or fluorescent moiety, or mass label attached to the nucleotide.

The term "overhang", as used herein, refers to terminal non-base pairing nucleotide(s) resulting from one strand or region extending beyond the terminus of the complementary strand to which the first strand or region forms a duplex. One or more polynucleotides that are capable of forming a duplex through hydrogen bonding can have overhangs. The single-stranded region extending beyond the 3' end of the duplex is referred to as an overhang.

The term "ribonucleotide" and the phrase "ribonucleic acid" (RNA), as used herein, refer to a modified or unmodified nucleotide or polynucleotide comprising at least one ribonucleotide unit. A ribonucleotide unit comprises an oxygen attached to the 2' position of a ribosyl moiety having a nitrogenous base attached in N-glycosidic linkage at the 1' position of a ribosyl moiety, and a moiety that either allows for linkage to another nucleotide or precludes linkage.

The phrase "heating and snap cooling", as used herein, refers to a two-step procedure that involves heat-denaturing nucleic acids in a sample followed by rapid cooling. For example, tubes that contain shRNA solutions are denatured in a 95° C. heat block for 4 to 5 minutes followed by immediately placing the tubes into an ice-water bath for 30 minutes. Such "heating and snap cooling" favors the formation of shRNA monomers over multimers.

The phrase "pharmaceutically acceptable carrier", as used herein, means a pharmaceutically acceptable salt, solvent, suspending agent or vehicle for delivering a composition of the present disclosure to the animal or human. The carrier may be liquid, semisolid or solid, and is often synonymously used with diluent, excipient or salt. The phrase "pharmaceutically acceptable" means that an ingredient, excipient, carrier, diluent or component disclosed is one that is suitable for use with humans and/or animals without undue adverse side effects (such as toxicity, irritation, and allergic response) commensurate with a reasonable benefit/risk ratio. See Remington's Pharmaceutical Sciences 16$^{th}$ edition, Osol, A. Ed (1980) (incorporated herein by reference in its entirety).

The term "about" is used herein to mean a value±20% of a given numerical value. Thus, "about 60%" means a value of between 60±(20% of 60) (i.e., between 48 and 70).

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The disclosure illustratively described herein suitably may be practiced in the absence of any element of elements, limitation or limitations that is not specifically disclosed herein.

In some embodiments, methods of testing shRNAs targeting HCV IRES sequences are included to identify those sequences having sufficient activity (e.g., the highest activity among a selected group of such sequences) to be a candidate for use as a treatment. Testing may also include screening for shRNAs having undesirable off-target effects, IFN induction or general cytotoxic effects. Off-target effects include, without limitation, knockdown of nontargeted genes, inhibition of expression of non-targeted genes, and competition with natural microRNA pathways. Methods of identifying cytotoxic effects are known in the art.

In one embodiment, an shRNA described herein comprises a sequence complementary to a sequence of the internal ribosome entry site (IRES) element of hepatitis C virus (HCV).

A dual reporter luciferase plasmid was used in which firefly luciferase (fLuc) expression was dependent on the HCV IRES. Expression of the upstream renilla luciferase is not HCV IRES-dependent and is translated in a Cap-dependent process. Direct transfection of HCV IRES shRNAs efficiently blocked HCV IRES-mediated fluc expression in human 293FT and Huh7 cells. Control shRNAs containing a double mutation had little or no effect on fLuc expression, and shRNAs containing only a single mutation showed partial inhibition. These shRNAs were also evaluated in a mouse model where DNA constructs were delivered to cells in the liver by hydrodynamic transfection via the tail vein. The dual luciferase expression plasmid, the shRNAs, and secreted alkaline phosphatase plasmid were used to transfect cells in the liver, and the animals were imaged at time points over 12 to 96 hours. In vivo imaging revealed that HCV IRES shRNA directly, or alternatively expressed from a polIII-plasmid vector, inhibited HCV IRES-dependent reporter gene expression; mutant or irrelevant shRNAs had little or no effect. These results indicate that shRNAs, delivered as RNA or expressed from viral or nonviral vectors, are useful as effective antivirals for the control of HCV and related viruses.

A loop structure can also include deoxyribonucleotides, non-nucleotide monomers and reversible linkages such as S—S bonds, which can be formed by oxidation of —SH groups introduced into nucleotide residues, e.g., as described in (Earnshwaw et al., J. Mol. Biol., 1997, 274:197-212; Sigurdsson et al. Thiol-containing RNA for the study of Structure and Function of Ribozymes. Methods: A Companion to Methods in Enzymology, 1999, 18:71-77) (incorporated herein by reference in their entirety).

Exemplary Modified shRNAs

In certain aspects, the present invention includes a polynucleotide comprising a unimolecular RNA, such as an shRNA. The shRNA can be a unimolecular RNA that includes a sense sequence, a loop region, and an antisense sequence (sometimes referred to as first and second regions, as noted above) which together form a hairpin loop structure. Preferably, the antisense and sense sequences are substantially complementary to one other (about 80% complementary or more), where in certain embodiments the antisense and sense sequences are 100% complementary to each other. In certain embodiments, the antisense and sense sequences are too short to be processed by Dicer, and hence act through an alternative pathway to that of longer double-stranded RNAs (e.g., shRNAs having antisense and sense sequences of about 16 to about 22 nucleotides in length, e.g., between 18 and 19 nucleotides in length (e.g., an sshRNA). Additionally, the antisense and sense sequences within a unimolecular RNA of the invention can be the same length, or differ in length by less than about 9 bases. The loop can be any length, with the preferred length being from 0 to 4 nucleotides in length or an equivalent length of non-nucleotidic linker, and more preferably 2 nucleotides or an equivalent length of non-nucleotidic linker (e.g., a non-nucleotide loop having a length equivalent to 2 nucleotides). In one embodiment, the loop is: 5'-UU-3' (rUrU) or 5'-tt-3', where "t" represents deoxythymidine (dTdT). Within any shRNA hairpin, a plurality of the nucleotides are ribonucleotides. In the case of a loop of zero nucleotides, the antisense sequence is linked directly to the sense sequence, with part of one or both strands forming the loop. In a preferred embodiment of a zero-nt loop shRNA, the antisense sequence is about 18 or 19 nt and the sense sequence is shorter than the antisense sequence, so that one end of the antisense sequence forms the loop.

A hairpin can be organized in either a left-handed (L) hairpin (i.e., 5'-antisense-loop-sense-3') or a right-handed (R) hairpin (i.e., 5'-sense-loop-antisense-3'). Furthermore, an shRNA may also contain overhangs at either the 5' or 3' end of either the sense sequence or the antisense sequence, depending upon the organization of the hairpin. Preferably, if there are any overhangs, they are on the 3' end of the hairpin and comprise between 1 to 6 bases. The presence of an overhang is preferred for R-type hairpins, in which case a 2-nt overhang is preferred, and a UU or tt overhang is most preferred.

Modifications can be added to enhance shRNA stability, functionality, and/or specificity and to minimize immunostimulatory properties. For example, the overhangs can be unmodified, or can contain one or more specificity or stabilizing modifications, such as a halogen or O-alkyl modification of the 2' position, or internucleotide modifications such as phosphorothioate modification. The overhangs can be ribonucleic acid, deoxyribonucleic acid, or a combination of ribonucleic acid and deoxyribonucleic acid.

In another non-limiting example of modifications that can be applied to left handed hairpins, 2'-O-methyl modifications (or other 2' modifications, including but not limited to other 2'-O-alkyl modifications) can be added to nucleotides at position 15, 17, or 19 from the 5' antisense terminus of the hairpin, or any two of those positions, or all three, as well as to the loop nucleotides and to every other nucleotide of the sense sequence except for nucleotides 9, 10 and 11 from the 5'-most nucleotide of the sense sequence (also called the 9$^{th}$, 10$^{th}$, and 11$^{th}$ nucleotides), which should have no modifications that block "slicing" activity. Any single modification or group of modifications described in the preceding sentence can be used alone or in combination with any other modification or group of modifications cited.

It was observed in previous studies (Ui-Tei et al., NAR 2008) that the specificity of siRNAs can be increased by modifying the seed region of one or both strands. In another non-limiting example of modifications that can be applied to hairpins, nt 1-6 of the antisense sequence and nt 14-19 of the sense sequence can be 2'-O-methylated to reduce off-target effects. In a preferred embodiment, only nt 1-6 are modified from 2'-OH to 2'-H or 2'-O-alky.

As the sense sequence of an shRNA can potentially enter RISC and compete with the antisense (targeting) strand, modifications that prevent sense sequence phosphorylation are valuable in minimizing off-target signatures. Thus, desirable chemical modifications that prevent phosphorylation of the 5' carbon of the 5'-most nucleotide of right-handed shRNA of the invention can include, but are not limited to, modifications that: (1) add a blocking group (e.g., a 5'-O-alkyl) to the 5' carbon; or (2) remove the 5'-hydroxyl group (e.g., 5'-deoxy nucleotides) (see, e.g., WO 2005/078094).

In addition to modifications that enhance specificity, modifications that enhance stability can also be added. In one embodiment, modifications comprising 2'-O-alkyl groups (or other 2' modifications) can be added to one or more, and preferably all, pyrimidines (e.g., C and/or U nucleotides) of the sense sequence. Modifications such as 2' F or 2'-O-alkyl of some or all of the Cs and Us of the sense sequence/region, respectively, or the loop structure, can enhance the stability of the shRNA molecules without appreciably altering target specific silencing. It should be noted that while these modifications enhance stability, it may be desirable to avoid the addition of these modification patterns to key positions in the hairpin in order to avoid disruption of RNAi (e.g., that interfere with "slicing" activity).

Additional stabilization modifications to the phosphate backbone may be included in the shRNAs in some embodiments of the present invention. For example, at least one phosphorothioate, phosphordithioate, and/or methylphosphonate may be substituted for the phosphate group at some or all 3' positions of nucleotides in the shRNA backbone, or any particular subset of nucleotides (e.g., any or all pyrimidines in the sense sequence of the oligonucleotide backbone), as well as in any overhangs, and/or loop structures present. These modifications may be used independently or in combination with the other modifications disclosed herein.

Description of modified shRNAs of interest can be found in the following references, both of which are incorporated herein by reference in their entirety: Q. Ge, H. Ilves, A. Dallas, P. Kumar, J. Shorenstein, S. A. Kazakov, and B. H. Johnston (2010) Minimal-length short hairpin RNAs: The Relationship of Structure and RNAi Activity. RNA 16(1): 106-17 (Epub Dec. 1, 2009); and Q. Ge, A. Dallas, H. Ilves, J. Shorenstein, M. A. Behlke, and B. H. Johnston (2010) Effects of Chemical Modification on the Potency, Serum Stability, and Immunostimulatory Properties of Short shRNAs. RNA 16(1):118-30 (Epub Nov. 30, 2009).

Modified shRNAs according to aspects of the present invention may include additional chemical modifications for any of a variety of purposes, including 3' cap structures (e.g., an inverted deoxythymidine), detectable labels conjugated to one or more positions in the shRNA (e.g., fluorescent labels, mass labels, radioactive labels, etc.), or other conjugates that can enhance delivery, detection, function, specificity, or stability (e.g., amino acids, peptides, proteins, sugars, carbohydrates, lipids, polymers, nucleotides, polynucleotides, etc.). Combinations of additional chemical modifications may be employed as desired by the user.

Kits

The subject invention also includes kits for inhibiting expression of a target gene in a cell, the kit including a chemically modified shRNA as described herein. A "kit" refers to any system for delivering materials or reagents for carrying out a method of the invention. In the context of reaction assays, such delivery systems include systems that allow for the storage, transport, or delivery of reaction reagents (e.g., chemically modified shRNA, culture medium, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. Such contents may be delivered to the intended recipient together or separately. For example, a first container may contain a chemically modified shRNA for use in an assay, while a second container contains culture media RNA delivery agents (e.g., transfection reagents).

As noted above, the subject kits can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control reagents, e.g., non-chemically modified shRNA.

Whenever a range is given in the specification, for example, a temperature range, a time range, a percent sequence identity, a sequence complementarity range, a length range, or a composition or concentration range, all intermediate ranges and subranges, as well as all individual values included in the ranges given are intended to be included in the disclosure.

The invention is further illustrated by the following examples. The examples are provided for illustrative purposes only. They are not to be construed as limiting the scope or content of the invention in any way.

EXAMPLES

Example 1: Deoxynucleotide Substitution of the Antisense Sequence Affects the Activity of L sshRNAs We investigated whether deoxynucleotide substitution could be applied to L sshRNAs without affecting their activity.

sshRNAs with and without chemical modifications were synthesized by IDT (Coralville, Iowa), resuspended in RNase- and pyrogen-free buffer (Dharmacon, 20 mM KCl, 6 mM HEPES-KOH (pH7.5), 0.2 mM $MgCl_2$). si19-3 (antisense sequence 5'-UGAGGUUUAG-GAUUCGUGCUU-3' (SEQ ID NO: 52), sense sequence 5'-GCACGAAUCCUAAACCUCAUU-3') (SEQ ID NO: 53) that targets the same sequence (346-364) of HCV IRES as SG105 (see Table 1) was synthesized by Dharmacon (Boulder, Colo.), resuspended in the same buffer and annealed according to the manufacturer's instruction. Human 293FT (Invitrogen) cells were maintained in DMEM with 10% heat-inactivated fetal bovine serum (Hyclone), supplemented with 2 mM L-glutamine and 1 mM sodium pyruvate. The day prior to transfection, cells were seeded at 23,000 cells per well in a 96-well plate, resulting in about 80% cell confluency at the time of transfection. Cells were transfected with Lipofectamine™ 2000 (Invitrogen, Carlsbad, Calif.) following the manufacturer's instructions. Specifically, synthetic shRNA samples with various concentrations (e.g., 10, 3, 1, 0.3, 0.1, 0.03, 0.01 and 0.003 nM), 13 ng DNA plasmid pSG154m (a firefly luciferase (fLuc) reporter plasmid whose expression was driven by the HCV internal ribosome entry site (IRES)), 20 ng pSEAP2-control plasmid (BD Biosciences Clontech, as transfection controls) were mixed with 0.25 µl Lipofectamine 2000 in OptiMem (Invitrogen) and introduced into 293FT cells in triplicate. Forty-eight hours later, the supernatant was removed, heated at 65° C. for 15-30 minutes, and 5-10 µl of the supernatant was added to 150 µl p-nitrophenyl phosphate liquid substrate system (pNPP, Sigma). After 30-60 minute incubation at room temperature, samples were read (405 nm) on a Molecular Devices Thermomax microplate reader and quantified using SOFTmax software (Molecular Devices). The remaining cells were lysed and luciferase activity was measured using MicroLumat LB 96P luminometer (Berthold).

Unless otherwise indicated, all the siRNA and shRNA samples were tested in triplicate and two or more independent experiments were performed. The $IC_{50}$s of the dose response curves were calculated using GraFit data analysis software.

Comparing to controls without sshRNA or with control sshRNA, the expression levels of fLuc with the IRES-specific shRNAs reflects the target gene knock-down efficacy of the tested hairpins. No difference of fLuc expression was found between the control without sshRNA or the one with control sshRNA (data not shown). As shown in FIG. 1, L sshRNAs with substitution of DNA (6 nucleotides) at 5' end of the antisense sequence (SG206 and SG208) had lower efficacy than the one with substitutions only at the 3' end of the sense sequence (SG207).

The sequence of these shRNAs are shown in Table 1. Nucleotides forming the shRNA loops and 3' overhangs are shown in bold. Deoxyribonucleotides are indicated by lower-case letters.

TABLE 1 shRNA sequences targeting the HCV IRES used in Example 1

| Sequence ID# | Sequence (5'-3') | Target position on IRES | shRNA abbrev | $IC_{50}$ (pM) |
| --- | --- | --- | --- | --- |
| SEQ ID NO: 1 | UGA GGU UUA GGA UUC GUG CUU GCA CGA AUC CUA AAC CUC A | 346-364 | SG105 | 2.3 |
| SEQ ID NO: 2 | tga ggt UUA GGA UUC GUG CUU GCA CGA AUC CUA AAC CUC A | 346-364 | SG206 | 14.5 |
| SEQ ID NO: 3 | UGA GGU UUA GGA UUC GUG CUU GCA CGA AUC CUA Aac ctc a | 346-364 | SG207 | 5.6 |
| SEQ ID NO: 4 | tga ggt UUA GGA UUC GUG CUU GCA CGA AUC CUA Aac ctc a | 346-364 | SG208 | 11.0 |

Example 2: 2'%0-Methyl Modification of the Antisense sequence Affects the Activity of L sshRNAs 2'-O-methyl (2'-OMe) modified RNA is a naturally occurring modification found in mammalian ribosomal RNAs and transfer RNAs. We investigated whether 2'-OMe modification could be applied to L sshRNAs without affecting their activity using the 293FT cell transfection assay described above in Example 1. Similar to the results with DNA substitution, the L sshRNA (SG216) whose antisense sequence were modified at every second nucleotide beginning with the most 5' terminal nucleotide lost its RNAi activity dramatically (FIG. 2A). Similar results were obtained with sshRNA whose antisense and sense sequence were both modified, either at alternating nucleotides or uridines alone (SG203 and SG205). However, when alternating 2'-OMe nucleotides were placed only in the sense sequence, the activity of the modified sshRNA (SG204) was not affected and even appeared to be slightly higher than the unmodified sshRNA (SG105) and the control siRNA that target the same sequence (si19-3). The dinucleotide UU that connects the 3' end of the antisense and the 5' end of the sense sequences could be also modified without affecting the sshRNA activity (SG202). No efficacy loss was found when the sense sequence and the dinucleotide connection were both 2'-OMe modified (SG224, FIG. 2B). Since the base pair immediately adjacent to the UU dinucleotide that connects the antisense and sense sequences may not be base paired due to the potential strain from a 2-nt loop, we also examined whether 2'-OMe modification of the tetraloop CUUG (mCUmUG, m representing 2'-OMe) could be combined with a modified sense sequence (SG217). As seen in FIG. 2C, the $IC_{50}$ of SG217 ($IC_{50}$=6.5 pM) was about 2-fold greater than the unmodified SG105 (3.5 pM). Interestingly, unlike siRNAs, which were found to tolerate the modification at the second nucleotide from the 5' end of the antisense sequence, that modification slightly reduced the potency of the sshRNA (SG225, FIG. 2B). Again, slight activity loss was seen with the shRNA (SG226) that had both 2'-OMe modifications used in SG225 (second nucleotide on the antisense sequence) together with those in SG224 (alternating same strand nucleotides and UU loop, FIG. 2B). Similarly, in a special sshRNA that contained a direct connection between a 19-nt antisense sequence and a 17-nt sense sequence without a connecting loop sequence, modification in the sense sequence only did not affect efficacy whereas the additional modification in the 3' end of the antisense sequence (which formed the loop of the hairpin) slightly reduced the activity (FIG. 2D). 2'-OMe modification of the guide at positions 17 (SG242) and at both positions 15 and 17 (SG243) resulted in only a slight loss of activity (FIG. 2E).

Figure 3A:
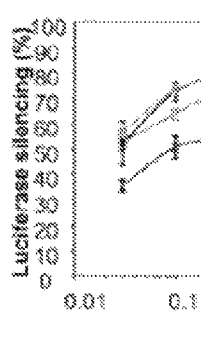
FIGS. 3A-3B test the similar modification pattern as FIG. 2 with L sshRNAs targeting two different sequences. Again, 2'-OMe modification in the antisense sequence reduced the efficacy of L sshRNAs.
Figure 3B:
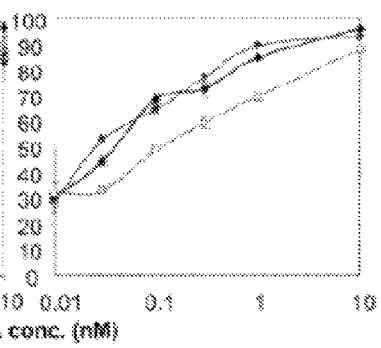
Figure 3C:
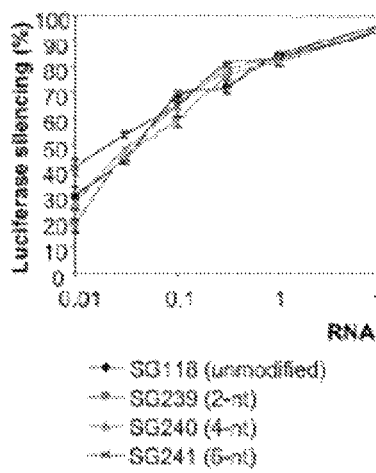
FIG. 3C compare the dose response of L sshRNA with 2, 4, and 6 2'-O-methyl ribosyl substitutions at various positions in the sense sequence. No activity loss was found.

To test whether the modification-activity relationships found for SG105 and its derivatives are true for shRNAs with different sequences, two more L shRNAs (SG118 and SG108) were chemically synthesized with and without 2'-OMe modification and compared for their dose response activity. As shown in FIG. 3A, shRNAs with modification of the sense sequence (alternating nucleotides) and the tetraloop have slightly lower activity than their parents without modification (SG218 compared to SG118, SG219 compared to SG108). However, SG237 with modification of the sense sequence and the dinucleotide UU loop showed similar potency compared to its unmodified parent, SG118 (FIG. 3B). In addition, the potencies of SG118 derivatives that have 2, 4, and 6 2'-OMe modifications in the sense sequences were compared and no activity loss was found (FIG. 3C).

Collectively, L sshRNAs appear to maintain high potency when the sense sequence is modified with 2'-OMe on alternating nucleotide or selected uridines but lose activity when the antisense sequence is modified in a similar pattern. Interestingly, as little as one nucleotide modification at positions 2, 17, and 19 of the antisense sequence reduced the RNAi activity of L sshRNA significantly (SG225, SG226 in FIG. 2B, SG217 in FIG. 2C, and data not shown). The fact that the activity of an L sshRNA is sensitive to 2'-OMe modification of the antisense sequence is unique. Various reports have applied 2'-OMe modification on the antisense sequence of siRNAs without affecting their efficacy.

The sequences of these shRNAs are shown in Table 2. Nucleotides forming the shRNA loops and 3' overhangs are shown in bold. Nucleotides with 2'-O-Methyl modification are underlined. Deoxyribonucleotides are indicated by lower-case letters.

TABLE 2 shRNA sequences used in Example 2

| Sequence ID# | Sequence (5'-3') | Target position on IRES | shRNA abbrev | IC$_{50}$ (pM) |
|---|---|---|---|---|
| SEQ ID NO: 1 | UGA GGU UUA GGA UUC GUG CUU GCA CGA AUC CUA AAC CUC A | 346-364 | SG105 | 3.5-12.5 |
| SEQ ID NO: 5 | UGA GGU UUA GGA UUC GUG <u>C</u>UU GCA CGA AUC CUA AAC CUC A | 346-364 | SG202 | 4.3 |
| SEQ ID NO: 6 | <u>UGA</u> GGU <u>UUA</u> GGA <u>UUC</u> GUG <u>C</u>tt G<u>CA</u> <u>CGA</u> A<u>UC</u> <u>CUA</u> A<u>AC</u> <u>CUC</u> A | 346-364 | SG203 | 24.9 |
| SEQ ID NO: 7 | UGA GGU UUA GGA UUC GUG Ctt G<u>CA</u> <u>CGA</u> A<u>UC</u> <u>CUA</u> A<u>AC</u> <u>CUC</u> A | 346-364 | SG204 | 2.0 |
| SEQ ID NO: 8 | UGA GG<u>U</u> UUA GGA UUC G<u>U</u>G Ctt GCA CGA A<u>U</u>C C<u>U</u>A AAC C<u>U</u>C A | 346-364 | SG205 | 130.2 |
| SEQ ID NO: 9 | <u>UGA</u> GGU <u>UUA</u> GGA <u>UUC</u> GUG Ctt G<u>CA</u> <u>CGA</u> A<u>UC</u> <u>CUA</u> A<u>AC</u> <u>CUC</u> A | 346-364 | SG216 | 101.5-335.1 |
| SEQ ID NO: 10 | UGA GGU UUA GGA UUC GUG <u>C</u>UU G<u>CA</u> <u>CGA</u> A<u>UC</u> <u>CUA</u> A<u>AC</u> <u>CUC</u> A | 346-364 | SG217 | 6.5 |
| SEQ ID NO: 11 | UGA GGU UUA GGA UUC GUG CUU G<u>CA</u> <u>CGA</u> A<u>UC</u> <u>CUA</u> A<u>AC</u> <u>CUC</u> A | 346-364 | SG224 | 7.6 |
| SEQ ID NO: 12 | U<u>GA</u> GGU UUA GGA UUC GUG CUU GCA CGA AUC CUA AAC CUC A | 346-364 | SG225 | 25.9 |
| SEQ ID NO: 13 | U<u>GA</u> GGU UUA GGA UUC GUG <u>C</u>UU G<u>CA</u> <u>CGA</u> A<u>UC</u> <u>CUA</u> A<u>AC</u> <u>CUC</u> A | 346-364 | SG226 | 50.4 |
| SEQ ID NO: 14 | UGA GGU UUA GGA UUC GUG CAC GAA UCC UAA ACC UCA | 346-364 | SG119 | (92.0) |

TABLE 2 -continued shRNA sequences used in Example 2

| Sequence ID# | Sequence (5'-3') | Target position on IRES | shRNA abbrev | IC50 (pM) |
|---|---|---|---|---|
| SEQ ID NO: 15 | UGA GGU UUA GGA UUC GUG CAC GAA UCC UAA ACC UCA | 346-364 | SG235 | (3.1) |
| SEQ ID NO: 16 | UGA GGU UUA GGA UUC GUG CAC GAA UCC UAA ACC UCA | 346-364 | SG236 | (6.0) |
| SEQ ID NO: 17 | AUU CGU GCU CAU GGU GCA CUU GUG CAC CAU GAG CAC GAA UUU | 335-353 | SG118 | 23.8 |
| SEQ ID NO: 18 | AUU CGU GCU CAU GGU GCA CUU GUG CAC CAU GAG CAC GAA U | 335-353 | SG218 | 27.7 |
| SEQ ID NO: 19 | AUU CGU GCU CAU GGU GCA CUU GUG CAC CAU GAG CAC GAA Utt | 335-353 | SG237 | (26) |
| SEQ ID NO: 20 | UUU UUC UUU GAG GUU UAG GUU CCU AAA CCU CAA AGA AAA AUU | 354-372 | SG108 | 11.7 |
| SEQ ID NO: 21 | UUU UUC UUU GAG GUU UAG GUU CCU AAA CCU CAA AGA AAA A | 354-372 | SG219 | 138.3 |
| SEQ ID NO: 22 | AUU CGU GCU CAU GGU GCA CUU GUG CAC CAU GAG CAC GAA Utt | 346-364 | SG239 | (58) |
| SEQ ID NO: 23 | AUU CGU GCU CAU GGU GCA CUU GUG CAC CAU GAG CAC GAA Utt | 346-364 | SG240 | (39) |
| SEQ ID NO: 24 | AUU CGU GCU CAU GGU GCA CUU GUG CAC CAU GAG CAC GAA Utt | 346-364 | SG241 | (27) |
| SEQ ID NO: 52 | UGA GGU UUA GGA UUC GUG CUU GCA CGA AUC CUA AAC CUC A | 346-364 | SG242 | |
| SEQ ID NO: 53 | UGA GGU UUA GGA UUC GUG CUU GCA CGA AUC CUA AAC CUC A | 346-364 | SG243 | |
| SEQ ID NO: 54 | CGU GCU UAG GAU UUG GAG UUU ACU CCA AAU CCU AAG CAC G | N/A | SG221 (c) | |

Note:
The shRNAs were tested in several experiments. Where there were different IC50 values in different experiments, the range of the IC50 values is shown.
( ): Estimated IC50.

Figure 3D:
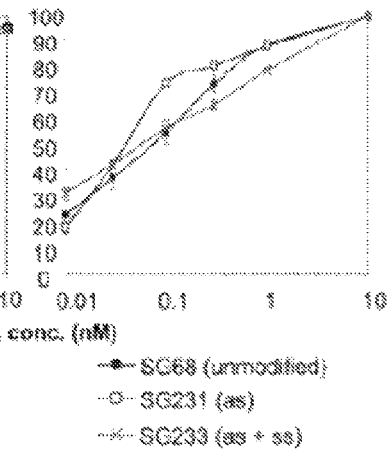
FIG. 3D depicts the dose response of R sshRNAs with 2'-O-methyl modification at various positions. The results suggest that a single 2'-O-methyl ribosyl substitution in the antisense sequence does not affect the activity of R sshRNA. No decrease of R sshRNA was found when alternating nucleotides in the sense sequence were 2'-OMe modified.

Example 3: Activity of R sshRNAs is not Affected by 2'O-Methyl Modification of the Antisense Sequence In contrast to L sshRNA, when the loop was placed at the 3' end of the sense sequence (R sshRNA), the sshRNA with the same modification pattern (second nucleotide on the antisense sequence and alternating nucleotide on the sense sequence, SG233) proved to be as effective as the unmodified (FIG. 3D).

The sequences of these shRNAs are shown in Table 3. Nucleotides forming the shRNA loops and 3' overhangs are shown in bold. Nucleotides with 2'-O-Methyl modification are underlined.

TABLE 3 shRNA sequences used in Example 3

| Sequence ID# | Sequence (5'-3') | Target position on IRES | shRNA abbrev | IC50 (pM) |
|---|---|---|---|---|
| SEQ ID NO: 25 | GCA CGA AUC CUA AAC CUC ACA AUA UGA GGU UUA GGA UUC GUG CUU | 346-364 | SG68 | 33.7 |
| SEQ ID NO: 26 | GCA CGA AUC CUA AAC CUC ACA AUA UGA GGU UUA GGA UUC GUG CUU | 346-364 | SG231 | (40.2) |

TABLE 3-continued shRNA sequences used in Example 3

| Sequence ID# | Sequence (5'-3') | Target position on IRES | shRNA abbrev | IC$_{50}$ (pM) |
|---|---|---|---|---|
| SEQ ID NO: 27 | GCA CGA AUC CUA AAC CUC ACA AUA UGA GGU UUA GGA UUC GUG CUU | 346-364 | SG233 | (55.5) |
| SEQ ID NO: 28 | GCA CGA AUC CUA AAC CUC ACA AUA UGA GGU UUA GGA UUC GUG CUU | 346-364 | SG232 | — |

( ): Estimated IC50

Figure 4:
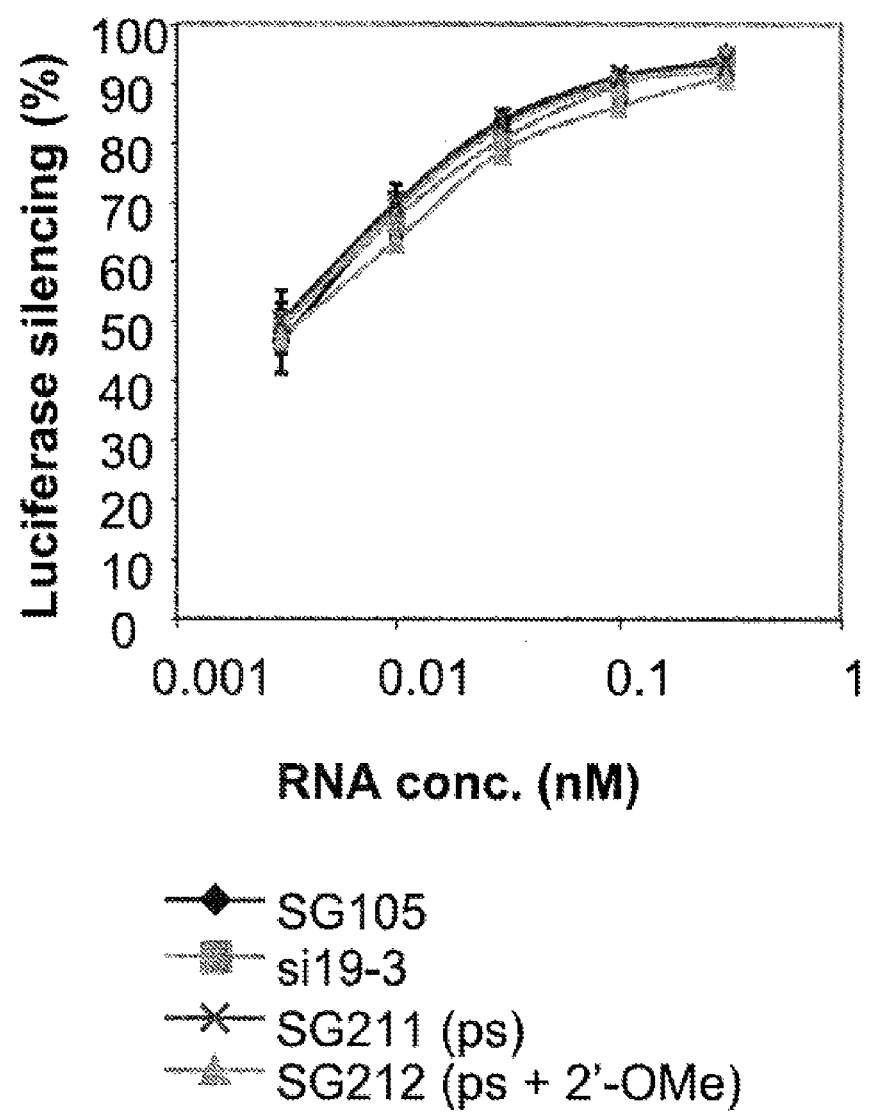
FIG. 4 compares the dose response of L sshRNA with phosphorothioate bonds in the opening ends of the duplex (see Example 4). The results indicate that L sshRNAs with or without 2'-OMe modification can tolerate the phosphorothioate bonds in the opening ends of the hairpin duplex without activity loss.

Example 4: Phosphorothioate Bonds at the Open End of the Duplex do not Affect the Activity of sshRNAs Exonucleases comprise the primary class of nucleases present in mammalian serum. We tested whether the addition of phosphorothioate bonds in the 5'-end of the antisense sequence and 3'-end of the sense sequence will affect the efficacy of L sshRNAs (SG211, FIG. 4). Compared to the unmodified molecule SG105, no RNAi activity loss was found with SG211. The addition of alternating 2'-OMe substitution in the sense sequence also did not affect the potency of the PS modified sshRNA (SG212).

The sequences of these shRNAs are shown in Table 4. Nucleotides forming the shRNA loops and 3' overhangs are shown in bold. Nucleotides with 2'-O-Methyl modification are underlined. Deoxyribonucleotides are indicated by lower-case letters. Phosphorothioate bonds are indicated by *.

TABLE 4 shRNA sequences used in Example 4

| Sequence ID# | Sequence (5'-3') | Target position on IRES | shRNA abbrev | IC$_{50}$ (pM) |
|---|---|---|---|---|
| SEQ ID NO: 1 | UGA GGU UUA GGA UUC GUG CUU GCA CGA AUC CUA AAC CUC A | 346-364 | SG105 | 2.3-3.5 |
| SEQ ID NO: 29 | U*G*A GGU UUA GGA UUC GUG CUU GCA CGA AUC CUA AAC CU*C* A | 346-364 | SG211 | 3.0 |
| SEQ ID NO: 30 | U*G*A GGU UUA GGA UUC GUG Ctt GCA CGA AUC CUA AAC CU*C* A | 346-364 | SG212 | 3.7 |

Example 5: Effect of End Conjugations on the Activity of sshRNAs

End conjugation, such as with cholesterol or alpha-tocopherol, has been shown to facilitate in vivo delivery of siRNAs to the liver (Soutschek et al. 2004; Nishina et al. 2008). Other delivery materials including nanoparticles, antibodies, etc. could be also conjugated to the end of siRNAs. To evaluate whether such a strategy affects the activity of sshRNAs, a thiol group (shown in FIG. 5) was conjugated to either the 5' or 3' end of the hairpin and gene inhibition activity was measured. As shown in FIG. 5A, 5' end conjugation (at the 5'-end of antisense sequence) completely abolished the L sshRNA activity whereas 3' end conjugation (at the 3'-end of the sense sequence) retained full efficacy. Since the antisense sequence is at the 5' end of the L sshRNA and the 5' phosphate is essential for binding to Dicer and/or Ago2 in RISC, the loss of RNAi activity by replacing the 5' phosphate may not seem surprising. A similar phenomenon was observed with siRNAs when conjugation occurred at the 5' end of the antisense sequence. R sshRNAs were also tested for the influence of end conjugation on their activities. Unlike with L sshRNAs, 5'-end conjugation (at the 5'-end of the sense sequence) of R sshRNAs did not significantly affect efficacy, whereas 3'-end conjugation (at 3'-end of the antisense sequence) reduced the potency of these R sshRNAs (FIG. 5B).

The sequences of these shRNAs are shown in Table 5. Nucleotides bearing the shRNA loops and 3' overhangs are shown in bold. Deoxyribonucleotides are indicated by lower-case letters. Phosphorothioate bonds are indicated by *.

TABLE 5 shRNA sequences used in Example 5

| Sequence ID# | Sequence (5'-3') | Target position on IRES | shRNA abbrev | IC$_{50}$ (pM) |
|---|---|---|---|---|
| SEQ ID NO: 1 | UGA GGU UUA GGA UUC GUG CUU GCA CGA AUC CUA AAC CUC A | 346-364 | SG105 | 7.7 |
| SEQ ID NO: 31 | S-S-C6-UGA GGU UUA GGA UUC GUG CUU GCA CGA AUC CUA AAC CUC A | 346-364 | SG143 | 8159.8 |
| SEQ ID NO: 32 | UGA GGU UUA GGA UUC GUG CUU GCA CGA AUC CUA AAC CUC A-C3-S-S | 346-364 | SG144 | 4.8 |
| SEQ ID NO: 25 | GCA CGA AUC CUA AAC CUC ACA AUA UGA GGU UUA GGA UUC GUG CUU | 346-364 | SG68 | 33.7 |
| SEQ ID NO: 33 | C3-GCA CGA AUC CUA AAC CUC ACA AUA UGA GGU UUA GGA UUC GUG CUU | 346-364 | SG146 | (115.0) |
| SEQ ID NO: 34 | GCA CGA AUC CUA AAC CUC ACA AUA UGA GGU UUA GGA UUC GUG CUU-C3 | 346-364 | SG147 | (400.0) |

( ): Estimated IC50

Example 6: The Effect of Modified Loop on the Activity of sshRNAs

Modifications in the loop were examined for both R and L sshRNAs. As shown in FIG. 6A, the loop of the L sshRNAs could be substituted with deoxynucleotides (SG209) without an activity loss. This is also true when phosphorothioate linkages were added into a loop that contains DNA (SG210, FIG. 6A). However, reduced efficacy was seen when phosphorothioate (PS) linkages and DNA were placed in the loop of R sshRNA, but not when PS bonds and RNA were in the loop (SG234 in FIG. 6B and SG223 in FIG. 6C).

L and R sshRNAs with modified loops that contain uncleavable linkers such as non-nucleotidic linkers (SG229 and SG228) were also tested for their target knockdown activities. As shown in FIG. 6C, none of these loop modifications significantly affected the potency of L or R sshRNAs. Since nonnucleotidic linkers, deoxynucleotides, and phosphorothioate bonds block the cleavage by RNases such as Dicer, the results suggest that cleavage at certain position in the loop is required for the activity of R sshRNA but not for L sshRNA.

Figure 7A:
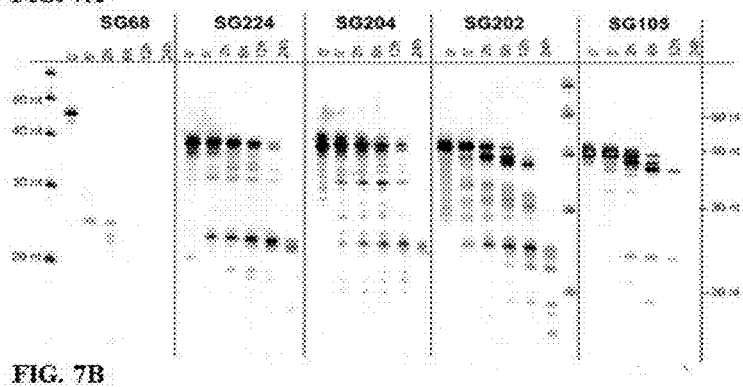
FIG. 7 depicts the serum stability of sshRNAs with and without 2'-OMe modification (see Example 7). Panel A shows that in the absence of chemical modification, the UU loop confers more stability than the 5-nucleotide loop, indicating that a hairpin with a more compact secondary structure is more nuclease resistant. The sshRNA gains additional nuclease resistance when 2'-OMe modification is added to the loop or sense sequence. 2'-O-methyl ribosyl substitution in both the loop and the sense sequence gives the sshRNA the most serum stability. Panel B shows the stability of sshRNAs with 2'-O-Me modifications at positions 15 and/or 17 of the guide strand in addition to passenger strand and loop methylation. The results indicate that these additional modifications confer additional stability to serum nucleases compared to SG224, which only has modification in the loop and passenger strand.
Figure 7B:
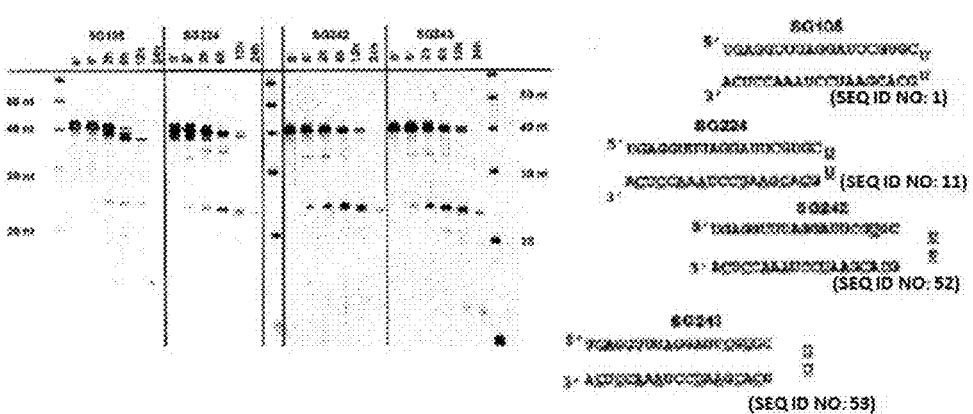

The sequences of these shRNAs are shown in Table 6. Nucleotides forming the shRNA loops and 3' overhangs are shown in bold. Deoxyribonucleotides are indicated by lower-case letters. Phosphorothioate bonds are indicated by *.

sizes around 20 to 30 nucleotides were detected in denaturing polyacrylamide gels, suggesting that the loop of the hairpin may be the most vulnerable region for serum nucleases. Interestingly, an sshRNA with 2-nt UU loop and no 3' overhang (SG105) was stable up to 2 hours of incubation in human serum. This suggests that shRNAs with small loops may be generally more resistant to nucleases. With 2'-O-Me modification at alternating nucleotides in the sense sequence and each nucleotide in the loop, the molecule remained largely intact for up to 6 to 12 hours (FIG. 7A). When 2'-O-Me modification was extended both into position 17 of the guide strand (SG242) and positions 15 and 17 of the guide strand (SG243), a modest increase in serum stability was observed (FIG. 7B).

For in vivo application, although various formulation approaches insulate the RNA from nucleases to various degrees, it is anticipated that no matter which delivery platform is most efficacious, there is a good chance that some level of stabilization will be necessary.

TABLE 6 shRNA sequences used in Example 6

| Sequence ID# | Sequence (5'-3') | Target position on IRES | shRNA abbrev | IC$_{50}$ (pM) |
|---|---|---|---|---|
| SEQ ID NO: 1 | UGA GGU UUA GGA UUC GUG CUU GCA CGA AUC CUA AAC CUC A | 346-364 | SG105 | 3.7 |
| SEQ ID NO: 35 | UGA GGU UUA GGA UUC GUG Ctt GCA CGA AUC CUA AAC CUC A | 346-364 | SG209 | 6.6 |
| SEQ ID NO: 36 | UGA GGU UUA GGA UUC GUG* **c*t*t*** g*CA CGA AUC CUA AAC CUC A | 346-364 | SG210 | 6.2 |
| SEQ ID NO: 37 | UGA GGU UUA GGA UUC GUG CC3C3 GCA CGA AUC CUA AAC CUC A | 346-364 | SG229 | 1.4 |
| SEQ ID NO: 25 | GCA CGA AUC CUA AAC CUC ACA AUA UGA GGU UUA GGA UUC GUG CUU | 346-364 | SG68 | 33.7 |
| SEQ ID NO: 38 | GCA CGA AUC CUA AAC CUC ACA C3C3A UGA GGU UUA GGA UUC GUG CUU | 346-364 | SG228 | 57.1 |
| SEQ ID NO: 39 | GCA CGA AUC CUA AAC CUC **A*C*A* A*U*A* UGA GGU UUA GGA UUC GUG CUU** | 346-364 | SG223 | 20.5 |
| SEQ ID NO: 40 | GCA CGA AUC CUA AAC CUC **A*c*a* a*t*a* UGA GGU UUA GGA UUC GUG CUU** | 346-364 | SG234 | (710.0) |

( ): Estimated IC50

Example 7: 2'-OMe Modification can Improve the Serum Stability of sshRNAs

Although dsRNAs are more stable than single-stranded RNAs (ssRNAs), sshRNAs without chemical modification are still very sensitive to nucleases. sshRNAs (3.35 µg) were incubated with 10% human serum (Sigma, St Louis, Mo.) in PBS at 37° C. An aliquot of was taken out at each time point and was immediately mixed with 2× gel loading buffer (Ambion, Austin, Tex.) and stored at −80° C. Subsequent gel electrophoresis of the samples was performed under denaturing condition: 12% polyacrylamide, 20% formamide, and 8M urea. The gel was stained with SYBR Gold (Invitrogen). As shown in FIG. 7A, the majority of the naked sshRNA with a 5-nt loop (SG68) was degraded within 5 minutes upon incubation in 10% human serum at 37° C. Faint bands with

Example 8: 2'-OMe Modification can Reduced Innate Immune Responses

Numerous studies have demonstrated the capability of unmodified shRNAs and siRNAs to induce the undesired expression of proinflammatory cytokines such as type I interferon (IFN), IL-6, TNF-α, etc. Several factors, including length, sequence, and structure of nucleic acids could be responsible for this effect. To evaluate cytokine induction by sshRNAs in the presence and absence of chemical modifications, freshly purified human peripheral blood mononuclear cells (PBMCs) and human fetal lung fibroblast (MRC-5) cells were transfected with these RNAs and the levels of mRNAs encoding OAS-1, an interferon-induced enzyme, as well as the cytokines IFN-β, IL-6, and TNF-α were measured. PBMCs are a mixed immune cell population that is more representative of the natural spectrum of immune receptors in vivo (Judge et al. 2006) Unlike many of other cultured cell lines that have various degrees of genetic abnormalities including defects in the IFN response pathway, MRC-5 cells were found to remain sensitive to immunostimulatory oligos (Marques et al. 2006). Human PBMCs were prepared from buffy coats (Stanford Blood Center) by density gradient centrifugation, washed, and then seeded in 24-well plates at 5×10$^5$ cells per well in RPMI 1640 containing 10% heat-inactivated fetal calf serum. Transfections were performed using DOTAP (Roche, Basel, Schweiz) following the manufacturer's instructions. Similarly, MRC-5 cells (human fetal lung fibroblast) were seeded in 24-well plates at 6×10$^4$ cells per well with DMEM containing 10% heat-inactivated fetal calf serum. Transfections were done using Lipofectamine 2000® following the manufacturer's instructions. shRNAs (20 nM or 100 nM) were transfected in each well in triplicate. Six or twenty-four hours later, the cells were lysed in Trizol (Invitrogen) and total RNA was extracted according to the manufacturer's instructions. Quantitative RT-PCR was performed using High-Capacity cDNA Reverse Transcription Kits, TaqMan Universal PCR Master Mix, SYBR power Master Mix, Taqman probes OAS1 (Hs00242943_m1), IFN-β (Hs01077958_s1), IL-6 (Hs99999032_m1) and GAPDH (Hs99999905_m1) and a Fast 7500 real time PCR instrument (Applied Biosystems, Foster City, Calif.) following the manufacturer's instructions. Primers used were:

```
TLR3 forward:
                                        (SEQ ID NO: 54)
5'-TCCCAAGCCTTCAACGACTG-3';

TLR3 reverse:
                                        (SEQ ID NO: 55)
5'-TGGTGAAGGAGAGCTATCCACA-3';

TLR7 forward:
                                        (SEQ ID NO: 56)
5'-TTACCTGGATGGAAACCAGCTAC-3';

TLR7 reverse:
                                        (SEQ ID NO: 57)
5'-TCAAGGCTGAGAAGCTGTAAGCTA-3';

TLR8 forward:
                                        (SEQ ID NO: 58)
5'-GAGAGCCGAGACAAAAACGTTC-3';

TLR8 reverse:
                                        (SEQ ID NO: 59)
5'-TGTCGATGATGGCCAATCC-3';

RIG-I forward:
                                        (SEQ ID NO: 60)
5'-CAGTATATTCAGGCTGAG-3';

RIG-I reverse:
                                        (SEQ ID NO: 61)
5'-GGCCAGTTTTCCTTGTC-3';

PKR forward:
                                        (SEQ ID NO: 62)
5'-TCTGACTACCTGTCCTCTGGTTCTT-3';
```

```
-continued
PKR reverse:
                                        (SEQ ID NO: 63)
5'-GCGAGTGTGCTGGTCACTAAAG-3'
```

(Hayashi et al. 2003; Terhorst et al. 2007).

Since the shRNAs used in this study have maximum target gene knockdown (based on an HCV IRES-fLuc reporter model) at concentrations of 0.3 nM to 10 nM, we used 20 nM shRNAs in the first PBMC transfection experiment to examine their capabilities to upregulate OAS and IFN expression. To make sure that we could detect even very modest immunostimulatory properties, a high concentration of 100 nM shRNA was later used in all MRC-5 cell transfections.

Figure 8:
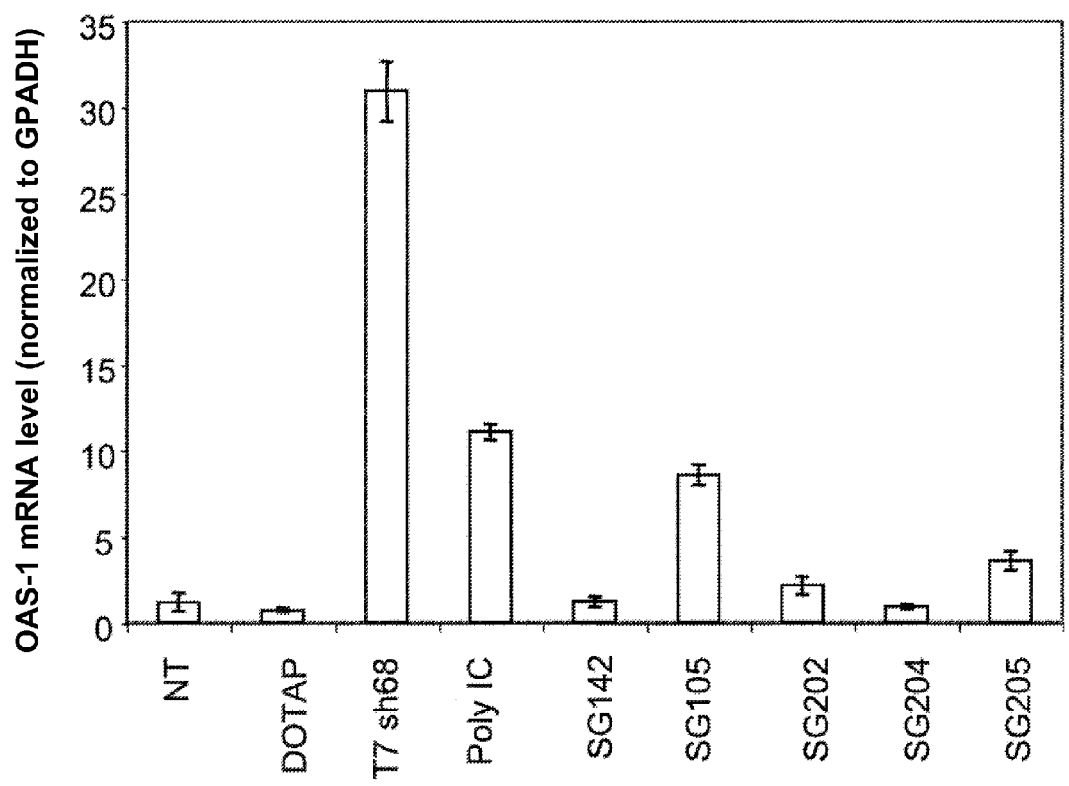
FIG. 8 compares the expression of interferon responsive gene OAS induced by sshRNAs with and without 2'-OMe modification in human PBMCs (see Example 8). The results show that the tested sshRNA (no modification) with blunted end (SG105) but not with sticky end (SG142) induces type I IFN response. The 2'-OMe modification in the sense sequence suppress the IFN response triggered by the blunt-end hairpin.

Poly I:C (Pharmacia, Stockholm, Sweden) and a T7 transcribed shRNA induced OAS-1, IFN-β, IL-6, and TNF-α in PBMCs and MRC-5 cells (FIG. 8, Table 7 and 8). The results obtained from both cell types were in agreement. Synthetic L sshRNAs against three target sequences were investigated (SG142, SG108, and SG118). SG142 did not trigger inflammatory cytokine response unless the 3' overhang was removed (comparing SG142 with overhang and SG105/SG117/SG119 without overhang, FIG. 8 and Table 7a-b), indicating RIG-I-mediated IFN induction by the blunt-ended hairpins. Indeed, the mRNA level of RIG-I, but not TLRs or PKR, was significantly upregulated in 293FT cells when SG119 was transfected (Table 7b). 2'-OMe modification of the alternating nucleotide in the sense sequence or uridines in both strands (SG205) significantly reduced or abolished the upregulation of cytokines and RIG-I.

It was reported that the selection of the time used to detect the inflammatory cytokine effect is important because the cytokine response to siRNA is transient, peaking between 2-8 h and fully resolving within 24 h after administration (Robbins et al. 2008). Since the detection time we chose was 24 hours after transfection, to rule out the possibility that SG142 (negative in cytokine induction at 24 h) induces innate immune response at earlier time point, we compared the expression of IFN-β and TNF-α in MRC-5 cells at 6 and 24 hours after shRNA transfection. As shown in Table 8, cytokines are negative at both time points when SG142 is examined. When SG118 is transfected, the expression of these cytokines is much higher at 24 h than at 6 h. The positive control, PolyI:C upregulated TNF-α in similar kinetics, peaking at 24 h. However, IFN-β expression level did not increase after 6 h.

Two other L sshRNAs, SG118 and SG108, stimulated both PBMC and MRC-5 to express OAS, IFN-β, TNF-α and IL-6 even when the 3' overhang was present. This implies that the sequence itself may contain stimulatory motif to TLR or other proteins that are involved in innate immune response to RNA oligos. The published immunostimulatory sequences such as "UGUGU" and "GUCCUUCAA" are not present in these L sshRNAs (Heil et al. 2004; Hornung et al. 2005; Judge et al. 2005). Apparently, avoiding these identified stimulatory motifs does not prevent the activation of the innate immune system. RNAs with alternating 2'-OMe modification in the sense sequence and loop (SG218 and SG219) again diminished the cytokine induction property (Table 7 and Table 8).

In addition to the proinflammatory cytokines such as IFN-β, IL-6, and TNF-α, we also examined the expressions of innate immune response mediators such as TLRs, RIG-I, and PKR. As shown in Table 7b, PolyI:C strongly induced the upregulation of all the mediators tested, especially the expression of TLRs and RIG-I. T7 transcribed shRNA specifically upregulates RIG-I transcription. Interestingly, this RNA molecule also stimulates the expression of TLR3. Synthetic sshRNAs such as SG142, SG108, and SG118 increase the transcription levels of TLR3, RIG-I at various degrees (Table 7a). These inflammatory responses were suppressed by having alternating 2'-OMe modification in the sense sequence of shRNAs.

As shown in Table 9, substitution of as few as 2 of 42 native ribonucleotides in SG118 was enough to inhibit immune responses. RIG-I upregulation and subsequent cytokine induction could also be suppressed by 2'-OMe modifications (SG119 with and without 2'-OMe modification in Table 7b).

In addition, certain modifications were found to make shRNAs more immunostimulatory and 2'-OMe modification could suppress the inflammatory response to these molecules. SG105 without modification induced similar low level of innate immune response as SG119 (two shRNAs share the same targeting sequence). When the hairpin was conjugated with a group at the 3' end, or the hairpin's dinucleotide loop UU was replaced with nonnucleotidic C3C3, or phosphorothioate bonds were added to the backbone of the hairpin, a much stronger cytokine expression and unregulation of TLRs, RIGI were seen (Table 10). Thus, type I IFN and proinflammatory cytokine expression profile must be examined when these types of modification will be added to shRNAs. However, this strong innate immune response was down-regulated to almost negative when the hairpin containing 2'-O-methylated nucleotides was employed. It is expected that this result translates to siRNAs and long shRNAs. The sequences are shown in Table 11. Nucleotides forming the shRNA loops and 3' overhangs are shown in bold. Nucleotides with 2'-OM modification are underlined. Deoxyribonucleotides are indicated by lower-case letters. Phosphorothioate bonds are indicated by *.

Collectively, 2'-OMe modification efficiently remove the immunostimulating properties of sshRNAs.

TABLE 7a

Comparison of immunostimulatory properties of shRNAs with and without 2'-OMe modification

| | SG142 | | SG108 | | SG118 | |
|---|---|---|---|---|---|---|
| 2'-OMe | − | + | − | + | − | + |
| IFN-β | 1.54 ± 0.21 | 1.31 ± 0.13 | 27.77 ± 2.60 | 1.24 ± 0.25 | 192.24 ± 7.56 | 2.16 ± 0.51 |
| IL-6 | 2.79 ± 0.14 | 1.30 ± 0.06 | 4.16 ± 0.24 | 1.42 ± 0.13 | 21.49 ± 1.69 | 1.53 ± 0.16 |
| TNF-α | 7.72 ± 0.44 | 1.52 ± 0.38 | 19.29 ± 1.81 | 1.29 ± 0.36 | 548.36 ± 91.74 | 1.83 ± 0.59 |
| TLR3 | 4.26 ± 0.19 | 1.32 ± 0.10 | 17.31 ± 0.18 | 1.19 ± 0.21 | 67.59 ± 3.68 | 1.54 ± 0.04 |
| TLR7 | 1.54 ± 0.41 | 6.98 ± 2.98 | 3.53 ± 0.95 | 2.77 ± 1.01 | 6.52 ± 0.78 | 2.58 ± 1.19 |
| TLR8 | 1.39 ± 0.08 | 4.46 ± 1.70 | 5.38 ± 1.41 | 3.27 ± 0.26 | 5.32 ± 0.35 | — |
| RIG-I | 28.43 ± 10.18 | 2.76 ± 1.45 | 54.09 ± 18.48 | 11.63 ± 3.85 | 18.92 ± 8.48 | 3.91 ± 1.55 |
| PKR | 3.61 ± 0.35 | 1.20 ± 0.13 | 6.81 ± 0.57 | 1.08 ± 0.22 | 12.07 ± 2.16 | 1.15 ± 0.10 |

TABLE 7b

Comparison of immunostimulatory properties of shRNAs with and without 2'-OMe modification (continued)

| | PolyI:C | T7 transcribed sh68 | SG119 (blunt ended derivative of SG142) | |
|---|---|---|---|---|
| 2'-OMe | − | − | − | + |
| IFN-β | 25887.97 ± 1533.97 | 393.29 ± 35.13 | 7.28 ± 1.79 | 0.55 ± 0.12 |
| IL-6 | 1628.00 ± 163.34 | 83.06 ± 27.50 | 4.55 ± 1.44 | 0.88 ± 0.11 |
| TNF-α | 27213.81 ± 2536.83 | 318.66 ± 48.59 | 5.92 ± 2.79 | 1.32 ± 0.20 |
| TLR3 | 116.39 ± 4.58 | 94.69 ± 5.39 | 7.95 ± 0.93 | 1.09 ± 0.09 |
| TLR7 | 274.62 ± 36.69 | 7.84 ± 3.95 | 1.22 ± 0.44 | 0.25 ± 0.04 |
| TLR8 | 180.78 ± 40.64 | 4.08 ± 1.09 | 2.10 ± 0.35 | 0.48 ± 0.07 |
| RIG-I | 1058.79 ± 368.87 | 140.75 ± 34.93 | 289.21 ± 72.72 | 13.46 ± 6.08 |
| PKR | 54.6 ± 3.69 | 6.15 ± 2.16 | 4.32 ± 0.36 | 1.06 ± 0.21 |

100 nM sshRNAs with and without 2'-OMe modifications were transfected into human MRC-5 cells in triplicate. RNA was extracted from cells 24 hours post-transfection and quantitative RT-PCRs were performed. Cells without treatment was used as negative controls. The cells that received only the transfection reagent, lipofectamine 2000, showed no change in the levels of the tested genes. PolyI:C and T7-transcribed sh68 (having the same sequence as synthetic SG68) were used as positive controls and were transfected into cells in equivalent amounts by weight. The mean values and standard errors of the relative RNA levels (fold differences) of genes of interest were calculated and normalized to levels of GAPDH. The shRNAs with 2'-OMe all have the following pattern of modification except for SG119:

5'-NNNNNNNNNNNNNNNNNNNNNNNUUNNNNNNNNNNNNNNNNNNNNN-3'

(Underlined letters represent 2'-OMe modified nucleotides). The modified version of SG119 is SG235, shown in Table 2.

TABLE 8

Cytokine expression at 6 and 24 hours after shRNA transfection in MRC-5 cells

| | IFN-β | | TNF-α | |
|---|---|---|---|---|
| Time (h) | 6 | 24 | 6 | 24 |
| PolyI:C | 2031.45 ± 440.62 | 1092.63 ± 168.72 | 48972.85 ± 4878.69 | 104812.57 ± 11067.82 |
| SG142 | 2.05 ± 0.57 | 1.42 ± 0.20 | 0.54 ± 0.07 | 7.33 ± 2.19 |
| SG118 | 1.03 ± 0.18 | 72.55 ± 8.65 | 15.41 ± 6.87 | 7328.79 ± 768.16 |

100 nM sshRNAs and equivalent amounts by moles of phosphate of positive control (polyI:C) were transfected into human MRC-5 cells in triplicate. RNA was extracted from cells 6 and 24 hours post-transfection and quantitative RT-PCRs were performed. The mean values and standard errors of the relative RNA levels (fold differences) of genes of interest were calculated and normalized to levels of GAPDH.

TABLE 9

Immunostimulatory properties of shRNAs with various numbers of 2'-OMe modifications (measured 24 hours after transfection)

| | IFN-β | TNF-α |
|---|---|---|
| SG118 (no 2'-OMe) | 33.58 ± 1.43 | 2426.48 ± 364.31 |
| SG239 (2 nt 2'-OMe) | 0.92 ± 0.17 | 1.93 ± 1.05 |
| SG240 (4 nt 2'-OMe) | 1.40 ± 0.20 | 0.55 ± 0.24 |
| SG241 (6 nt 2'-OMe) | 2.75 ± 0.43 | 0.45 ± 0.20 |

100 nM sshRNAs with and without 2'-OMe modification were transfected into human MRC-5 cells in triplicate. RNA was extracted from cells 24 hours post-transfection and quantitative RT-PCRs were performed. The mean values and standard errors of the relative RNA levels (fold differences) of genes of interest were calculated and normalized to levels of GAPDH.

TABLE 10

2'-O-Me modification can greatly reduce the innate immune response triggered by certain other modifications of sshRNAs

| | 5' conjugation | 3' conjugation | | C3C3 loop | phosphorothioate bond | |
|---|---|---|---|---|---|---|
| 2'-OMe | –(SG143) | –(SG144) | +(SG222) | SG229 | –(SG211) | +(SG212) |
| IFN-β | 0.03 ± 0.00 | 84.27 ± 6.65 | 0.21 ± 0.03 | 869.06 ± 76.12 | 592.28 ± 50.37 | 1.53 ± 0.58 |
| IL-6 | | 10.83 ± 1.38 | 0.89 ± 0.08 | 24.25 ± 2.76 | 150.68 ± 33.19 | 1.41 ± 0.08 |
| TNF-α | 6.27 ± 1.71 | 91.80 ± 23.70 | 1.09 ± 0.05 | 50.03 ± 6.36 | 605.54 ± 94.13 | 1.86 ± 0.24 |
| TLR3 | | 28.63 ± 2.58 | 0.99 ± 0.09 | 39.85 ± 1.06 | 108.43 ± 7.64 | 1.32 ± 0.10 |
| TLR7 | | 3.46 ± 2.37 | 0.25 ± 0.04 | 10.68 ± 2.47 | 21.77 ± 6.85 | 6.98 ± 2.98 |
| TLR8 | | 3.54 ± 1.16 | 0.21 ± 0.07 | 7.69 ± 2.08 | 21.32 ± 8.98 | 4.46 ± 1.70 |
| RIG-I | | 1309.62 ± 122.27 | 15.46 ± 2.51 | 83.24 ± 10.13 | 117.90 ± 14.93 | 2.76 ± 1.45 |
| PKR | | 5.89 ± 0.78 | 0.00 ± 0.00 | 7.67 ± 0.25 | 8.93 ± 0.58 | 1.20 ± 0.13 |

100 nM sshRNAs with and without 2'-OMe modifications were transfected into human MRC-5 cells in triplicate. RNA was extracted from cells 24 hours post-transfection and quantitative RT-PCRs were performed. Cells without treatment were used as negative controls. The cells that received only the transfection reagent, Lipofectamine 2000, showed no change in the levels of the tested genes. Poly(I:C) and T7-transcribed sh68 (having the same sequence as synthetic SG68) were used as positive controls and were transfected into cells in equivalent amounts by weight. The mean values and standard errors of the relative RNA levels (fold differences) of genes of interest were calculated and normalized to levels of GAPDH.

TABLE 11

Additional shRNA sequences used in Example 8

| Sequence ID# | Sequence (5'-3') | Target position on IRES | shRNA abbrev | IC$_{50}$ (pM) |
|---|---|---|---|---|
| SEQ ID NO: 32 | UGA GGU UUA GGA UUC GUG CUU GCA CGA AUC CUA AAC CUC A-C3-S-S | 346-364 | SG144 | 4.8 |
| SEQ ID NO: 41 | UGA GGU UUA GGA UUC GUG CUU GCA CGA AUC CUA AAC CUC A-C3-S-S | 346-364 | SG222 | (58.0)* |

*Estimated from dose response curve

Example 9: Target Knock-Down Seen in 293FT Cells is not Due to IFN Stimulation The induction of type I IFN can down-regulate the expression of multiple genes in a nonspecific manner. To test whether this affects the target gene knockdown experiments that were performed in 293FT cells, shRNAs were transfected into 293FT cells, and 24 hours later, total RNAs were extracted to measure cytokine mRNA levels. As shown in Table 12, IFN-β was not induced in the cells that received SG118 and SG117 (SEQ ID NO: 42, 5'-UGA GGU UUA GGA UUC GUG CUU GCA CGA AUC CUA AAC CUC A-3', target position 346-364) whereas positive in the cells that were transfected with polyI:C. In addition, only RIG-I was upregulated in 293FT cells after polyI:C was transfected (the relative fold difference between polyI:C treated and untreated is 322.98±7.52). The expressions level of TLRs and PKR were negligible in 293FT cells (TLR3: 6.50±1.74; TLR7: 3.75±2.15; TLR8: 7.39±5.18; PKR: 7.50±1.48) but high in MRC-5 cells (Table 7b) in polyI:C transfected groups. This indicates that 293FT cells were deficient in TLR3, TLR7, TLR8, and PKR expression or in some gene(s) that lead to the transcription of TLR3, TLR7, TLR8, and PKR. In the previous experiment, SG118 induced the upregulation of IFN-β, TNF-α, TLR3, RIG-I, and PKR expression in MRC-5 cells. It is reasonable to think that the lack of IFN-β expression in 293FT cells when transfected with SG118 is due to the lack of responding machineries of TLR3 and PKR. Similarly, SG117 induced the upregulation of IFN-β expression in MRC-5 cells but not in 293FT cells.

TABLE 12

Induction of cytokines by shRNAs in 293FT cells

|  | PolyI:C | SG117 | SG118 |
| --- | --- | --- | --- |
| IFN-β | 5797.98 ± 150.07 | 3.64 ± 2.78 | 2.51 ± 2.08 |
| IL-6 | 53.20 ± 22.40 | Not measured | Not measured |
| TNF-α | 3379.65 ± 332.74 | Not measured | Not measured |

100 nM unmodified sshRNAs and equivalent amount of positive control (polyI:C) were transfected into 293FT cells in triplicate. RNA was extracted from cells 24 hours post-transfection and quantitative RT-PCRs were performed. The mean values and standard errors of the relative RNA levels (fold differences) of cytokine genes were calculated and normalized to levels of GAPDH.

Example 10: Importance of Eliminating Dimers of shRNAs for Avoiding Immune Stimulation Chemically synthesized shRNAs could be presented as mainly monomer (after the treatment of heating the shRNA at 95° C. for 4 minutes and snap cooling it in ice-water bath) or a mixture of monomer, dimer, and trimer in solution. The previous cytokine expression studies were all performed with shRNAs in a mixed conformation (without heating and snap cooling) although the target gene knockdown experiments were performed using shRNAs after heating and snap cooling. We thus tested whether the immunostimulatory property comes from dimer or monomer. The sshRNAs that induced IFN-β expression when in mixed isomers were selected, heated and snap cooled to become mainly monomers, and introduced into MRC-5 cells. Surprisingly, sshRNAs in monomer form induced much less cytokines compared to the ones without heating and snap cooling (Table 13). This indicates that the length of the duplex may play a role in the recognition by inflammatory mediators. However, the length may not be the sole player here since SG142, in the mixture of dimer and monomer, is still negative in cytokine induction (Table 7a).

100 nM unmodified sshRNAs with and without 95° C. heating (4 min) and snap cooling, and equivalent amount of positive control (polyI:C) were transfected into MRC5 cells in triplicate. RNA was extracted from cells 24 hours post-transfection and quantitative RT-PCRs were performed. The mean values and standard errors of the relative RNA levels (fold differences) of cytokine genes were calculated and normalized to levels of GAPDH.

Example 11: Mechanism of Action Study with Modified sshRNAs

Figure 9:
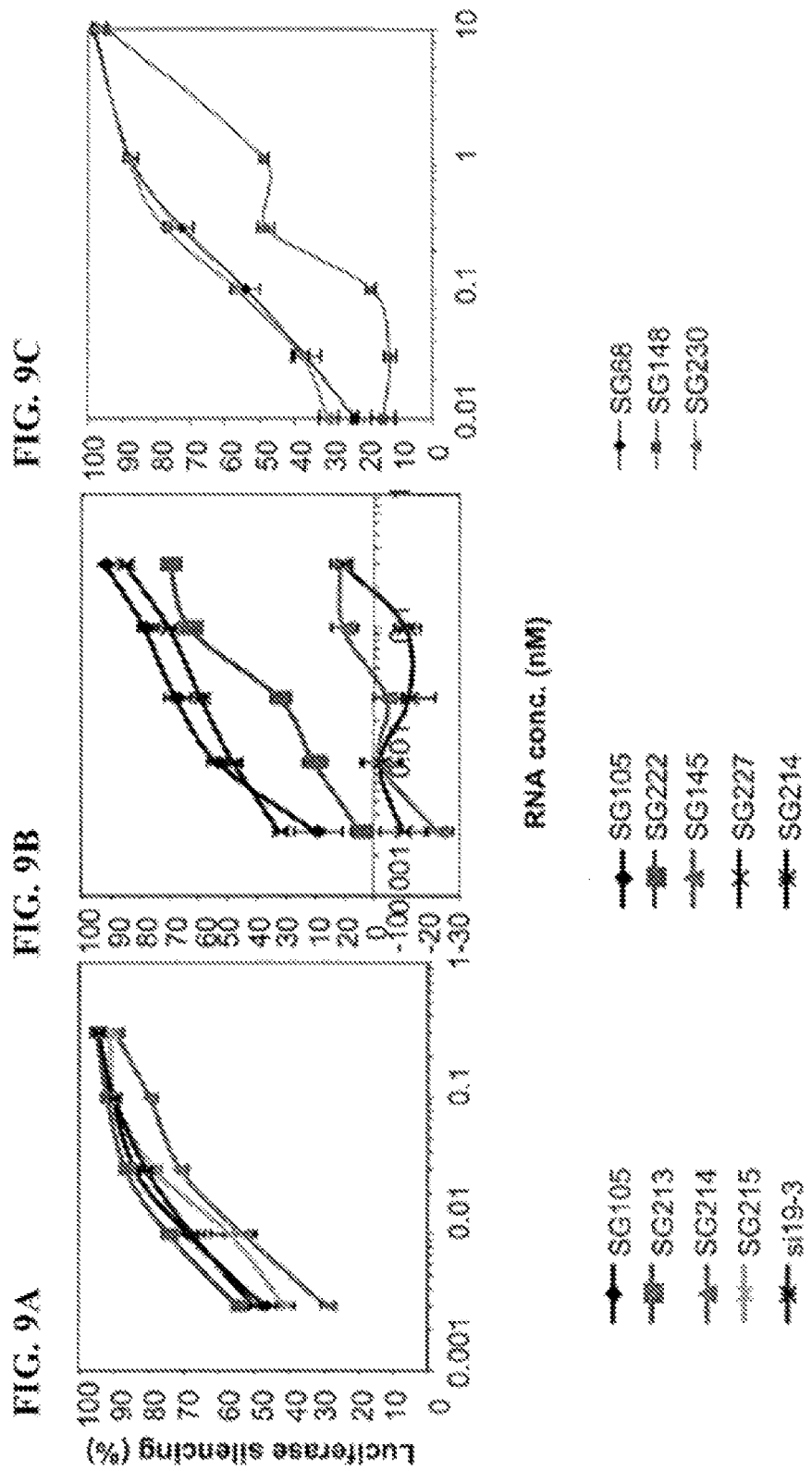
FIG. 9 depicts the potency of L and R sshRNAs with modifications or mismatch on the sense sequence (see Example 11). L sshRNAs are shown in FIGS. 9A and 9B; R sshRNAs are shown in FIG. 9C. The results indicate that the processing of L and R sshRNAs may be different. The slicing of the sense sequence by Ago2 may enhance the RNAi activity of L but not R sshRNAs.

Unlike commonly used shRNAs that have a stem length of 21-nt or longer and require Dicer processing before being loaded into RISC, sshRNAs with a stem length of 19-nt or less are not Dicer substrate in vitro. To understand how sshRNAs are processed in the cells before initiating RNAi function, a group of modified sshRNAs was examined. As shown in Table 14, FIG. 9, phosphorothioate bonds were added at various positions on the sense sequence in an attempt to study whether the sense sequence will be cleaved by the slicing function of Ago2 and if it is, at what position the cleavage will occur. The experiments were performed as described in FIG. 1. A slight decrease in $IC_{50}$ was seen when the ps bonds were added in the middle of the sense sequence of an L sshRNA (FIG. 9A). To elucidate further the position of the cleavage, combined modifications of 2'-OMe modification and PS bonds were added to the $11^{th}$ nucleotide from the 3' end and a more severe decrease of target knockdown efficacy was observed (SG222, FIG. 9B). Furthermore, an sshRNA with deoxynucleotides in the entire sense sequence or an sshRNA with 4-nt mismatches in the middle of the sense sequence had no RNAi activity. These results indicate that a cleavage between the $10^{th}$ and the $11^{th}$ nucleotides from the 3' end of the sense sequence may be required for efficient target knockdown. A modification such as the combination of 2'-OMe and PS bonds, or deoxynucleotide will block this cleavage and reduce the silencing. For R sshRNA, no activity loss was seen when similar 2'-OMe modification and ps bonds were placed on the sense sequence (SG230, FIG. 9C). However, 4-nt mismatch in the middle of the sense sequence significantly reduced but not completely removed the activity of R sshRNA (SG148, FIG. 9C). These results suggest that the processing of R sshRNA is probably different from that of L sshRNA.

The sequences of these shRNAs are shown in Table 14. Nucleotides forming the shRNA loops and 3' overhangs are shown in bold. Deoxyribonucleotides are indicated by

TABLE 13

Inflammatory cytokine induction by sshRNAs with and without heating and snap cooling

| Heating/snap | IFN-β | | TNF-α | |
| --- | --- | --- | --- | --- |
| cooling | − | + | − | + |
| SG105 | 47.53 ± 0.35 | 5.03 ± 0.62 | 6192.23 ± 2422.52 | 319.25 ± 81.48 |
| SG117 | 23.11 ± 2.69 | 4.61 ± 0.68 | 2551.56 ± 73.10 | 194.85 ± 36.78 |
| SG119 | 7.28 ± 1.79 | 2.59 ± 0.63 | 5.92 ± 2.79 | 5.44 ± 2.09 |
| SG118 | 33.58 ± 1.43 | 2.23 ± 0.22 | 2426.48 ± 364.31 | 2.84 ± 1.03 |
| SG144 | 88.59 ± 10.97 | 53.05 ± 1.76 | 15424.02 ± 7040.57 | 7863.85 ± 635.85 |
| SG211 | 37.70 ± 2.08 | 22.05 ± 1.08 | 6683.48 ± 667.70 | 7735.61 ± 1113.55 |
| SG229 | 48.11 ± 4.91 | 0.16 ± 0.01 | 9247.23 ± 1143.46 | 32.02 ± 11.51 | lower-case letters. Phosphorothioate bonds are indicated by *. Mismatches made at the sense sequence is shown in Italic.

identical, these results further indicate that Dicer processing is not needed for the activity of sshRNAs.

TABLE 14

Listing of shRNA Sequences Targeting HCV IRES Used in Example 11.

| Sequence ID# | Sequence (5'-3') | Target position on IRES | shRNA abbrev | $IC_{50}$ (pM)* |
|---|---|---|---|---|
| SEQ ID NO: 1 | UGA GGU UUA GGA UUC GUG CUU GCA CGA AUC CUA AAC CUC A | 346-364 | SG105 | 3.5 |
| SEQ ID NO: 43 | UGA GGU UUA GGA UUC GUG CUU GCA CG*A* A*UC CUA AAC CUC A | 346-364 | SG213 | 2.3 |
| SEQ ID NO: 44 | UGA GGU UUA GGA UUC GUG CUU GCA CGA AU*G* C*UA AAC CUC A | 346-364 | SG214 | 9.8 |
| SEQ ID NO: 45 | UGA GGU UUA GGA UUC GUG CUU GCA CGA AUC CU*A* A*AC CUC A | 346-364 | SG215 | 5.7 |
| SEQ ID NO: 46 | UGA GGU UUA GGA UUC GUG CUU GCA CGA AU<u>C</u>* CUA AAC CUC A | 346-364 | SG222 | 72.8 |
| SEQ ID NO: 48 | UGA GGU UUA GGA UUC GUG CUU GCA CGA ACA AGA AAC CUC A | 346-364 | SG145 | N/A |
| SEQ ID NO: 49 | UGA GGU UUA GGA UUC GUG CUU gca cga atc cta aac ctc a | 346-364 | SG227 | N/A |
| SEQ ID NO: 25 | GCA CGA AUC CUA AAC CUC ACA AUA UGA GGU UUA GGA UUC GUG CUU | 346-364 | SG68 | 33.7 |
| SEQ ID NO: 50 | GCA CGA ACA AGA AAC CUC ACA AUA UGA GGU UUA GGA UUC GUG CUU | 346-364 | SG148 | (1000) |
| SEQ ID NO: 51 | GCA CGA AU<u>C</u>* CUA AAC CUC ACA AUA UGA GGU UUA GGA UUC GUG CUU | 346-364 | SG230 | (68.5) |

*IC50 values are based on dose response curves generated in 293FT cells; those in parentheses are estimated, others are calculated as in Example 1.

Figure 10:
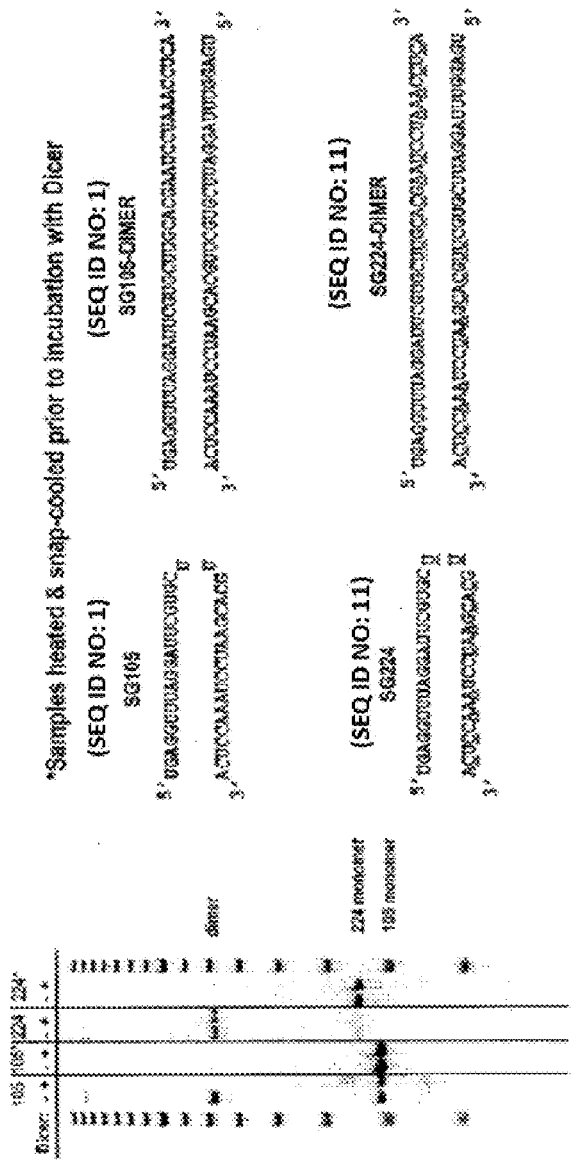
FIG. 10 shows that a 2'-O-Me-modified sshRNA is not a Dicer substrate in vitro (see Example 12). sshRNAs SG105 and SG224 were subjected to recombinant Dicer treatment as indicated with (*) or without heating and snap cooling prior to Dicer treatment. 8 pmol of each synthetic sshRNA was incubated in a 10 μL reaction in the presence of 1 U of recombinant Dicer enzyme (Stratagene) and buffer containing 150 mM NaCl, 20 mM Tris-HCl (pH 8), and 2.5 mM $MgCl_2$ for 18 hours at 37° C. (lanes labeled +). Control reactions that contained each sshRNA but lacked Dicer were incubated in parallel (lanes indicated by −). Outer lanes contained 10-bp DNA ladders. Samples were analyzed by 10% non-denaturing PAGE with SYBR Gold staining. Dicer cleaves the unmodified dimers and trimers but not their 2'-O-Me-modified versions. Neither unmodified nor 2'-O-Me-modified monomer hairpins are dicer substrates in vitro.
Figure 11:
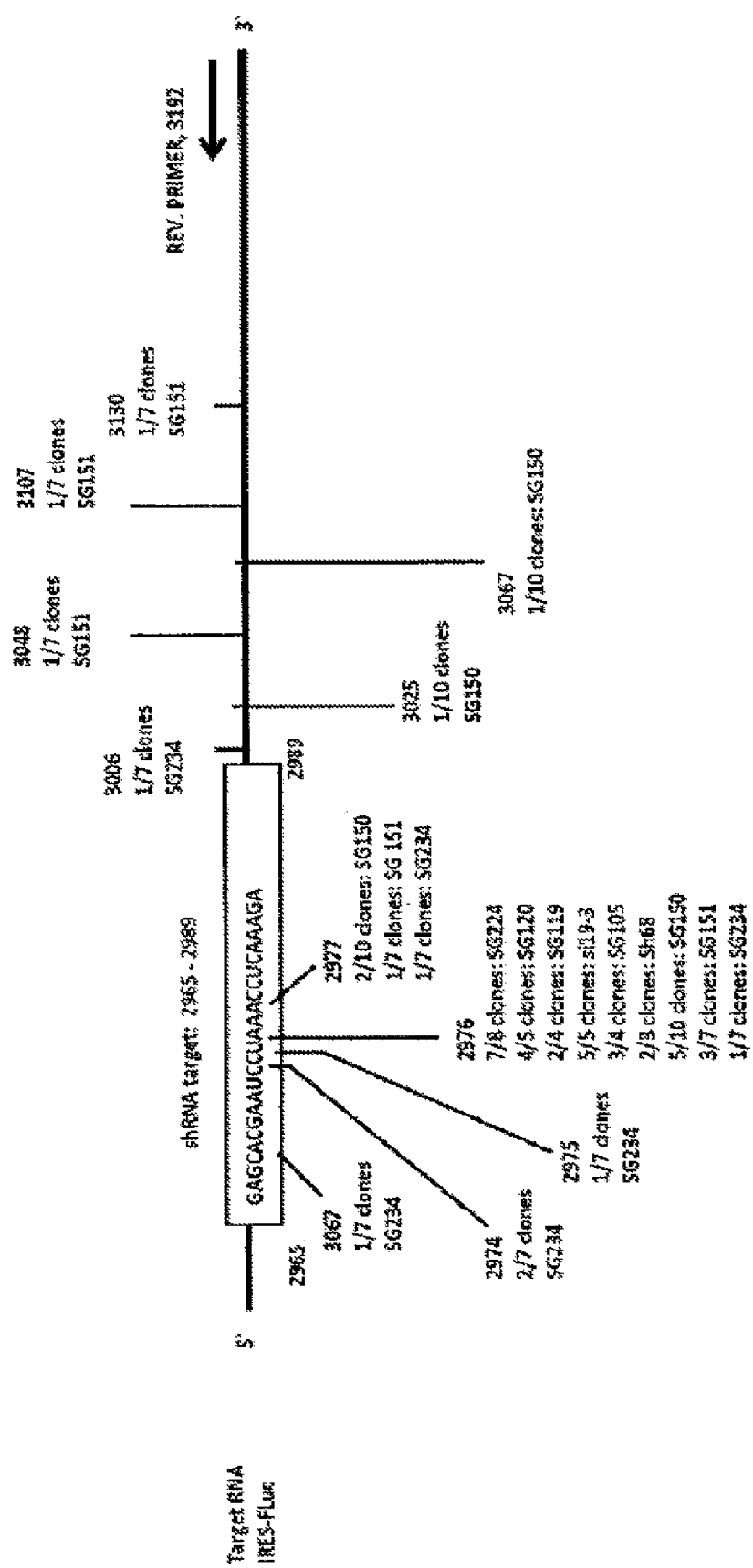
FIG. 11 depicts the positions of cleavage of mRNA targets by modified sshRNAs (see Example 13). 293FT cells were transfected with siRNA or sshRNA together with pSG154m target expression plasmid (see Example 1 for description). Total RNA was extracted 12 hours post transfection and mRNA was purified by the Oligotex mRNA kit (Qiagen, Germantown, Md.). The mRNA was then subjected to a modified 5'-RACE (rapid amplification of cDNA ends) analysis using the GeneRacer Kit (Invitrogen) following the manufacturer's instructions (Soutschek et al. 2004). Briefly, GeneRacer RNA adaptor (Invitrogen) was ligated to mRNAs at their 5' ends. Ligated RNAs were reverse transcribed using the primer 5'-CGCGCCCAACACCG-GCATAAAGAATT-3' (SEQ ID NO: 71) and amplified by PCR using primers 5'-GCTTCTGCCAACCGAACGGA-CATTT-3' (SEQ ID NO: 72) and (adaptor specific) 5'-CGACTGGAGCACGAGGACACTGA-3' (SEQ ID NO: 71. PCR was started with 5 cycles of 95° C. for 45 seconds (sec) and 72° C. for 30 sec, followed by 5 cycles of 95° C. for 45 sec and 69° C. for 30 sec, then by 25 cycles of 95° C. for 45 sec, 65° C. for 30 sec, and 72° C. for 30 sec. The PCR products were analyzed on a 2% agarose gel and the band with the predicted length of the cleavage product was then excised, purified, cloned and sequenced. A diagrammatic representation of the portion of interest of the target mRNA is shown indicating the shRNA target site (nt 2965-nt 2989) and the priming position of the Reverse primer used for 5'-RACE. The various cleavage sites (and the number of clones obtained for each) for all the sshRNAs used in this study are indicated.

Example 12: 2'-O-Me-Modified sshRNAs are not Dicer Substrates In Vitro sshRNAs can adapt both monomeric hairpin and higher order multimer conformations (mainly dimers) in solution (FIG. 10, lanes labeled (−)). When the sshRNAs are heated to 95° C. for 4 minutes and quickly cooled in an ice bath (snap cooling), the multimeric sshRNAs are quantitatively converted to monomer hairpins (FIG. 10, lanes 105*(−) and 224*(−)). To examine whether 2'-O-Me-modified sshRNA in either monomer or dimer form can be substrates for Dicer, we incubated SG224, which has alternating 2'-O-Me modifications in the passenger strand and both uridine residues in the loop, with recombinant Dicer in vitro. In parallel, we performed in vitro Dicer cleavage reactions with SG105, a molecule with the same sequence as SG224 but lacking any 2'-O-Me modifications. The dimer conformation of both SG105 and SG224 consists of two 19 bp duplexes surrounding two central U—U mismatches. Both SG105 and SG224 monomer hairpins are not cleaved by dicer in vitro (FIG. 10, lanes 105*(+) and 224*(+)), which supports a dicer-independent mechanism for activity of sshRNAs. Although Dicer does not appear to be involved in processing monomer sshRNAs, the dimer conformation of SG105 can be cleaved by recombinant Dicer in vitro (FIG. 10, 105(+)). However, dimers of SG224 were found not to be Dicer substrates in vitro (FIG. 10, 224(+)). The presence of 2'-O-Me groups appears to block cleavage of the SG224 dimer. Considering that the dose response curves of SG105 and SG224 before and after the heat and snap-cool treatment were almost Example 13: Specific Target Cleavage by sshRNAs To verify whether the observed gene suppression by sshRNAs is due to RNAi-directed cleavage, a modified 5'-RACE (rapid amplification of cDNA ends) procedure (Soutschek et al. 2004) was performed to identify the specific cleavage site of the target mRNA (see legend to FIG. 11 for details). This site is expected to be ten nucleotides downstream of the 5' end of the guide strand (Rana 2007). As shown in FIG. 11, cleavage occurs at this position in the majority of clones for all left hand loop sshRNAs including SG224, SG105, SG119, SG120, and SG68. These results strongly support the involvement of the RNAi machinery in sshRNA-mediated gene knockdown. For right hand loop sshRNAs (SG150, SG151, shown in Table 15 below) including one that has a phosphorothioate-modified loop (SG234), the target is also cleaved although the cleavage occurs at multiple sites within and surrounding the target sequence.

TABLE 15

Listing of shRNA Sequences Targeting HCV IRES used in Example 13

| Sequence ID# | Sequence (5'-3') | Target position on IRES | shRNA abbrev |
|---|---|---|---|
| SEQ ID NO: 69 | GCA CGA AUC CUA AAC CUC AUU UGA GGU UUA GGA UUC GUG CUU | 346-364 | SG150 |

TABLE 15 -continued

Listing of shRNA Sequences Targeting HCV
IRES used in Example 13

| Sequence ID# | Sequence (5'-3') | Target position on IRES | shRNA abbrev |
|---|---|---|---|
| SEQ ID NO: 70 | GCA CGA AUC CUA AAC CU UGA GGU UUA GGA UUC GUG CUU | 346-364 | SG151 |

Nucleotides forming the shRNA loops and 3' overhangs are shown in bold.

Example 14: Stable Binding of shRNAs to Human Ago2 and Ago1

Since we established that L sshRNAs are not cleaved by Dicer in vitro and chemical modification of the hairpin loop does not reduce their potencies, we hypothesize that the entire L sshRNA may be loaded to Ago2-containing RISC. In this proposed mechanism, Ago2 slices the sense sequence between 10 and 11 nt from the 5' phosphate of the antisense sequence, facilitating the dissociation and/or degradation of the 3' half of the sense sequence. As an alternative, the duplex may be opened by an ATP-dependent helicase (Robb & Rana, 2007). Thus, two RNA products may be expected in the Ago2 complex: a full-length hairpin and a hairpin that contains the antisense sequence, loop, and half of the sense strand. Indeed, in Ago2 pull-down experiments, two bands were seen in the sample that received the 40-nt L sshRNA SG224, corresponding to the full length sshRNA and an sshRNA lacking half (10-nt) of the sense strand (FIG. 12A). The positive control shRNA sh1, which has a 25-bp stem, gave a single product of a size less than 25 nt in the fraction immunoprecipitated with the Ago2 antibody (FIG. 12A), consistent with Dicer processing and loss of the loop.

Further confirmation that the passenger strand can be cleaved in an L-type sshRNA-Ago2 complex was shown in a subsequent experiment (FIG. 12B), where a labeled 38-nt sshRNA, SG119, resulted in both a full-length product (38 nt) and a 10-nt shorter product (28 nt) associated with Ago2. For both SG224 and SG119, the major band associated with Ago2 was the 10-nt shorter band, indicating that virtually all of the hairpins are converted into the sliced product once bound to Ago2. In addition, when the passenger strand has either mismatches (SG145) or chemical modifications (SG222) at the slicer cleavage site, only full-length sshRNA is associated with the Ago complex (FIG. 12B). As a negative control, an unrelated 38 nt aptamer RNA that binds malachite green showed no association with Ago2, as expected (FIG. 12B).

To examine whether right hand loop (R) sshRNAs were also loaded into Ago2 and processed at the slicer site of the passenger strand, Ago2 pull-down experiments were performed with 3'-end-labeled sshRNAs. Interestingly, neither full length nor processed R sshRNAs were observed in immunoprecipitated Ago2 complexes (FIG. 12C, SG68 and SG148). In addition, a 3'-end labeled L sshRNA was not pulled down by Ago2. This is presumably because the L sshRNA is largely sliced (as seen in FIGS. 12A and 12B), and the resulting 10-nt 3'-labeled fragment dissociates from Ago2 and is degraded. However, when the supernatant fractions not in complex with Ago2 antibodies ("unbound fraction") were examined by denaturing PAGE (FIG. 12D), an RNA band of length predicted for cleavage at the slicer site of the passenger strand of right hand loop SG68 was detected (FIG. 12D, 3'-SG68-UB). Consistent with the L sshRNAs, when the slicer site of the passenger strand of an R sshRNA has mismatches to the guide strand (SG148), the passenger strand is not cleaved at the slicer site. In the "unbound" fraction of both SG68 and SG148, there is a band of about 23 nt that is consistent with cleavage in the loop, suggesting that an alternate processing pathway is available to these molecules. These sshRNAs have an unmodified 5 nt loop (CAAUA) that contains two pyrimidine-A sequences that could be susceptible to cleavage by a ribonuclease. For molecules with this loop sequence, the hairpin can be converted to an siRNA by endonucleolytic cleavage of the loop. The resulting duplex might then be unwound by a helicase. Indeed, the activity of an R sshRNA with four mismatches around the slicing site (SG148) was only partially reduced (FIG. 9C), suggesting that the mechanism of duplex separation for this R sshRNA is different from that for an sshRNA with the dinucleotide UU loop (SG224) since cleavage of 2-nt loops is not observed, even in the absence of chemical modification in the loop. A nominally L-type shRNA such as SG224 can act as an R-type if the 3' half of the hairpin is recognized as the guide strand, and this was indeed observed upon 3'-end labeling: a ~30-nt fragment was observed, but only in the unbound fraction (3'SG224-UB, FIG. 12D); as with other R-type shRNAs this processing product does not stably associate with Ago2.

Figure 12:
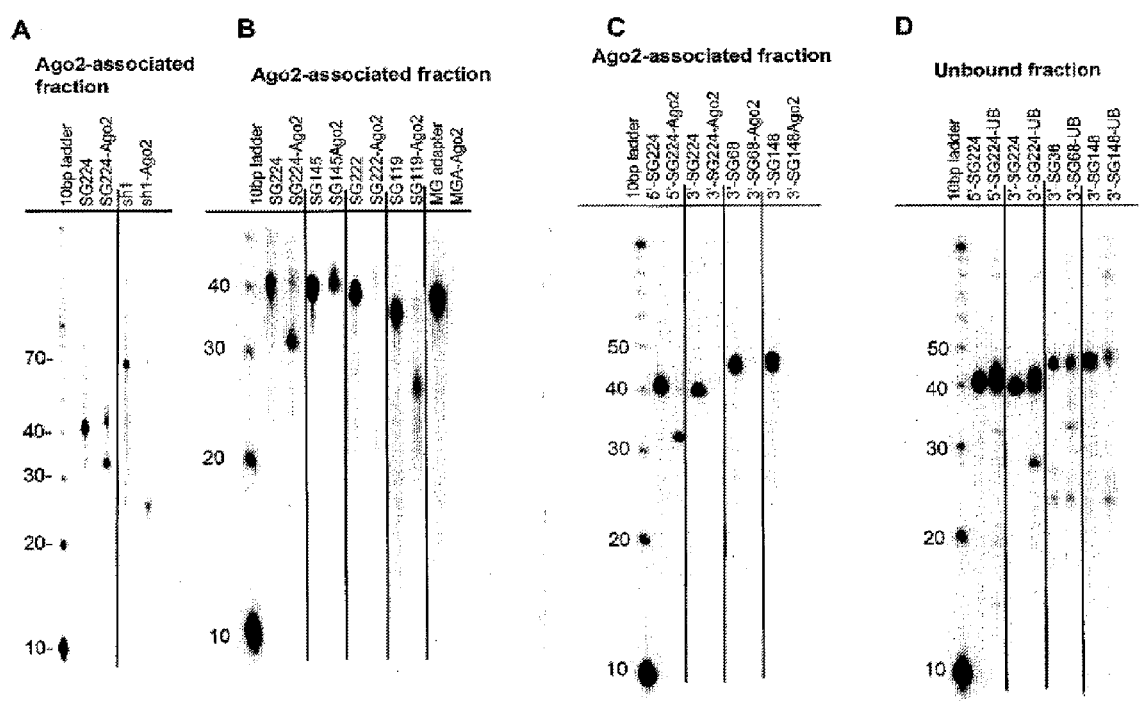
FIG. 12 depicts an immunoprecipitation analysis of RNA species that become stably associated with human Ago2 after transfection of labeled sshRNAs (see Example 14). sshRNAs were radio-labeled either at the 5' end or 3'-end as indicated and transfected into 293FT cells. Six hours later, the cells were lysed and were incubated with mouse anti-human Ago2 antibody (Wako) for 16 hours at 4° C. The RNAs purified from the antibody-bound complexes were then analyzed by 12% denaturing PAGE. Each gel shows the end-labeled shRNA alone and the shRNA pulled down by the Ago2 antibody (labeled shRNA-Ago2). Panel A depicts a comparison of Ago2-associated RNAs from SG224, a left hand (L) sshRNA that is not a dicer substrate, and sh1, an lshRNA, which is a dicer substrate. For SG224, a 30 nt RNA fragment that is consistent with the product expected from cleavage of the passenger strand by Ago2 is observed (lane 2, SG224-Ago2) whereas there is no cleavage in the loop. In contrast, sh1, which has a 25-bp stem, has a single product with a size less than 25 nt in the fraction immunoprecipitated with the Ago2 antibody (lane 4, sh1-Ago2), consistent with Dicer processing and loss of the loop. Panel B depicts the effect of blocking cleavage at the slicer site on association with Ago2. The 5'-end-labeled sshRNA SG119, a 38-mer, produced both a full-length band (38 nt) and a 10-nt shorter band (28 nt) associated with Ago2. In addition, when the passenger strand had either mismatches (SG145) or chemical modifications (SG222) at the slicer cleavage site (see Table 14), only full-length sshRNA was associated with the Ago complex. As a negative control, an unrelated 38 nt aptamer RNA that binds malachite green showed no association with Ago2, as expected. Panel C depicts the association of R-type sshRNAs with Ago2. In contrast to L-type SG224, the 3'-end-labeled R-type shRNAs SG68 and SG148 (an R sshRNA having mismatches around the passenger strand cleavage site) were not pulled down by Ago2 immunoprecipitation (compare 5'SG224-Ago2 with 3'SG68-Ago2, and 3'SG148-Ago2). Labeling SG224 at the 3' end also allows testing of whether any slicing of the antisense sequence (which would be the guide strand if it were recognized as an R-type shRNA) occurs. Panel D depicts an analysis of the unbound fraction in Ago2 pull-down experiments. The supernatants of the lysates that were not bound to antibody were also collected, phenol-CHCl$_3$ extracted and analyzed by 12% denaturing PAGE. In each pair of lanes, the left-hand lane is the labeled RNA starting material and the right-hand lane (UB) is the RNA isolated from the unbound fraction. The product of guide strand cleavage at the slicer site is seen for both L and R-type shRNAs (3'SG224-UB, SG68-UB). However, SG148, with internal mismatches at the slicer site, is not cleaved (SG148-UB right panel). In the supernatants of both SG68 and SG148, which have a 5 nt loop, a 22-23 nt product that is consistent with cleavage in the loop is observed, indicating another pathway for hairpin opening (SG68-UB and SG148-UB). However, no loop cleavage is seen for SG224 with its compact UU loop.
Figure 13:
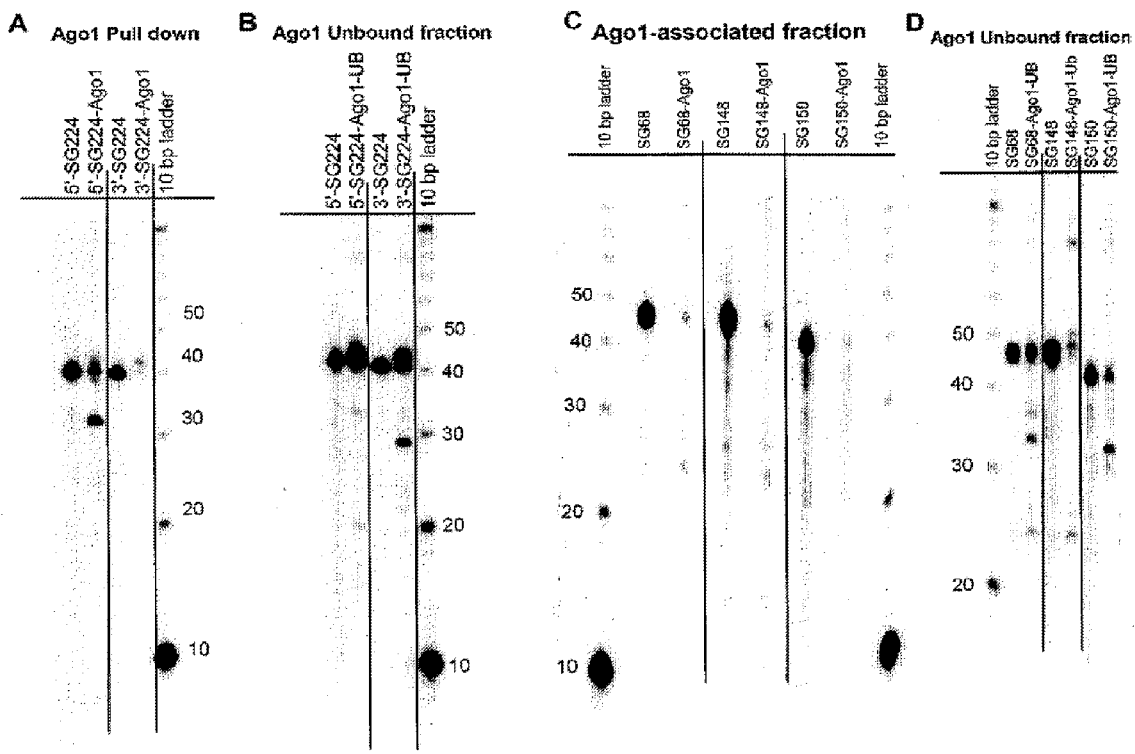
FIG. 13 depicts an immunoprecipitation analysis of RNA species that become stably associated with human Ago1 after transfection of labeled L and R sshRNAs (see Example 14). sshRNAs were $^{32}$P-labeled at the 5' or 3'-end as indicated and transfected into 293FT cells. Six hours later, the cells were lysed and then incubated with mouse anti-human Ago1 antibody (Wako). The RNAs purified from the antibody-bound complexes were then analyzed by 12% denaturing PAGE (panels A and C). The supernatants of the lysates that were not bound to antibody were also collected, phenol-CHCl$_3$ extracted and analyzed by 12% denaturing PAGE (B and D). Both full length and passenger strand-cleaved SG224 were pulled down with antibodies against Ago1 (5'-SG224-Ago1, panel A), consistent with Ago1-mediated cleavage of the passenger strand. In the unbound supernatant fraction (13B), an RNA consistent with cleavage 10 nt from the 5'-end of SG224 in the guide strand is observed when SG224 is 3'end-labeled although it is not observed in the pull down fraction (compare 3'SG224-Ago1UB (13B)) with 3'SG224-Ago1 (13A). For right hand loop shRNAs, only full-length sshRNA was found associated with Ago1 (13C, SG68-Ago1, SG148-Ago1, and SG150-Ago1). In the supernatant "unbound" fraction, cleavage of the passenger strand at the purported slicer site was observed for SG68 and SG150 (SG68-Ago1-UB and SG150-Ago1-UB, 13D). SG148, a molecule with 4 mismatches around the slicer site, is not cleaved in the passenger strand (SG148-Ago1-UB). Bands consistent with cleavage in the 5-nt loops of SG68 and SG148 (~23nt) were observed (13D, SG68-Ago1-UB and SG148-Ago1-UB) in the supernatant whereas no cleavage is observed for SG150, which has a dinucleotide UU loop (SG150-Ago1-UB).

FIG. 13 shows the results of pull down experiments that were performed with anti-Ago1 antibodies. For L sshRNA SG224, both full length and a 30 nt RNA consistent with cleavage 10 nt from 3'-end of the passenger strand were detected by denaturing PAGE analysis (FIG. 13A) although the extent of passenger strand cleavage was not as complete as with Ago2 (FIG. 12). These data are consistent with the results of Novina and colleagues, who showed that both Ago1 and Ago2 were capable of passenger strand cleavage of model miRNA duplexes in a cell-free system (Wang et al 2009). This is strong support that both Ago1 and Ago2 are capable of processing L sshRNAs in a dicer-cleavage independent mechanism. As in the Ago2 pull-down experiment, guide strand cleavage of SG224 was observed in the "unbound" fraction for 3'-end-labeled sshRNA (FIG. 13B), but this fragment is not stably associated with Ago1 (FIG. 13A) or Ago2 (FIG. 12C). For R sshRNAs SG68, SG148, and SG150, a weak band corresponding to full-length sshRNA is associated with Ago1 (FIG. 13C). In denaturing PAGE analysis of the "unbound" fraction (FIG. 13D), both passenger strand cleavage at the slicer site is observed for R sshRNAs SG68 and SG150, but not for SG148, which has mismatches at those positions. Cleavage of the 5-nt unmodified loop is observed for SG68 and SG148 in the "unbound" fraction (FIG. 13D) whereas the unmodified dinucleotide UU loop of SG150 is not cleaved (FIG. 13D). Since SG68 and SG150 have similar potency in target knockdown, we conclude that, for R as well as L sshRNAs, cleavage of the hairpin loop is not a requirement for silencing activity.

Figure 14:
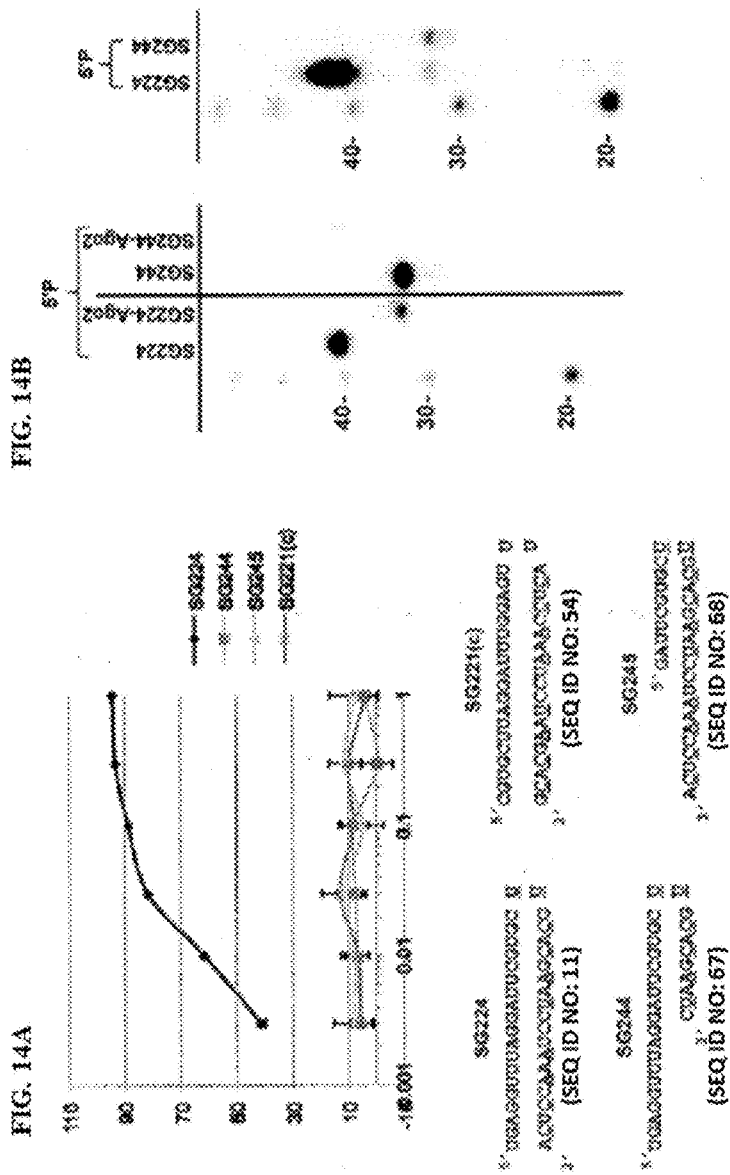
FIG. 14 shows that transfected, synthetic "pre-sliced" sshRNAs do not inhibit target expression and are not immunoprecipitated by Ago2-antibodies (see Example 15). Panel A shows the activity of the RNAs that would be produced upon Ago2 or Ago1 cleavage of either the passenger strand (SG244) or the guide strand (SG245), as measured by luciferase knock-down. The experiment was performed as described in FIG. 1. The results show that neither SG244 nor SG245 inhibits target expression. Panel B shows the results of transfections and subsequent Ago2 pull-down assays for 5'-end labeled SG224 and SG244, performed as described in the legend to FIG. 12. SG244, a 30-nucleotide RNA that corresponds to the expected product of passenger strand cleavage at the slicer site of SG224, is not pulled down in association with Ago2 (FIG. 14B, left panel, SG244-Ago2). The 30 nt RNA is present in the supernatant after incubation with hAgo2 antibodies (FIG. 14B, right panel, SG244). Thus, synthetic "pre-sliced" RNA is not loaded into RISC, which is consistent with its inactivity in knockdown of target expression.

Example 15: Transfected, Synthetic "Pre-Sliced" sshRNAs do not Inhibit Target Expression and are not Immunoprecipitated by hAgo2-Antibodies In a dose-response experiment performed as described in Example 1, we tested the activity of synthetic sshRNAs that were designed to be the same sequence of the product of cleavage of SG224 at either the passenger strand slicer site (SG244) or the guide strand cleavage site (SG245). These "pre-sliced" sshRNAs were transfected into 293FT cells in parallel with SG224, the parent molecule, and negative control SG221(c), a non-specific scrambled sshRNA. The results, shown in FIG. 14A, show that "pre-sliced" sshRNAs do not silence target RNA expression. In an Ago2 pull-down assay that was performed as described in Example 14, 5'-end-labeled "pre-sliced" sshRNA SG244 was not stably bound to Ago2 (FIG. 14B). These results suggest that, although Ago2 can slice SG224 and remain bound to the large product of that cleavage reaction, a longer duplex is necessary for efficient RISC-loading, and without RISC-loading no silencing is seen.

Example 16: Efficacy of Modified sshRNA In Vivo

Figure 15:
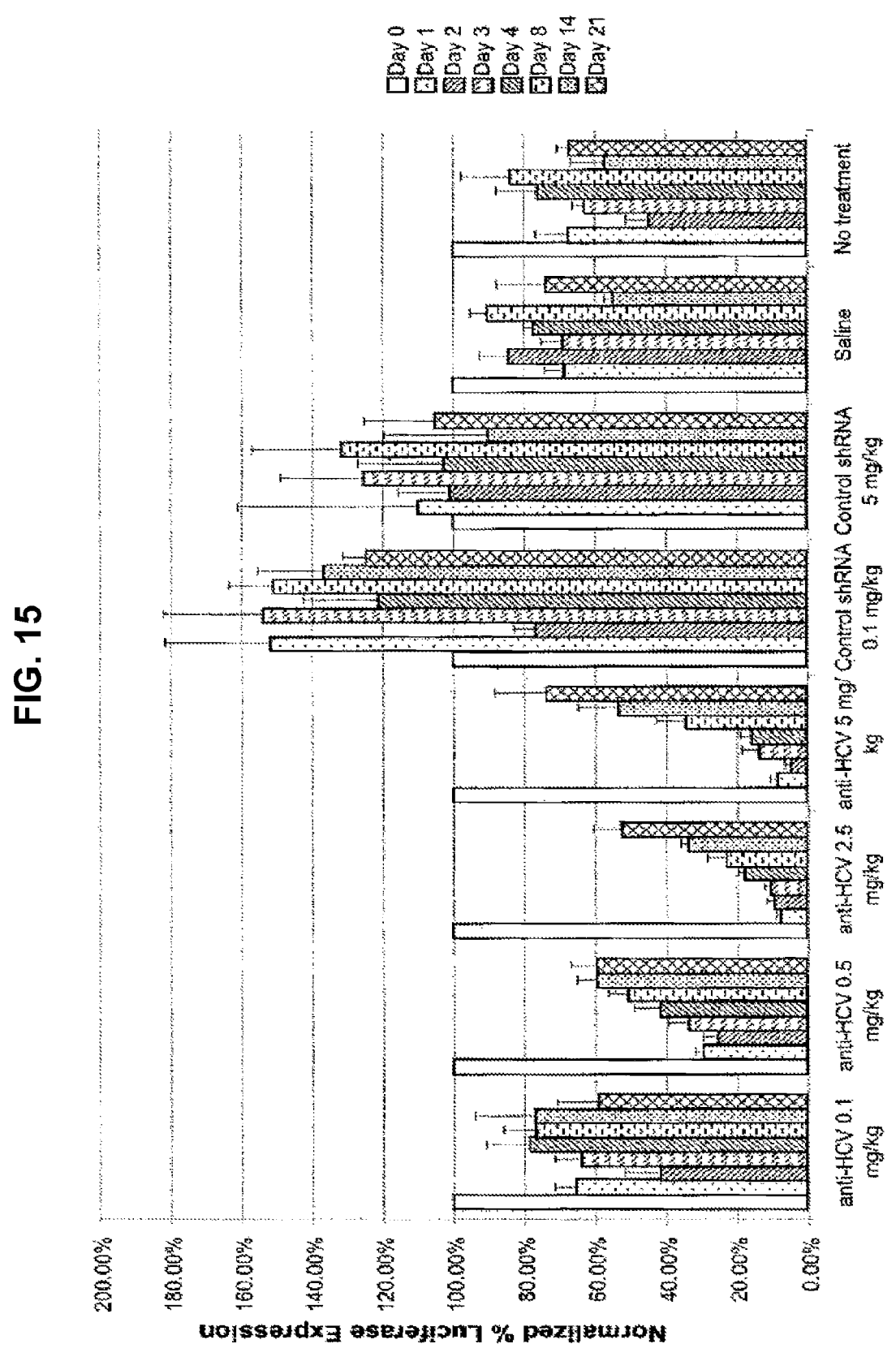

To establish the efficacy of shRNAs modified according to the present invention, we formulated SG224 with a third-party nanoparticle formulation and administered the composition into mice via a low-pressure tail vein injection. The mice were stably expressing a fusion mRNA containing the HCV IRES linked to the firefly luciferase coding region, having been administered 7 days previously a plasmid vector expressing that construct driven by the liver-specific promoter ApoE (2×)hAAT. The expression of luciferase was monitored by in vivo imaging with a Xenogen/Caliper IVIS-50 camera on successive days and weeks as showed in FIG. 15. Target knockdown was dose-dependent, reaching greater than 90% inhibition one day after administration of the formulated HCV-directed shRNA at 2.5 mg/kg. The lowest dose, 0.1 mg/kg, gave over 50% knockdown on day 2, although inhibition dropped on subsequent days. Negative controls, including an sshRNA with a scrambled version of the SG224 sequence (SG221(c)) as well as saline and no treatment showed no target knockdown. SG224's 2'-O-Me modifications (FIG. 11) improve serum stability and abrogate immune stimulatory effects. This RNA was largely intact after a 6-h incubation at 37° C. in 10% human serum (FIG. 7), and this level of nuclease resistance was sufficient to provide a sustained knockdown in vivo: greater than 75% inhibition remained at day 8 and 50% remained 3 weeks following administration of a dose of 2.5 mg/kg (FIG. 15).

Example 17: Effect of Cholesterol Modification on shRNA Activity

We tested whether cholesterol modification affects the activity of right hand loop shRNAs (Table 16). Transfections of shRNAs that have 5'-end, 3'-end, or loop-conjugated cholesterol moieties (synthesized by IDT) in 293 FT cells and luciferase assays were performed as described in Example 1. These shRNAs are 45mers with a 19 bp stem, a 5 nt loop, and a 3'UU overhang of the same sequence as SG68. Silencing activity of the cholesterol-modified shRNAs was compared with the silencing activity of the unmodified shRNA of the same sequence (SG68, prepared by in vitro transcription by T7 RNA polymerase as described in Vlassov et al 2007). Molecules with cholesterol modification in the loop or modification at either the 5' or 3' ends retained their ability to inhibit luciferase expression albeit at lower efficacy relative to SG68 (see Table 16). 5'-end conjugation had the biggest reduction in activity (46.98% silencing vs. 87.73% for unmodified at 1 nM).

TABLE 16

Effect of cholesterol modification on shRNA activity

| Cholesterol modification site | % luciferase silencing | |
|---|---|---|
| | 1 nM | 5 nM |
| 3'-end | 63.62 ± 0.31 | 87.12 ± 0.18 |
| 5'-end | 46.98 ± 1.45 | 81.78 ± 0.42 |
| Loop | 67.64 ± 1.19 | 90.52 ± 0.36 |
| SG68 (unmodified) | 87.73 ± 0.11 | 96.32 ± 0.12 |

Other Embodiments

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

REFERENCES CITED

Amarzguioui, M., Lundberg, P., Cantin, E., Hagstrom, J., Behlke, M. A., and Rossi, J. J. 2006. Rational design and in vitro and in vivo delivery of Dicer substrate siRNA. Nat Protoc 1(2): 508-517.

Behlke, M. A. 2006. Progress towards in vivo use of siRNAs. Mol Ther 13(4): 644-670.

Behlke, M. A. 2008. Chemical modification of siRNAs for in vivo use. Oligonucleotides 18: 305-19.

Bernards, R., Brummelkamp, T. R., and Beijersbergen, R. L. 2006. shRNA libraries and their use in cancer genetics. Nat Methods 3(9): 701-706.

Chang, K., Elledge, S. J., and Hannon, G. J. 2006. Lessons from Nature: microRNA-based shRNA libraries. Nat Methods 3(9): 707-714.

Cifuentes. D., Xue, H., Taylor, D. W., Patnode, H., Mishima, Y., Cheloufi, S., Ma, E., Mane, S., Hannon, G. J., Lawson, N. D., Wolfe, S. A., Giraldez, A. J. 2010. A novel miRNA processing pathway independent of Dicer requires Argonaute2 catalytic activity. Science 328: 1694-8.

Corey, D. R. 2007. Chemical modification: the key to clinical application of RNA interference? J. Clin. Invest. 117: 3615-22.

Dorsett, Y. and Tuschl, T. 2004. siRNAs: applications in functional genomics and potential as therapeutics. Nat Rev Drug Discov 3(4): 318-329.

Elbashir, S. M., Harborth, J., Lendeckel, W., Yalcin, A., Weber, K., and Tuschl, T. 2001. Duplexes of 21-nucleotide RNAs mediate RNA interference in cultured mammalian cells. Nature 411(6836): 494-498.

Fewell, G. D. and Schmitt, K. 2006. Vector-based RNAi approaches for stable, inducible and genome-wide screens. Drug Discov Today 11(21-22): 975-982.

Forsbach, A., Nemorin, J. G., Montino, C., Muller, C., Samulowitz, U., Vicari, A. P., Jurk, M., Mutwiri, G. K., Krieg, A. M., Lipford, G. B. et al. 2008. Identification of RNA sequence motifs stimulating sequence-specific TLR8-dependent immune responses. J Immunol 180(6): 3729-3738.

Harborth, J., Elbashir, S. M., Vandenburgh, K., Manninga, H., Scaringe, S. A., Weber, K., and Tuschl, T. 2003. Sequence, chemical, and structural variation of small interfering RNAs and short hairpin RNAs and the effect on mammalian gene silencing. Antisense Nucleic Acid Drug Dev 13(2): 83-105.

Harper, S. Q., Staber, P. D., He, X., Eliason, S. L., Martins, I. H., Mao, Q., Yang, L., Kotin, R. M., Paulson, H. L., and Davidson, B. L. 2005. RNA interference improves motor and neuropathological abnormalities in a Huntington's disease mouse model. Proc Natl Acad Sci USA 102(16): 5820-5825.

Hayashi, F., Means, T. K., and Luster, A. D. 2003. Toll-like receptors stimulate human neutrophil function. Blood 102(7): 2660-2669.

Heil, F., Hemmi, H., Hochrein, H., Ampenberger, F., Kirschning, C., Akira, S., Lipford, G., Wagner, H., and Bauer, S. 2004. Species-specific recognition of single-stranded RNA via toll-like receptor 7 and 8. Science 303(5663): 1526-1529.

Hornung, V., Guenthner-Biller, M., Bourquin, C., Ablasser, A., Schlee, M., Uematsu, S., Noronha, A., Manoharan, M., Akira, S., de Fougerolles, A. et al. 2005. Sequence-specific potent induction of IFN-alpha by short interfering RNA in plasmacytoid dendritic cells through TLR7. Nat Med 11(3): 263-270.

Judge, A. and MacLachlan, I. 2008. Overcoming the innate immune response to small interfering RNA. Hum Gene Ther 19(2): 111-124.

Judge, A. D., Bola, G., Lee, A. C., and MacLachlan, I. 2006. Design of noninflammatory synthetic siRNA mediating potent gene silencing in vivo. Mol Ther 13(3): 494-505.

Judge, A. D., Sood, V., Shaw, J. R., Fang, D., McClintock, K., and MacLachlan, I. 2005. Sequence-dependent stimulation of the mammalian innate immune response by synthetic siRNA. Nat Biotechnol 23(4): 457-462.

Kariko, K., Bhuyan, P., Capodici, J., and Weissman, D. 2004. Small interfering RNAs mediate sequence-independent gene suppression and induce immune activation by signaling through toll-like receptor 3. J Immunol 172(11): 6545-6549.

Kim, D. H., Longo, M., Han, Y., Lundberg, P., Cantin, E., and Rossi, J. J. 2004. Interferon induction by siRNAs and ssRNAs synthesized by phage polymerase. Nat Biotechnol 22(3): 321-325.

Li, L., Lin, X., Khvorova, A., Fesik, S. W., and Shen, Y. 2007. Defining the optimal parameters for hairpin-based knockdown constructs. Rna 13(10): 1765-1774.

Manoharan, M. 2004. RNA interference and chemically modified small interfering RNAs. Curr. Opin. Chem. Biol. 8: 570-9.

Marques, J. T., Devosse, T., Wang, D., Zamanian-Daryoush, M., Serbinowski, P., Hartmann, R., Fujita, T., Behlke, M. A., and Williams, B. R. 2006. A structural basis for discriminating between self and nonself double-stranded RNAs in mammalian cells. Nat Biotechnol 24(5): 559-565.

McManus, M. T., Petersen, C. P., Haines, B. B., Chen, J., and Sharp, P. A. 2002. Gene silencing using micro-RNA designed hairpins. Rna 8(6): 842-850.

Nishina, K., Unno, T., Uno, Y., Kubodera, T., Kanouchi, T., Mizusawa, H., and Yokota, T. 2008. Efficient In Vivo Delivery of siRNA to the Liver by Conjugation of alpha-Tocopherol. Mol Ther.

Poeck, H., Besch, R., Maihoefer, C., Renn, M., Tormo, D., Morskaya, S. S., Kirschnek, S., Gaffal, E., Landsberg, J., Hellmuth, J. et al. 2008. 5'-Triphosphate-siRNA: turning gene silencing and Rig-I activation against melanoma. Nat Med 14(11): 1256-1263.

Robb, G. B. and Rana, T. M. (2007) RNA helicase A interacts with RISC in human cells and functions in RISC loading. *Mol Cell,* 26, 523-537.

Robbins, M., Judge, A., Ambegia, E., Choi, C., Yaworski, E., Palmer, L., McClintock, K., and MacLachlan, I. 2008. Misinterpreting the therapeutic effects of small interfering RNA caused by immune stimulation. Hum Gene Ther 19(10): 991-999.

Schlee, M., Hornung, V., and Hartmann, G. 2006. siRNA and isRNA: two edges of one sword. Mol Ther 14(4): 463-470.

Shukla, S., Sumaria, C. S., Pradeepkumar, P. I. 2010. Exploring chemical modifications for siRNA therapeutics: a structural and functional outlook. ChemMedChem 5: 328-49.

Sioud, M. 2005. Induction of inflammatory cytokines and interferon responses by double-stranded and single-stranded siRNAs is sequence-dependent and requires endosomal localization. J Mol Biol 348(5): 1079-1090.

Soutschek, J., Akinc, A., Bramlage, B., Charisse, K., Constien, R., Donoghue, M., Elbashir, S., Geick, A., Hadwiger, P., Harborth, J. et al. 2004. Therapeutic silencing of an endogenous gene by systemic administration of modified siRNAs. Nature 432(7014): 173-178.

Terhorst, D., Kalali, B. N., Weidinger, S., Illig, T., Novak, N., Ring, J., Ollert, M., and Mempel, M. 2007. Monocyte-derived dendritic cells from highly atopic individuals are not impaired in their pro-inflammatory response to toll-like receptor ligands. Clin Exp Allergy 37(3): 381-390.

Vlassov, A. V., Ilves, H., and Johnston, B. H. 2006. Inhibition of hepatitis C IRES-mediated gene expression by 8-17 deoxyribozymes in human tissue culture cells. Dokl Biochem Biophys 410: 257-259.

Vlassov, A. V., Korba, B., Farrar, K., Mukerjee, S., Seyhan, A. A., Ilves, H., Kaspar, R. L., Leake, D., Kazakov, S. A., and Johnston, B. H. 2007. shRNAs targeting hepatitis C: effects of sequence and structural features, and comparison with siRNA. Oligonucleotides 17(2): 223-236.

Wang, B., Li, S., Qi, H. H., Chowdhury, D., Shi, Y., and Novina, C. D. 2009. Distinct passenger strand and mRNA cleavage activities of human Argonaute proteins. Nat. Struct. & Mol. Biol. 16(12): 1259-1266.

Watts, J. K., Deleavey, G. F., Damha, M. J. 2008. Chemically modified siRNA: tools and applications. Drug. Discov. Today 13: 842-55.

Xia, H., Mao, Q., Eliason, S. L., Harper, S. Q., Martins, I. H., Orr, H. T., Paulson, H. L., Yang, L., Kotin, R. M., and Davidson, B. L. 2004. RNAi suppresses polyglutamine-induced neurodegeneration in a model of spinocerebellar ataxia. Nat Med 10(8): 816-820.

Xia, H., Mao, Q., Paulson, H. L., and Davidson, B. L. 2002. siRNA-mediated gene silencing in vitro and in vivo. Nat Biotechnol 20(10): 1006-1010.

The invention claimed is:

1. A small hairpin RNA (shRNA) consisting essentially of:
   (a) a sense sequence consisting of 11 to 19 ribonucleotides;
   (b) an antisense sequence consisting of 16 to 19 ribonucleotides, wherein the antisense sequence is substantially complementary to the sense sequence;
   (c) a loop region directly connecting the 3' end of the antisense sequence to the 5' end of the sense sequence, wherein the loop region is selected from the group consisting of: two ribonucleotides, one ribonucleotide and a direct covalent connection between the sense sequence and the antisense sequence; and
   (d) an optional 5' overhang or a 3' overhang of at least one ribonucleotide,
   wherein the 5' end of the antisense sequence and the 3' end of the sense sequence are not connected by an internucleotide linkage, wherein the antisense sequence has no chemical modifications, and wherein the ribonucleotides of the sense sequence comprise a first chemically modified ribonucleotide, a second chemically modified ribonucleotide and an unmodified ribonucleotide, wherein the unmodified ribonucleotide is between the first chemically modified ribonucleotide and the second chemically modified ribonucleotide, and wherein the first chemically modified ribonucleotide, unmodified ribonucleotide and second chemically modified ribonucleotide are consecutive.

2. The shRNA of claim 1, wherein:
   (a) the first chemically modified ribonucleotide or the second chemically modified ribonucleotide comprises a modification selected from the group consisting of: 2'-H, 2'-OR, 2'-halo, 2'-SH, 2'-SR, 2'-NH2, 2'-NHR, 2'-NR2, and 2'-CN modification of one or more nucleotides, wherein R is an alkyl group; or
   (b) the shRNA comprises one or more phosphorothioate modifications of a backbone of the shRNA.

3. The shRNA of claim 2, wherein the 2'-OR is 2'-O-methyl.

4. The shRNA of claim 1, wherein the first chemically modified ribonucleotide and the second chemically modified ribonucleotide are not located at positions 9, 10 and 11 from the 5' end of the sense sequence.

5. The shRNA of claim 1, wherein the shRNA comprises from 1 to 10 phosphorothioate internucleotide linkages.

6. The shRNA of claim 1, wherein from 2% to 65% of the ribonucleotides in the shRNA are chemically modified.

7. The shRNA of claim 1, wherein the shRNA is from 28 to 44 nucleotides in length.

8. The shRNA of claim 1, wherein the sense sequence and the antisense sequence are 18 or 19 nucleotides in length and are substantially complementary.

9. The shRNA of claim 1, wherein the shRNA comprises an overhang region ranging from 1 to 10 ribonucleotides on an end of the antisense sequence or sense sequence.

10. The shRNA of claim 1, wherein the shRNA comprises a group selected from: a conjugate moiety, a detectable label, and any combination thereof, wherein said group is attached to a region of said shRNA selected from: a 5' end of the shRNA, a 3' end of the shRNA, and the loop region, wherein said group is optionally attached via a linker.

11. The shRNA of claim 1, wherein the shRNA comprises a conjugate moiety, wherein the conjugate moiety is selected from the group consisting of: a steroid, a cholesterol, a cholestanol, a stigmasterol, a cholanic acid, an ergosterol, a vitamin, a peptide, a protein, a galactose, derivatives thereof, and any combination thereof.

12. The shRNA of claim 1, wherein the shRNA retains at least 50% RNAi activity in a gene expression inhibition assay as compared to a corresponding RNA molecule not having the first and second chemically modified ribonucleotides.

13. The shRNA of claim 1, wherein the first and second chemically modified ribonucleotides confers reduced immunostimulatory activity, increased serum stability, or both, as compared to a corresponding shRNA not having the first and second chemically modified nucleotides.

14. A composition comprising the shRNA of claim 1 and a pharmaceutically acceptable carrier or excipient.

15. A method of inhibiting the expression of a target gene in a cell, comprising contacting the cell with the shRNA of claim 1, wherein the shRNA is specific for the target gene.

16. The method of claim 15, wherein the cell is in vivo.

17. The shRNA of claim 1, wherein the shRNA contains a mismatch or a bulge.

* * * * *